US011786165B2

(12) United States Patent
Arai et al.

(10) Patent No.: US 11,786,165 B2
(45) Date of Patent: Oct. 17, 2023

(54) PHYSIOLOGICAL STATE DETERMINATION DEVICE

(71) Applicants: DAIKIN INDUSTRIES, LTD., Osaka (JP); TOKYO INSTITUTE OF TECHNOLOGY, Tokyo (JP)

(72) Inventors: Junichiro Arai, Osaka (JP); Takashi Gotou, Osaka (JP); Akira Matsubara, Osaka (JP); Takahiro Hirayama, Osaka (JP); Hideki Hashizume, Osaka (JP); Arina Hashimoto, Osaka (JP); Yasunori Kotani, Tokyo (JP); Taro Tomatsu, Tokyo (JP); Yoshimi Ohgami, Tokyo (JP)

(73) Assignees: Daikin Industries, Ltd., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 622 days.

(21) Appl. No.: 16/604,071

(22) PCT Filed: Apr. 12, 2018

(86) PCT No.: PCT/JP2018/015404
§ 371 (c)(1),
(2) Date: Oct. 9, 2019

(87) PCT Pub. No.: WO2018/190403
PCT Pub. Date: Oct. 18, 2018

(65) Prior Publication Data
US 2020/0029884 A1    Jan. 30, 2020

(30) Foreign Application Priority Data
Apr. 14, 2017    (JP) .................... 2017-080917

(51) Int. Cl.
A61B 5/00 (2006.01)
G06T 7/00 (2017.01)
G06V 40/16 (2022.01)

(52) U.S. Cl.
CPC ............ *A61B 5/4064* (2013.01); *A61B 5/004* (2013.01); *G06T 7/0012* (2013.01);
(Continued)

(58) Field of Classification Search
CPC ....... A61B 5/4064; A61B 5/004; A61B 5/377; A61B 5/015; A61B 5/168; A61B 5/18;
(Continued)

(56) References Cited

U.S. PATENT DOCUMENTS 10,667,738 B2 * 6/2020 Arai .................... A61B 5/0042
10,709,338 B2 * 7/2020 Arai ..................... A61B 5/165
(Continued)

FOREIGN PATENT DOCUMENTS

JP    2008-259676 A    10/2008
JP    2008-282153 A    11/2008
(Continued)

OTHER PUBLICATIONS

International Preliminary Report of corresponding PCT Application No. PCT/JP2018/015404 dated Oct. 24, 2019.
(Continued)

*Primary Examiner* — Molly Wilburn
(74) *Attorney, Agent, or Firm* — Global IP Counselors, LLP

(57) ABSTRACT

A physiological state determination device determines a predetermined physiological state of a subject. The physiological state determination device includes a brain function activation information detection unit, a face change information acquisition unit, and a physiological state determination unit. The brain function activation information detec-
(Continued)

tion unit detects brain function activation information corresponding to a physiological state. The face change information acquisition unit acquires face change information indicating a time-series change in face data of a subject. The physiological state determination unit determines the predetermined physiological state of the subject based on the brain function activation information and the face change information.

20 Claims, 37 Drawing Sheets

(52) U.S. Cl.
CPC .......... *G06V 40/162* (2022.01); *G06V 40/166* (2022.01); *G06T 2207/30016* (2013.01); *G06T 2207/30201* (2013.01)

(58) Field of Classification Search
CPC ......... G06T 7/0012; G06T 2207/30016; G06T 2207/30201; G06V 40/162; G06V 40/166
See application file for complete search history.

(56) References Cited

U.S. PATENT DOCUMENTS

| | | | |
|---|---|---|---|
| 10,786,207 B2* | 9/2020 | Arai | A61B 5/4064 |
| 10,842,431 B2* | 11/2020 | Arai | A61B 5/026 |
| 2003/0016726 A1* | 1/2003 | Pavlidis | A61B 5/16 374/45 |
| 2009/0285456 A1* | 11/2009 | Moon | G06V 40/176 382/118 |
| 2010/0073503 A1 | 3/2010 | Tanaka et al. | |
| 2010/0191124 A1* | 7/2010 | Prokoski | G16H 30/20 600/473 |
| 2015/0094914 A1* | 4/2015 | Abreu | B60H 1/00742 701/1 |
| 2015/0363657 A1 | 12/2015 | Shigemura | |
| 2016/0073874 A1* | 3/2016 | Tsai | A61B 5/4094 351/210 |
| 2017/0281070 A1 | 10/2017 | Arai et al. | |
| 2018/0168451 A1 | 6/2018 | Arai et al. | |
| 2018/0289266 A1* | 10/2018 | Arai | A61B 5/165 |
| 2019/0059799 A1* | 2/2019 | Arai | A61B 5/0008 |

FOREIGN PATENT DOCUMENTS

| | | |
|---|---|---|
| JP | 2013-176406 A | 9/2013 |
| JP | 2016-49343 A | 4/2016 |
| JP | 2017-773 A | 1/2017 |
| WO | 2016/035719 A1 | 3/2016 |

OTHER PUBLICATIONS

Ryo Sakamoto et al.; Evaluation of the Driver's Temporary Arousal Level by Facial Skin Thermogram—Effect of Surrounding Temperature and Wind on the Thermogram—; IEEJ Trans. ELS, vol. 126, No. 7, 2006.
European Search Report of corresponding EP Application No. 18 78 4945.0 dated Dec. 15, 2020.
European Search Report of corresponding EP Application No. 21 205 403.5 dated Mar. 1, 2022.
International Search Report of corresponding PCT Application No. PCT/JP2018/015404 dated Jun. 12, 2018.

* cited by examiner

| SUBJECT (300) | PHYSIOLOGICAL STATE | BRAIN FUNCTION ACTIVATION STIMULUS | PREDETERMINED DEVICE (360) | SPECIFIC OPERATION | MEASURING PERSON (301) OTHER THAN SUBJECT |
|---|---|---|---|---|---|
| EXAMINEE | DEGREE OF CONCENTRATION (DEGREE OF CONCENTRATION ON EXAMINATION) | PRESENTATION OF EXAMINATION (PAPER OR TABLET) | EXAMINATION MANAGEMENT DEVICE | OPERATION OF INPUTTING START COMMAND AND TERMINATION COMMAND (SUCH AS PRESSING OF BUTTON) | EXAMINER |
| EXAMINEE | DEGREE OF CONCENTRATION (DEGREE OF CONCENTRATION ON EXAMINATION) | PRESENTATION OF EXAMINATION (TABLET) | EXAMINATION MANAGEMENT DEVICE + EXAMINATION EXECUTION DEVICE (TABLET) | OPERATION OF INPUTTING START COMMAND AND TERMINATION COMMAND (INPUT TO TABLET) | ABSENCE |
| ASSEMBLY WORKER | DEGREE OF CONCENTRATION (DEGREE OF CONCENTRATION ON ASSEMBLY WORK) | INSTRUCTION TO ASSEMBLE PARTS | PWORK LINE OPERATION DEVICE (OPERATION DEVICE FOR ASSEMBLY WORK LINE OF PARTS) | OPERATION OF INPUTTING OPERATION COMMAND (SUCH AS PRESSING OF BUTTON) | JOB SITE SUPERVISOR OR THE LIKE |
| ITEM CONSUMER | DEGREE OF INTEREST (DEGREE OF INTEREST OR CONCERN) | PRESENTATION OF ITEM (ITEM IS NOT ONLY PRODUCT BUT ALSO OBJECT THAT APPEALS TO FIVE SENSES, SUCH AS MUSIC) | ITEM PRESENTING DEVICE | OPERATION OF INPUTTING PRESENTATION COMMAND (SUCH AS PRESSING OF BUTTON) | ABSENCE |
| PATIENT OR THE LIKE | STATE OF DEPRESSION | PRESENTATION OF EMOTIONAL IMAGE | EXAMINATION DEVICE | OPERATION OF INPUTTING PRESENTATION COMMAND (SUCH AS PRESSING OF BUTTON) | DOCTOR OR THE LIKE |
| PATIENT OR THE LIKE | STATE OF AUTISM SPECTRUM DISORDER (ASD) SUCH AS AUTISM AND ASPERGER'S SYNDROME | PRESENTATION OF EXAMINATION TOOLS AND QUESTIONS SUCH AS IN AUTISM DIAGNOSTIC OBSERVATION SCHEDULE (ADOS) TEST | EXAMINATION DEVICE | OPERATION OF INPUTTING PRESENTATION COMMAND (SUCH AS PRESSING OF BUTTON) | DOCTOR OR THE LIKE |
| PATIENT OR THE LIKE | STATE OF DEMENTIA | PRESENTATION OF QUESTIONS SUCH AS IN REVISED HASEGAWA DEMENTIA SCALE (HDS-R), OR MMSE (MINI-MENTAL STATE EXAM) | EXAMINATION DEVICE | OPERATION OF INPUTTING PRESENTATION COMMAND (SUCH AS PRESSING OF BUTTON) | DOCTOR OR THE LIKE |
| PATIENT OR THE LIKE | STATE OF POST-TRAUMATIC STRESS DISORDER (PTSD) | PRESENTATION OF QUESTIONS SUCH AS FOR PTSD ASSESSMENT SCALE (IES-R) | EXAMINATION DEVICE | OPERATION OF INPUTTING PRESENTATION COMMAND (SUCH AS PRESSING OF BUTTON) | DOCTOR OR THE LIKE |
| PATIENT OR THE LIKE | STATE OF ANXIETY DISORDER | PRESENTATION OF QUESTIONS SUCH AS FOR LIEBOWITZ SOCIAL ANXIETY SCALE (LSAS-J) | EXAMINATION DEVICE | OPERATION OF INPUTTING PRESENTATION COMMAND (SUCH AS PRESSING OF BUTTON) | DOCTOR OR THE LIKE |
| PATIENT OR THE LIKE | STATE OF PTSD THERAPY | PRESENTATION OF QUESTIONS SUCH AS IN PROLONGED EXPOSURE THERAPY OR EYE MOVEMENT DESENSITIZATION THERAPY | EXAMINATION DEVICE | OPERATION OF INPUTTING PRESENTATION COMMAND (SUCH AS PRESSING OF BUTTON) | DOCTOR OR THE LIKE |
| SUBJECT (ARBITRARY) | DEGREE OF CONCENTRATION (DEGREE OF "HABITUATION") | INSTRUCTION TO PERFORM OPERATION ACTION | POPERATION INSTRUCTION OUTPUT DEVICE | OPERATION OF INPUTTING PRESENTATION COMMAND (SUCH AS PRESSING OF BUTTON) | MEASURING PERSON (ARBITRARY) |
| SUBJECT (ARBITRARY) | DEGREE OF CONCENTRATION (DEGREE OF "HABITUATION") | INSTRUCTION TO VIEW IMAGE | IMAGE OUTPUT DEVICE | OPERATION OF INPUTTING PRESENTATION COMMAND (SUCH AS PRESSING OF BUTTON) | MEASURING PERSON (ARBITRARY) |
| ELDERLY PERSON OR THE LIKE | PSYCHOLOGICAL STATES OF COMMUNICATION PARTNER (SUCH AS WHETHER AGED PERSON IS NON-SENILE) | INQUIRY VIA TELEPHONE CONVERSATION DEVICE (EVENT CONCERNING CONTENT TO BE COMMUNICATED, SUCH AS IMAGE AND LANGUAGE) | TELEPHONE CONVERSATION DEVICE | OPERATION OF INPUTTING RESPONSE (SUCH AS INPUTTING SPEECH TO TELEPHONE CONVERSATION DEVICE) | ABSENCE |

FIG. 23

| SUBJECT (300) | PHYSIOLOGICAL STATE | PREDETERMINED ENVIRONMENT (K) | BRAIN FUNCTION ACTIVATION STIMULUS | STATE INFORMATION | STATE INFORMATION FOR SPECIFIC ENVIRONMENT | STATE INFORMATION ACQUISITION UNIT (517) |
|---|---|---|---|---|---|---|
| DRIVER | DEGREE OF CONCENTRATION (DEGREE OF CONCENTRATION OF DRIVER DURING DRIVING) | AREA WITHIN PREDETERMINED RANGE FROM CURRENT POSITION OF VEHICLE | RED LIGHT | SURROUNDING INFORMATION (SUCH AS IMAGE) | SURROUNDING INFORMATION OR THE LIKE THAT ALERTS DRIVER (SUCH AS RED-LIGHT IMAGE) | IN-VEHICLE CAMERA |
| DRIVER | DEGREE OF CONCENTRATION (DEGREE OF CONCENTRATION OF DRIVER DURING DRIVING) | AREA WITHIN PREDETERMINED RANGE FROM CURRENT POSITION OF VEHICLE | PRESENCE OF PEDESTRIANS, OTHER VEHICLES AND THE LIKE, INTERSECTION, OR PEDESTRIAN CROSSING | POSITION INFORMATION | POSITION INFORMATION OR THE LIKE THAT ALERTS DRIVER (COMBINED WITH MAP INFORMATION) | GPS SYSTEM OR THE LIKE |
| DRIVER | DEGREE OF CONCENTRATION (DEGREE OF CONCENTRATION OF DRIVER DURING DRIVING) | AREA WITHIN PREDETERMINED RANGE FROM CURRENT POSITION OF VEHICLE | PRESENCE OF PEDESTRIANS, OTHER VEHICLES AND THE LIKE, INTERSECTION, OR PEDESTRIAN CROSSING | SURROUNDING INFORMATION (SUCH AS IMAGE) | SURROUNDING INFORMATION OR THE LIKE THAT ALERTS DRIVER | LASER |
| AIRCRAFT OPERATOR | DEGREE OF CONCENTRATION (AIRCRAFT OPERATOR'S AWARENESS) | AREA WITHIN PREDETERMINED RANGE FROM CURRENT POSITION OF AIRCRAFT | SITUATION WHERE AIRCRAFT NEEDS TO BE RECOVERED (SUCH AS STRONG WINDS) | ACCELERATION INFORMATION (+ POSTURE ANGLE OR THE LIKE) | ACCELERATION INFORMATION INDICATING STATE OF AIRCRAFT TO ALERT AIRCRAFT OPERATOR TO RECOVER AIRCRAFT | ACCELERATION SENSOR OR THE LIKE |
| RAILWAY DRIVER | DEGREE OF CONCENTRATION | AREA WITHIN PREDETERMINED RANGE FROM CURRENT POSITION OF TRAIN | ABNORMAL SITUATION | TRAIN DRIVING PARAMETERS | ABNORMAL VALUES FOR RESPECTIVE TRAIN DRIVING PARAMETERS (OUTPUT OF FAILURE ALARM) | SOUND DETECTION SENSOR OR THE LIKE SIGNAL |
| RAILWAY DRIVER | DEGREE OF CONCENTRATION | AREA WITHIN PREDETERMINED RANGE FROM CURRENT POSITION OF TRAIN | SITUATION WHERE CAREFUL MANEUVERING IS NECESSARY, SUCH AS TRAIN APPROACHING STATION (PRESENCE OF SIGNAL, SAFETY PERSONNEL, RAILROAD CROSSING, OR STATION) | POSITION INFORMATION | POSITION INFORMATION OR THE LIKE THAT ALERTS DRIVER (COMBINED WITH MAP INFORMATION) | GPS SYSTEM OR THE LIKE |
| RAILWAY DRIVER | DEGREE OF CONCENTRATION | AREA WITHIN PREDETERMINED RANGE FROM CURRENT POSITION OF TRAIN | SITUATION WHERE CAREFUL MANEUVERING IS NECESSARY, SUCH AS TRAIN APPROACHING STATION (PRESENCE OF SIGNAL, SAFETY PERSONNEL, RAILROAD CROSSING, OR STATION) | SURROUNDING INFORMATION (SUCH AS IMAGE) | SURROUNDING INFORMATION OR THE LIKE THAT ALERTS DRIVER | LASER, CAMERA |
| MOVIE THEATER VISITOR | DEGREE OF INTEREST (DEGREE OF INTEREST OR CONCERN) | ROOM IN WHICH MOVIE IS SCREENED | MOVIE THEATER VIDEO COMMERCIALS (CM) | TIME INFORMATION | CM-OUTPUT TIME INFORMATION OR THE LIKE (SCREENING SCHEDULE INFORMATION WITHIN TIME INFORMATION REGARDING MOVIE SCREENING | SCREENING SCHEDULE MANAGEMENT DEVICE OR THE LIKE |

FIG. 24

PHYSIOLOGICAL STATE DETERMINATION DEVICE

CROSS-REFERENCE TO RELATED APPLICATIONS

This U.S. National stage application claims priority under 35 U.S.C. § 119(a) to Japanese Patent Application No. 2017-080917, filed in Japan on Apr. 14, 2017, the entire contents of which are hereby incorporated herein by reference.

BACKGROUND

Field of the Invention

The present invention relates to a physiological state determination device.

Background Information

In recent years, attempts have been made to estimate brain activity of persons by utilizing data detected using electroencephalography (EEG), magnetic resonance imaging (fMRI: functional Magnetic Resonance Imaging), and near-infrared spectroscopy (NIRS) such as disclosed in (Japanese Unexamined Patent Application Publication No. 2013-176406. Further, applications to, for example, determination of the physiological state of the mind and body of a person from their estimated brain activity have been studied.

SUMMARY OF THE INVENTION

However, electroencephalography and near-infrared spectroscopy require preprocessing such as making a subject wear electrodes. Magnetic resonance imaging requires measurement within a predetermined MRI room. In short, the methods described above have problems such as complex preparatory work or limited measurement conditions. In addition, all of the methods described above require huge cost. Consequently, the methods described above sometimes make it difficult to, for example, determine the physiological state of the mind and body of the subject.

The issue to be addressed by the present invention is to provide an apparatus and method for making it possible to easily determine the physiological state of the mind and body of a subject.

In particular, it is an object of the present invention to provide a physiological state determination device that can easily determine the physiological state of a subject by detecting any brain function activation stimulus that activates a brain function of the subject.

A physiological state determination device according to a first aspect of the present invention includes a brain function activation information detection unit, a face change information acquisition unit, and a physiological state determination unit. The brain function activation information detection unit detects brain function activation information corresponding to a physiological state. The face change information acquisition unit acquires face change information indicating a time-series change in face data of a subject. The physiological state determination unit determines a predetermined physiological state of the subject on the basis of the brain function activation information and the face change information.

With the provision of the brain function activation information detection unit described above, the physiological state determination device according to the first aspect can detect brain function activation information from any brain function activation stimulus. With this configuration, the physiological state of the subject can be more easily determined than with a device that provides a brain function activation stimulus and determines a physiological state.

In the present invention, the term "physiological state" is used to indicate the mental state and physical state of any subject. For example, the mental state is represented using indices for mental fatigue, mental stress, the aimless state, the level of concentration, and so on. The physical state is represented using indices for physical fatigue, physical stress, and so on.

A physiological state determination device according to a second aspect of the present invention is the physiological state determination device according to the first aspect, wherein the brain function activation information detection unit further includes a specific operation detection unit and/or a specific environment detection unit. When a specific operation is performed on a predetermined device by the subject or a measuring person other than the subject, the specific operation detection unit determines that a brain function activation stimulus is provided to the subject, and detects the brain function activation information. When state information in a predetermined environment is state information for a specific environment in which a brain function activation stimulus is regarded as being present, the specific environment detection unit determines that the brain function activation stimulus is provided to the subject, and detects the brain function activation information.

With the configuration described above, the physiological state determination device according to the second aspect can detect brain function activation information in response to detection of a specific operation on the predetermined device and/or in response to detection of state information for a specific environment.

A physiological state determination device according to a third aspect of the present invention is the physiological state determination device according to the second aspect, wherein the face change information acquisition unit acquires the face change information when the specific operation detection unit detects that the specific operation is performed on the predetermined device. Alternatively, the face change information acquisition unit acquires the face change information when the specific environment detection unit detects that the state information in the predetermined environment is the state information for the specific environment in which the brain function activation stimulus is regarded as being present. Alternatively, the face change information acquisition unit acquires the face change information when the specific operation detection unit detects a specific operation and when the specific environment detection unit detects a specific environment.

In the physiological state determination device according to the third aspect, when a specific operation on the predetermined device is detected and/or when state information for a specific environment is detected, the face change information acquisition unit acquires face change information. This can avoid acquisition and/or storage of information unnecessary for determination.

A physiological state determination device according to a fourth aspect of the present invention is the physiological state determination device according to the third aspect, wherein the face change information acquisition unit acquires a reference for the face change information when the specific operation detection unit does not detect the specific operation, and/or the face change information acquisition unit acquires a reference for the face change information when the specific environment detection unit does not detect the state information for the specific environment.

In the physiological state determination device according to the fourth aspect, face change information used as a reference is acquired at a timing when no brain function activation stimulus is provided to the subject. Thus, it is possible to determine the physiological state of the subject on the basis of face change information acquired when brain function activation stimulus information is detected.

A physiological state determination device according to a fifth aspect of the present invention is the physiological state determination device according to the second aspect to the fourth aspect, wherein the brain function activation information detection unit is contained in a first device. The face change information acquisition unit and the physiological state determination unit are contained in a second device. The first device and the second device execute information communication to determine a physiological state of the subject.

In the physiological state determination device according to the fifth aspect, separating the first device for detecting brain function activation information from the second device having the other configuration allows only the first device to be moved. As a result, the physiological state determination device can increase the flexibility of the location where brain function activation information can be detected.

A physiological state determination device according to a sixth aspect of the present invention is the physiological state determination device according to the second aspect to the fifth aspect, further including an estimation unit that estimates that the brain function activation stimulus is provided to the subject. When the estimation unit estimates that the brain function activation stimulus is provided, the specific environment detection unit detects whether the state information in the predetermined environment is the state information for the specific environment in which the brain function activation stimulus is regarded as being present.

The physiological state determination device according to the sixth aspect can obtain a more reliable determination result of determining a physiological state by estimating that a brain function activation stimulus is provided to the subject.

A physiological state determination device according to a seventh aspect of the present invention is the physiological state determination device according to the sixth aspect, wherein the estimation unit estimates that the brain function activation stimulus is provided to the subject on the basis of information on any one or any combination of a line of sight, an angle of a face, and a physical activity of the subject.

The physiological state determination device according to the seventh aspect can increase the accuracy of estimation of whether a brain function activation stimulus is provided to the subject. As a result, a more reliable determination result of determining a physiological state can be achieved.

A physiological state determination device according to an eighth aspect of the present invention is the physiological state determination device according to the second aspect to the seventh aspect, further including a specific environment storage unit and a state information acquisition unit. The specific environment storage unit stores, in advance, the state information for the specific environment in which the brain activation stimulus is regarded as being present. The state information acquisition unit acquires state information for the predetermined environment. The specific environment detection unit matches the state information acquired by the state information acquisition unit against the state information stored in the specific environment storage unit, and determines whether the state information acquired by the state information acquisition unit is state information for a specific environment in which the brain activation stimulus is present to detect the brain function activation information.

With the configuration described above, the physiological state determination device according to the eighth aspect can detect brain function activation information in response to detection of state information for a specific environment.

A physiological state determination device according to a ninth aspect of the present invention is the physiological state determination device according to the first aspect to the eighth aspect, further including a determination-information generation unit that generates determination information from the face change information. The physiological state determination unit determines the physiological state on the basis of the determination information.

The physiological state determination device according to the ninth aspect can determine the physiological state of the subject on the basis of determination information for determining a physiological state, which is generated from the face change information.

A physiological state determination device according to a tenth aspect of the present invention is the physiological state determination device according to the ninth aspect, further including a face change information decomposition unit that decomposes the face change information into a plurality of components by using singular value decomposition, principal component analysis, or independent component analysis. The determination-information generation unit extracts a component related to the brain function activation information from among the plurality of components as a determination component, and generates the determination information from the determination component.

In the physiological state determination device according to the tenth aspect, a determination component related to brain function activation information is extracted from among a plurality of components obtained by subjecting face change information to singular value decomposition/principal component analysis/independent component analysis. This eliminates a need to make a subject wear a special device such as electrodes, and makes it possible to easily estimate the presence of brain activity of the subject. Thus, the physiological state of the subject can be easily determined on the basis of a determination component corresponding to the brain function of the subject.

In the physiological state determination device according to the first aspect, it is possible to detect brain function activation information from any brain function activation stimulus provider.

In the physiological state determination device according to the second aspect, it is possible to detect brain function activation information in response to detection of a specific operation on a predetermined device and/or in response to detection of state information for a specific environment.

In the physiological state determination device according to the third aspect, it is possible to avoid acquisition and/or storage of information unnecessary for determination.

In the physiological state determination device according to the fourth aspect, it is possible to determine the physiological state of a subject.

In the physiological state determination device according to the fifth aspect, it is possible to increase the flexibility of the location where brain function activation information can be detected.

In the physiological state determination device according to the sixth aspect, it is possible to obtain a more reliable determination result of determining a physiological state.

In the physiological state determination device according to the seventh aspect, it is possible to increase the accuracy of estimation of whether a brain function activation stimulus is provided to a subject.

In the physiological state determination device according to the eighth aspect, it is possible to detect brain function activation information in response to detection of state information for a specific environment.

In the physiological state determination device according to the ninth aspect, it is possible to determine the physiological state of a subject on the basis of determination information for determining a physiological state, which is generated from face change information.

In the physiological state determination device according to the tenth aspect, it is possible to easily determine the physiological state of a subject.

BRIEF DESCRIPTION OF THE DRAWINGS

FIG. 23 is a diagram describing physiological states of a subject to be determined by a physiological state determination device according to the present invention, and information necessary therefor (brain function activation stimuli, predetermined devices, specific operations, and measuring persons).

FIG. 24 is a diagram describing physiological states of a subject to be determined by a physiological state determination device according to the present invention, and information necessary therefor (the content of brain function activation stimuli, predetermined environments, state information, state information for the specific environments, and the configuration of a state information acquisition unit).

FIG. 38 is a schematic diagram illustrating a configuration a physiological state determination device 700 according to a third embodiment.

DETAILED DESCRIPTION OF EMBODIMENT EMBODIMENT(S)

Figure 1B:
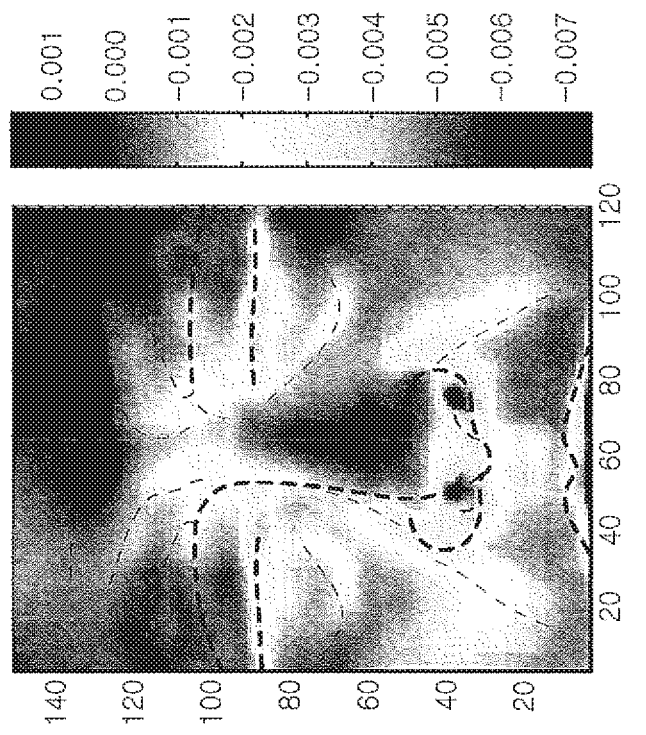
FIG. 1A and FIG. 1B include diagrams illustrating an example of captured image data and the result of analyzing the captured image data.

Before the description of an embodiment of the present invention, findings obtained by the inventors will be described first, which are the important basis of the present invention made by the inventors.

(1) Summary of Findings Obtained by the Inventors

It is known that human brain activity reflects human intellectual activity (such as cognitive activity) and emotional activity (activity such as with comfort/discomfort). Hitherto, attempts have been made to estimate human brain activity, in which case data detected using any method among electroencephalography, magnetic resonance imaging, and near-infrared spectroscopy is generally used.

For example, when electroencephalography is employed as a detection method, electroencephalogram electrodes need to be attached to the test subject. When electroencephalogram electrodes are attached, it is necessary to reduce resistance between the skin and the electrodes. Accordingly, operations are required, such as a process to abrade the skin and an application of a paste to the electrodes. When magnetic resonance imaging is employed, measurement at a location other than an MRI room is impossible, and, in addition, there are limited measurement conditions such as allowing no metal within the measurement room. When near-infrared spectroscopy is employed, a probe needs to be attached to the test subject. In some cases, wearing a probe for a long time makes the test subject feel pain, or accurate detection is not attained depending on the state of contact between the probe and the test subject's hair. Accordingly, when an existing detection method is employed to measure human brain activity, a great load is imposed on the test subject. For example, preprocessing is required when the electroencephalogram electrodes, the probe, or the like is attached, or there are limited measurement conditions.

It is therefore desirable to develop a means to reduce the load on the test subject and to facilitate estimation of human brain activity.

The inventors have considered the possibility of estimating human brain activity on the basis of the facial skin temperature of a person or on the basis of the condition of facial blood circulation considered to be proportional to the facial skin temperature. The facial skin temperature of a person can be acquired by using a measurement device such as a thermography device, and the condition of facial blood circulation, that is, the amount of facial blood circulation, can be estimated from RGB data of a captured face image obtained by using an imaging device. Accordingly, the facial skin temperature or a captured face image can be acquired without attachment of sensors that require processing before attachment, such as electroencephalogram electrodes or a probe.

On the other hand, it is known that the facial skin temperature of a person changes due to various factors such as ambient temperature and/or autonomic nervous activity. For this reason, if brain activity is to be estimated on the basis of the facial skin temperature or on the basis of the amount of facial blood circulation considered to be proportional to the facial skin temperature, it is considered very difficult to determine whether the acquired data reflects only brain activity.

As a result of intensive studies, the inventors have found that a component indicating a facial skin temperature change, or a change in the amount of facial blood circulation, that reflects brain activity can be identified by detecting facial skin temperatures, decomposing time-series facial skin temperature data, which includes detected temperature data and location data (coordinate data) of a detection region, or time-series facial blood-circulation-amount data calculated on the basis of RGB data obtained from time-series captured face image data, into a plurality of components by using singular value decomposition, principal component analysis, or independent component analysis, and analyzing the plurality of components obtained by decomposition. Then, the inventors have arrived at the present invention in which by estimating and analyzing the brain activity of the subject, the physiological state of the subject can be visualized on the basis of the estimated brain activity.

(2) Method for Acquiring Various Face Data and Method for Analyzing Acquired Various Data

(2-1) Method for Acquiring Facial Skin Temperature Data and Method for Analyzing Facial Skin Temperature Data Next, a method for acquiring facial skin temperature data and a method for analyzing facial skin temperature data, which are used by the inventors to obtain the findings described above, will be described.

In this test, facial skin temperature data was acquired from six test subjects. Specifically, the test subjects were seated in chairs placed in an artificial climate room maintained at a room temperature of 25° C., and facial skin temperature data was acquired from the entire areas of the faces of the test subjects by using an infrared thermography device. The infrared thermography device is a device capable of detecting infrared radiation energy emitted from a target object by using an infrared camera, converting the detected infrared radiation energy into temperatures (here, temperatures expressed in degrees Celsius) on the surface of the target object, and displaying and storing the distribution of the temperatures as facial skin temperature data (e.g., image data indicating the distribution of the temperatures). In the test, R300, manufactured by NEC Avio infrared Technologies Co., Ltd., was used as the infrared thermography device. The infrared camera was placed in front of the test subjects at a distance of 1.5 m from the test subjects. The facial skin temperature data was acquired for 30 minutes.

In the test, furthermore, the test subjects were presented with a brain function activation exercise during the acquisition of the facial skin temperature data. Accordingly, facial skin temperature data during a brain deactivation time and facial skin temperature data during a brain activation time were acquired. Examples of the brain function activation exercise include psychological tasks such as causing each test subject to perform calculations, recognize numbers, shapes, and colors, or memorize symbols, characters, or words on the basis of video images displayed on a display device or the like. In this test, "mental multiplication" was employed as a brain function activation exercise. Each test subject was assigned tasks of calculating written numbers displayed on the display device and inputting the answers by using a keyboard. In the test, the brain function activation exercise was presented to the test subjects for a duration of 10 minutes after the lapse of 5 minutes from the start of acquisition of the facial skin temperature data.

As the analysis of the facial skin temperature data, the acquired facial skin temperature data was subjected to the singular value decomposition using SVD (Singular Value Decomposition) of MATLAB (registered trademark) as an analysis tool. The singular value decomposition was performed on all the pieces of facial skin temperature data acquired in time series (30-minute data), in which the factor was time data obtained at intervals of 30 seconds (60 time points within 30 minutes) and the measure was the facial skin temperature data (240×320 pixels) within the period (a period of 30 seconds). Through the singular value decomposition, facial skin temperature data X was decomposed into a plurality of components, and a temporal distribution V and a spatial distribution U of each of the components, and a singular value S indicating the magnitude of each component were calculated. The relationship among them is represented by an equation below. In the equation, V' denotes a matrix in which the rows and columns of V are transposed.

$$x = (U*S)*V'_\# \qquad \text{<Math. 1>}$$

The temporal distribution V and the spatial distribution U of each component determined using the singular value decomposition were plotted on a graph, and a component waveform diagram and a temperature distribution diagram of each component were created.

Further, the created component waveform diagram and temperature distribution diagram of each component were analyzed to identify a component indicating a skin temperature change reflecting brain activity.

The component waveform diagram of each component was analyzed to determine the existence of a correlation between the amplitude of the component waveform of the component and each of the brain deactivation time and the brain activation time. Specifically, an evaluation was made of whether a correlation existed between the amplitude shown in the component waveform diagram of each component and the brain deactivation period/brain activation period. In this test, within the period during which the facial skin temperature data was acquired, the period during which no brain function activation exercise was presented to the test subjects, which was equal to a period of 5 minutes from the start of data acquisition until the elapse of 5 minutes and a period of 15 minutes from the time of elapse of 15 minutes after the start of data acquisition until the end of data acquisition, was set as the brain deactivation time, and the period during which the test subjects were presented with a brain function activation exercise, which was equal to a period of 10 minutes from the time of elapse of 5 minutes after the start of data acquisition until the elapse of 10 minutes, was set as the brain activation time. Then, an evaluation was made of the existence of a correlation between the amplitude shown in the component waveform diagram of each component and each of the brain deactivation time and the brain activation time. The determination of the existence of a correlation was performed using statistical correlation analysis. When the significance level (a) was 0.05 or less, it was determined that a correlation existed.

The temperature distribution diagram of each component was analyzed for the presence of a temperature change in a predetermined face region. The brain has a mechanism for cooling the brain while leaving the body temperature unchanged, called a selective brain cooling system. The selective brain cooling system is known to dissipate heat generated by brain activity through a forehead portion and a paranasal-sinus surrounding area including the glabella and an area around a nose portion). In this test, accordingly, an evaluation was made of whether a temperature change occurred in the paranasal-sinus surrounding area and the forehead portion on the temperature distribution diagram of each component. The presence of a temperature change in the paranasal-sinus surrounding area and the forehead portion on the temperature distribution diagram was determined by determining the presence of a temperature change by visual inspection or by determining whether the temperature of the paranasal-sinus surrounding area and the forehead portion was different from the average temperature of the overall measurement data by one standard deviation (SD) or more.

The determination of the polarity (plus or minus) of the facial skin temperature data. X is based on the relationship among the values of the spatial distribution U, the singular value S, and the temporal distribution V Accordingly, the polarity sometimes appears to be reversed on the component waveform diagram and temperature distribution diagram of each component. For this reason, the polarity is assumed to be excluded from the evaluation of the component waveform diagram and the temperature distribution diagram.

In the infrared thermography device, as described above, infrared radiation energy detected from a target object is converted into temperatures and the distribution of the temperatures is used as facial skin temperature data. When an infrared thermography device is used for a person to acquire the facial skin temperature of the person, a temperature change (so-called noise) that is not related to various brain activities such as movement of the face and/or autonomic nervous activity may also be acquired as facial skin temperature data (see FIG. 1A). To detect the temperature change not related to brain activity, relative facial skin temperature data was created such that all the average values of the pieces of temperature data included in facial skin temperature data obtained at intervals of 30 seconds were set to "0". The created facial skin temperature data was also subjected to the singular value decomposition using SVD of MATLAB (registered trademark) as an analysis tool to create a component waveform diagram and temperature distribution diagram of each component corresponding to the singular value S, which were analyzed to identify a component indicating a skin temperature change reflecting brain activity.

In the following, for convenience of description, facial skin temperature data acquired using an infrared thermography device is referred to as "facial skin temperature data corresponding to temperature conversion data", and relative facial skin temperature data in which all the average values of the pieces of temperature data included in facial skin temperature data corresponding to temperature conversion data obtained at intervals of a predetermined time (in this test, at intervals of 30 seconds) are set to "0" is referred to as "facial skin temperature data corresponding to relative temperature conversion data".

One of the six test subjects was also subjected to, in addition to the detection of the facial skin temperature by using an infrared thermography device, measurement of brain waves by connecting electrodes on the scalp of the test subject to also evaluate the correlation between the amplitude of the β wave (a brain wave in a frequency range of 14 to 30 Hz), which is known as a waveform that appears when people are awake or tense, and the amplitude shown in the component waveform diagram. In the measurement of the brain waves, the electrodes were placed at six locations (F3, F4, C3, C4, Cz, and Pz) based on the international 10-20 system.

While each test subject is presented with a brain function activation exercise, the head of the test subject may be moved upward and downward. This movement causes a change in the position of the face of the test subject relative to the infrared camera. To verify whether the change in the position of the face affects a skin temperature change, a contrast test was performed on one test subject. In a contrast test for verifying the influence of the movement of a test subject on the acquisition of facial skin temperature data, facial skin temperature data of the test subject was acquired by using an infrared thermography device in a way similar to that in the test described above. The test subject was also required to press the keyboard buttons at random timing while no brain function activation exercise was presented (i.e., the brain deactivation time). The facial skin temperature data corresponding to temperature conversion data and the facial skin temperature data corresponding to relative temperature conversion data, which were obtained by this contrast experiment, were also subjected to the singular value decomposition using SVD of MATLAB (registered trademark) as an analysis tool to create a component waveform diagram and temperature distribution diagram of each component corresponding to the singular value S, which were analyzed to identify a component indicating a skin temperature change reflecting brain activity.

Figure 1A:
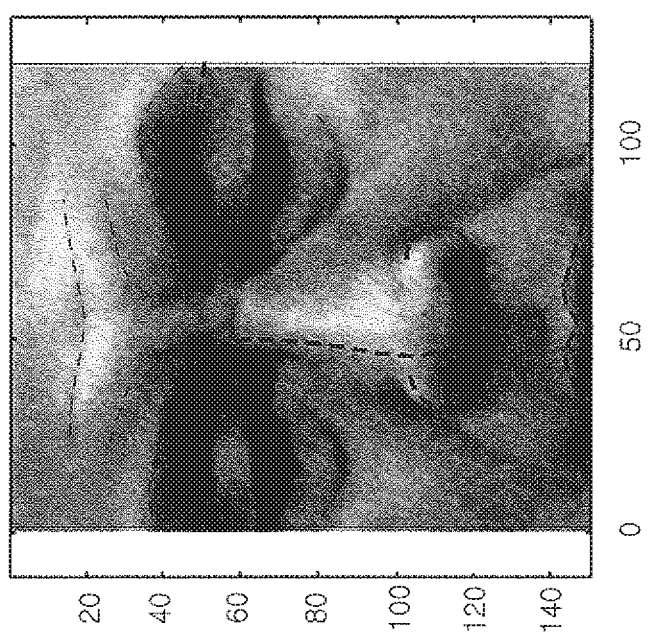

(2-2) Method for Acquiring Captured Face Image Data and Method for Analyzing Captured Face Image Data FIG. 1A is a diagram illustrating an example of captured image data of the paranasal-sinus surrounding area of the face of a test subject, which is captured using an imaging device. FIG. 1B is a diagram illustrating an example blood circulation amount distribution diagram (image map).

Next, a method for acquiring captured face image data and a method for analyzing captured face image data, which are used by the inventors to obtain the findings described above, will be described.

In this test, captured face image data was acquired from six test subjects. Specifically, the test subjects were seated in chairs placed in an artificial climate room maintained at a room temperature of 25° C., and captured image data of the paranasal-sinus surrounding areas of the entire areas of the faces of the test subjects was acquired in time series by using an imaging device capable of acquiring images in time series.

On the basis of the selective brain cooling system described above, a change in the amount of facial blood circulation considered to be proportional to the facial skin temperature that changes with brain activity is considered to occur in the forehead portion and/or the paranasal-sinus surrounding area. Accordingly, the inventors have considered that capturing a change in the amount of facial blood circulation in at least the forehead portion and/or the paranasal-sinus surrounding area enables accurate estimation of brain activity. In this test, captured image data of the paranasal-sinus surrounding area of the face of each test subject was acquired in time series.

In this test, furthermore, an imaging device installed on the liquid crystal display screen side of iPad Air (registered trademark), manufactured by Apple Inc., was used as an imaging device, and color moving image data was acquired as time-series captured image data. The imaging device was placed in front of the test subjects at a distance of 1.0 in from the test subjects. Then, the imaging device continuously captured image data for 30 minutes along the time axis in periods of 30 frames per second to obtain moving image data of the faces.

In this test, moreover, the test subjects were presented with a brain function activation exercise during the acquisition of the moving image data of the faces. Accordingly, moving image data of the faces at the brain deactivation time and moving image data of the faces at the brain activation time were acquired. In the test, as in the test described above, "mental multiplication" was employed as a brain function activation exercise. Each test subject was assigned tasks of calculating written numbers displayed on the display device and inputting the answers by using a keyboard. In the test, the brain function activation exercise was presented to the test subjects for a duration of 10 minutes after the lapse of 5 minutes from the start of acquisition of the moving image data of the faces.

As the analysis of the moving image data of the faces, blood-circulation-amount data was calculated on the basis of RGB data obtained from the captured moving image data of the faces, and the calculated time-series blood-circulation-amount data was subjected to the singular value decomposition using SVD of MATLAB (registered trademark) as an analysis tool. Here, an erythema index "a*" having a correlation with redness of the skin or the amount of hemoglobin, which was computed from RGB data of an image, was determined in accordance with the CIE-L*a*b* color system, and was defined as blood-circulation-amount data. The singular value decomposition was performed on the blood-circulation-amount data (here, the erythema index) based on RGB data obtained from all the pieces of moving image data acquired in time series (30-minute data), in which the factor was time data obtained at intervals of 30 seconds (60 time points within 30 minutes) and the measure was the erythema index computed from the RGB data for the period (at intervals of 30 seconds) (the erythema index computed from the average value of RGB values obtained from 1-second frame data extracted every 30 seconds; 240×320 pixels). Through the singular value decomposition, time-series blood-circulation-amount data based on the RGB data obtained from the moving image data of the faces is decomposed into a plurality of components, and a temporal distribution V and a spatial distribution U of each of the components, and a singular value S indicating the magnitude of each component were calculated. The relationship among them is represented by an equation similar to the equation above (Math. 1).

The temporal distribution V and the spatial distribution U of each component determined using the singular value decomposition were plotted on a graph, and a component waveform diagram and a blood circulation amount distribution diagram of each component were created.

Further, the created component waveform diagram and blood circulation amount distribution diagram of each component were analyzed to identify a component indicating a change in the amount of facial blood circulation, that is, a face RGB change, that reflects brain activity.

The component waveform diagram of each component was analyzed to determine the existence of a correlation between the amplitude of the component waveform of the component and each of the brain deactivation time and the brain activation time. Specifically, an evaluation was made of whether a correlation existed between the amplitude shown in the component waveform diagram of each component and the brain deactivation period/brain activation period. In this test, within the period during which captured face image data was acquired, the period during which no brain function activation exercise was presented to the test subjects, which was equal to a period of 5 minutes from the start of data acquisition until the elapse of 5 minutes and a period of 15 minutes from the time of elapse of 15 minutes after the start of data acquisition until the end of data acquisition, was set as the brain deactivation time, and the period during which the test subjects were presented with a brain function activation exercise, which was equal to a period of 10 minutes from the time of elapse of 5 minutes after the start of data acquisition until the elapse of 10 minutes, was set as the brain activation time. Then, an evaluation was made of the existence of a correlation between the amplitude shown in the component waveform diagram of each component and each of the brain deactivation time and the brain activation time. The determination of the existence of a correlation was performed using statistical correlation analysis. When the significance level (a) was 0.01 or less, it was determined that a correlation existed.

The blood circulation amount distribution diagram of each component was analyzed for the presence of a change in the amount of blood circulation in a predetermined face region. The blood circulation amount distribution diagram is created by arranging a spatial distribution U calculated for each pixel at the position of the pixel. An evaluation was made of whether a change in the amount of blood circulation occurred in the paranasal-sinus surrounding area and the forehead portion on the blood circulation amount distribution diagram of each component created in the way described above. The presence of a change in the amount of blood circulation in the paranasal-sinus surrounding area and the forehead portion on the blood circulation amount distribution diagram was determined by determining the presence of a change in the amount of blood circulation by visual inspection or by ensuring that the value of the amount of blood circulation in the paranasal-sinus surrounding area and the forehead portion illustrated in FIG. 1B is not "0.000".

The determination of the polarity (plus or minus) of blood-circulation-amount data X is based on the relationship among the values of the spatial distribution U, the singular value S, and the temporal distribution V. Accordingly, the polarity sometimes appears to be reversed on the component waveform diagram and blood circulation amount distribution diagram of each component. For this reason, the polarity is assumed to be excluded from the evaluation of the component waveform diagram and the blood circulation amount distribution diagram.

Further, to verify the correlation between the facial skin temperature and the amount of facial blood circulation, during the acquisition of captured face image data from the six test subjects in time series, facial skin temperature data was also acquired in time series by using an infrared thermography device, and the acquired facial skin temperature data was also subjected to the singular value decomposition using SVD of MATLAB (registered trademark) as an analysis tool to create a component waveform diagram of each component corresponding to the singular value S, which was analyzed to determine the existence of a correlation between the amplitude of the component waveform of the component and each of the brain deactivation time and the brain activation time. In this test, a device similar to that in the test described above was used as an infrared thermography device. The infrared camera was placed in front of the test subjects at a distance of 1.5 m from the test subjects.

When captured facial image data is acquired by using an imaging device, in some cases, sunlight or the like may hit the face when an image of the face is being captured, resulting in light being reflected from the face. The reflected light may enter the lens of the imaging device. In this case, the captured face image data has recorded thereon the reflected light. In the RGB data obtained from the captured image data, a change in lightness that is based on the amount of facial blood circulation is less than a change in lightness that is based on the reflected light. Thus, if the amount of blood circulation calculated on the basis of the RGB data obtained from the captured image data having recorded thereon the reflected light is analyzed, the analysis result may be likely to be contaminated with a face RGB change that is not related to brain activity (so-called noise). To prevent the contamination of the face RGB change not related to brain activity, relative blood-circulation-amount data was created from the relative RGB data in which all the average values of RGB data obtained at intervals of 30 seconds were set to "0". The created blood-circulation-amount data was also subjected to the singular value decomposition using SVD of MATLAB (registered trademark) as an analysis tool to create a component waveform diagram and blood circulation amount distribution diagram of each component corresponding to the singular value S, which were analyzed to identify a component indicating a face RGB change reflecting brain activity.

In the following, for convenience of description, relative blood-circulation-amount data based on relative RGB data in which all the average values of RGB data obtained at intervals of a predetermined time (in this test, at intervals of 30 seconds) are set to "0" is referred to as "relative conversion blood-circulation-amount data", and blood-circulation-amount data based on RGB data obtained before conversion to the relative RGB data is referred to simply as "blood-circulation-amount data".

During the acquisition of time-series captured face image data of the six test subjects by using an imaging device, each of the six test subjects was also subjected to measurement of brain waves by connecting electrodes on the scalp of the test subject to also evaluate the correlation between the amplitude of the β wave (a brain wave in a frequency range of 13 to 30 Hz), which is known as a waveform that appears when the brain cells are active, such as when the test subject is awake, and the amplitude shown in the component waveform diagram. In the measurement of the brain waves, the electrodes were placed at 19 locations (Fp1, Fp2, F3, F4, C3, C4, P3, P4, O1, O2, F7, F8, T3, T4, T5, T6, Fz, Cz, and Pz) on the scalp on the basis of the International 10-20 system.

While each test subject is presented with a brain function activation exercise, the head of the test subject may be moved upward and downward. This movement causes a change in the position of the face of the test subject relative to the imaging device. To verify whether the change in the position of the face affects a facial RGB change, a contrast test was performed on one test subject. In the contrast test, as in the test described above, time-series captured face image data of the test subject was acquired by using an imaging device. The test subject was also required to press the keyboard buttons at random timing while no brain function activation exercise was presented (i.e., the brain deactivation time). The time-series blood-circulationamount data based on the RGB data obtained from the time-series captured face image data captured in the contrast experiment was also subjected to the singular value decomposition using SVD of MATLAB (registered trademark) as an analysis tool to create a component waveform diagram of each component corresponding to the singular value S, which was analyzed to determine the existence of a correlation between the amplitude of the component waveform of the component and each of the brain deactivation time and the brain activation time. Further, analysis was made of the existence of a correlation between the amplitude of the component waveform of each component and actual movement of the face. The actual movement of the face was evaluated by acquiring two-dimensional coordinates of the same location on the face from the captured image data and calculating the movement distance of the face at intervals of 30 seconds during the image capturing operation with respect to the captured image data obtained when the contrast experiment was started. Further, analysis was also made of the existence of a correlation between the amplitude of the component waveform of each component and the number of keyboard inputs during the image capturing operation. The number of keyboard inputs during the image capturing operation was evaluated by calculating a simple moving average at intervals of 30 seconds in the time-series captured image data.

(3) Analysis Results (3-1) Analysis Results of Facial Skin Temperature Data

Figure 2A:
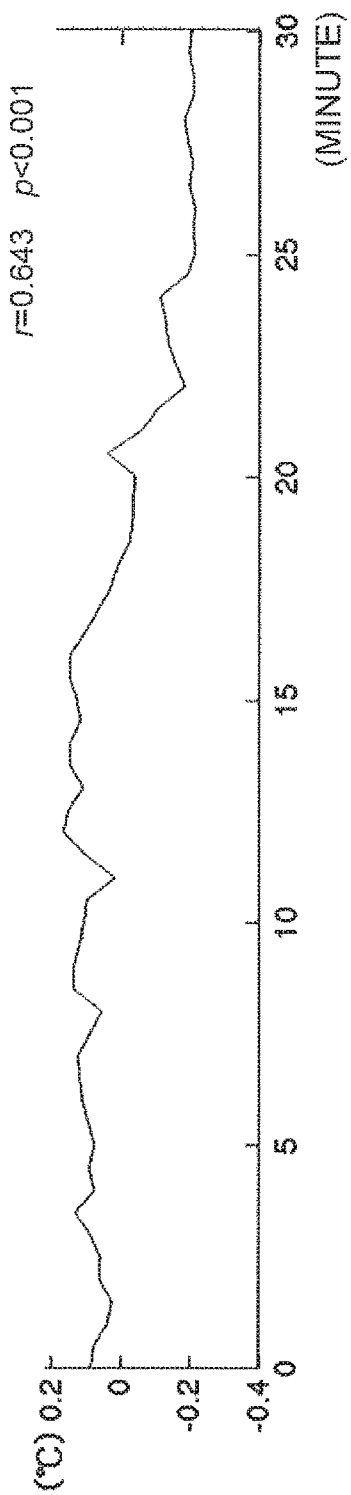
FIG. 2 includes FIG. 2A and FIG. 2B include diagrams illustrating part of the result of analyzing facial skin temperature data.
Figure 2B:
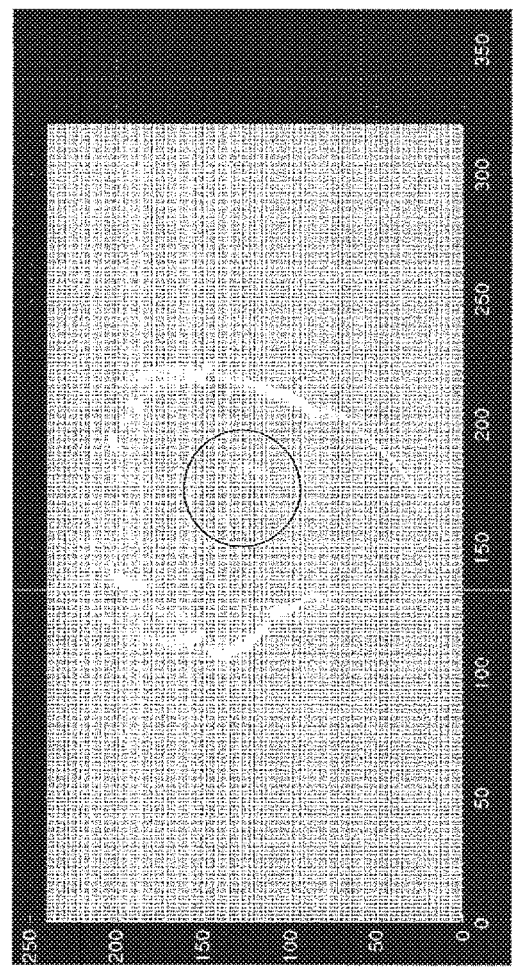
Figure 3A:
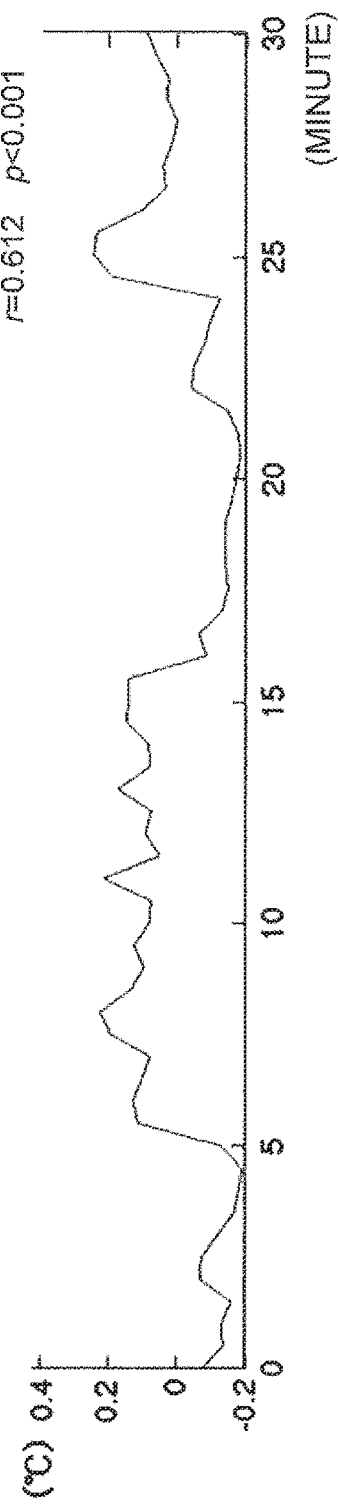
FIG. 3 includes FIG. 3A and FIG. 3B include diagrams illustrating part of the result of analyzing the facial skin temperature data.
Figure 3B:
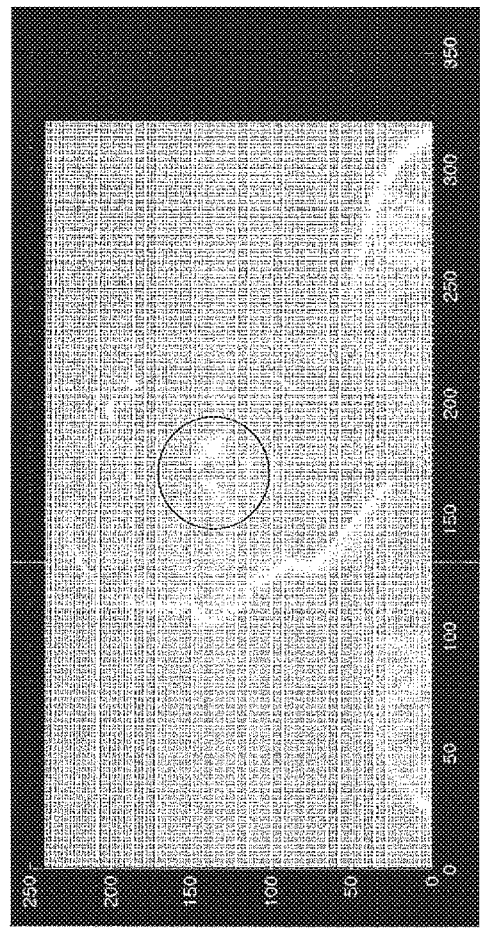
Figure 4:
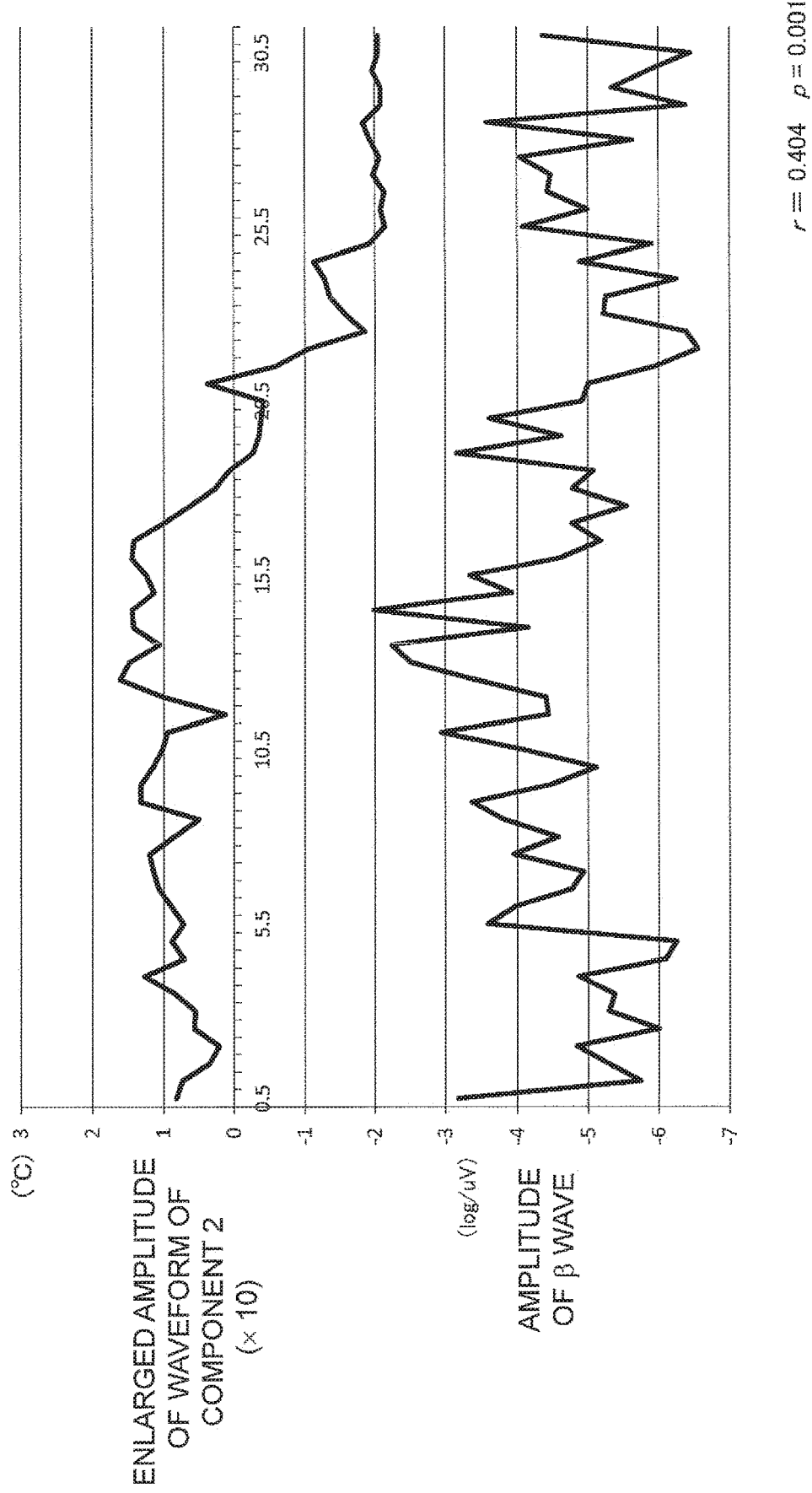
FIG. 4 is a diagram illustrating the amplitude of a component waveform of component 2 and the amplitude of the β wave among measured brain waves.
Figure 5:
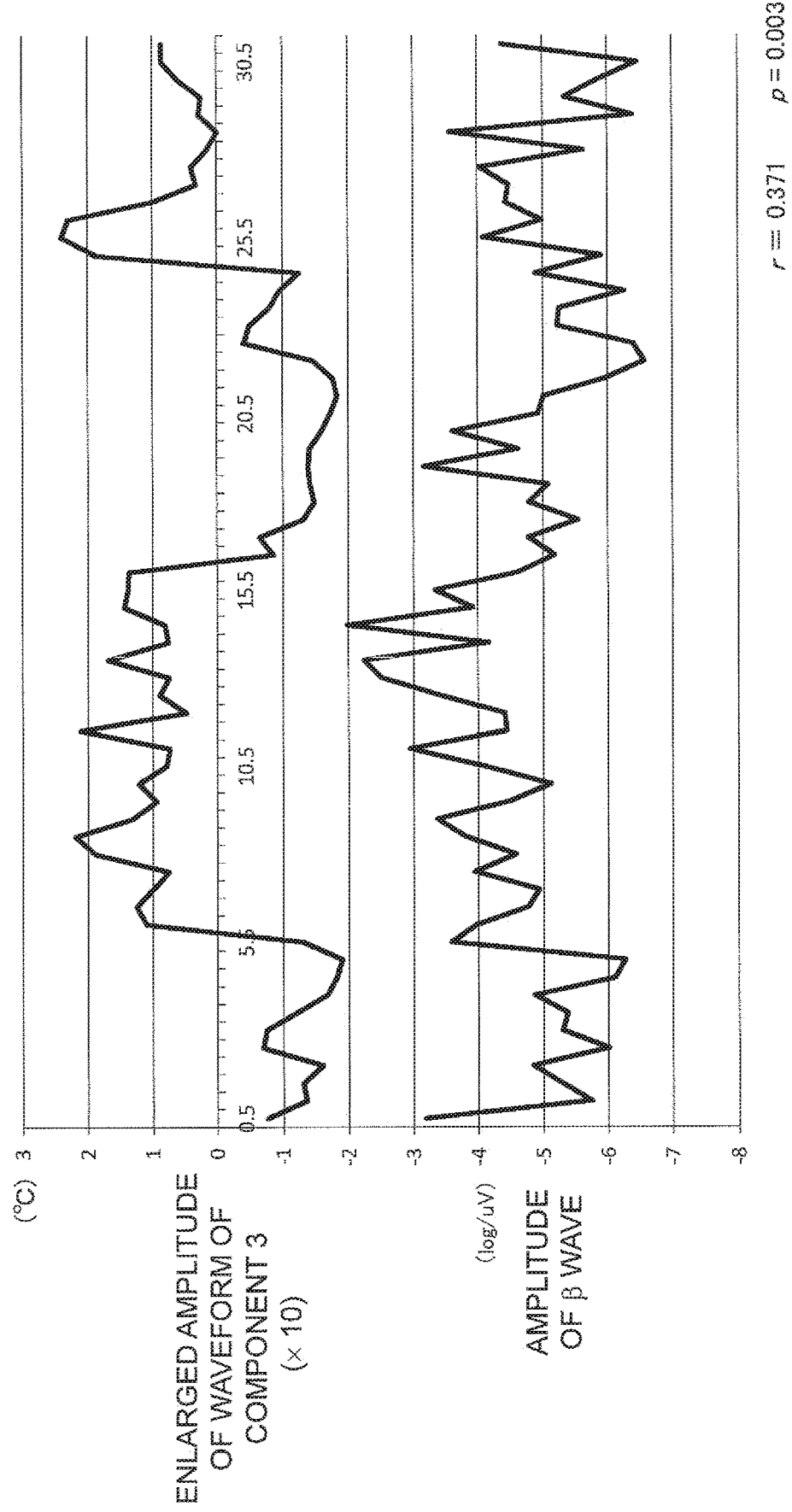
FIG. 5 is a diagram illustrating the amplitude of a component waveform of component 3 and the amplitude of the β wave among measured brain waves.
Figure 6A:
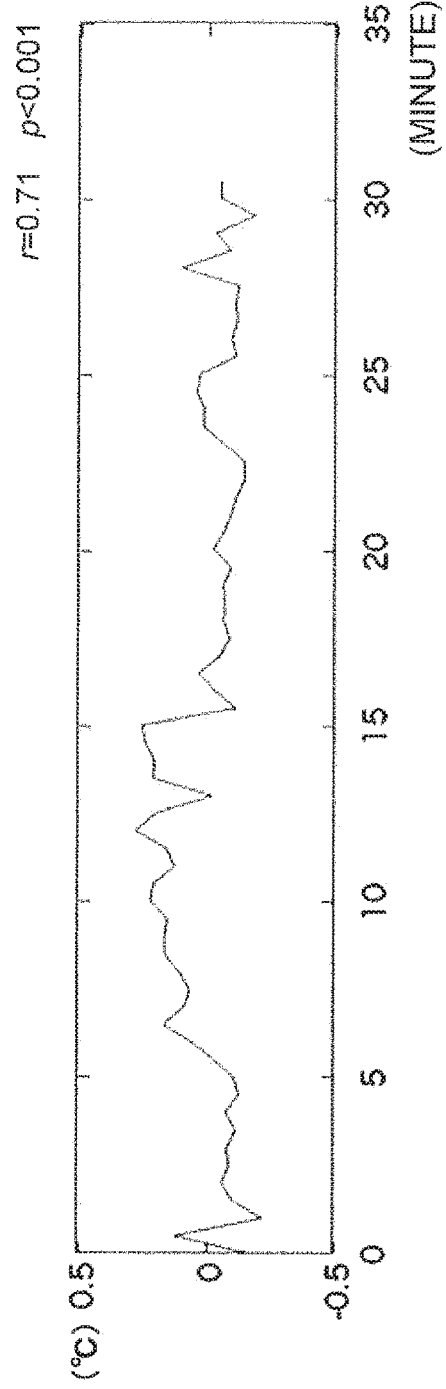
FIG. 6A and FIG. 6B include diagrams illustrating part of the result of analyzing facial skin temperature data obtained by a contrast experiment.
Figure 6B:
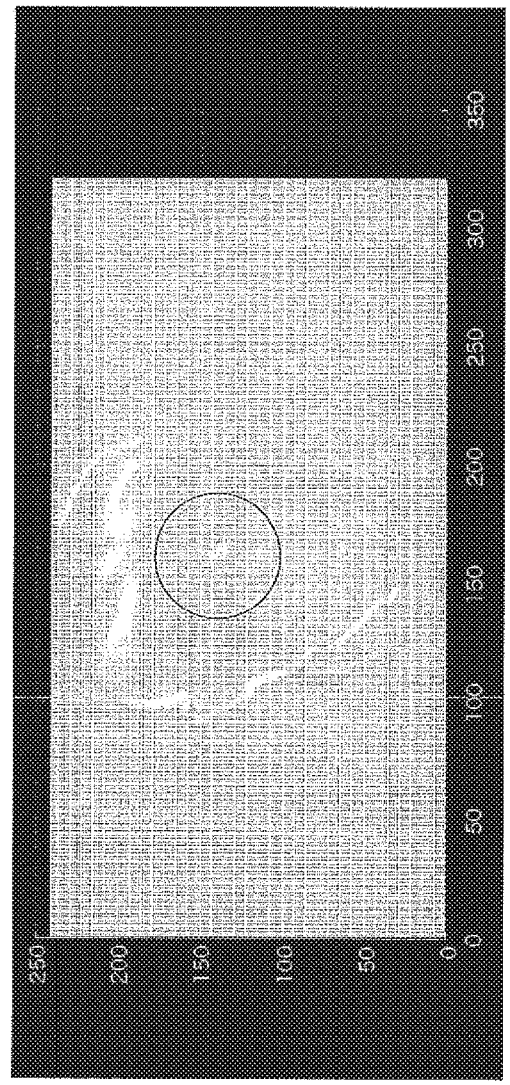

FIG. 2A and FIG. 2B include diagrams illustrating part of the result of analyzing facial skin temperature data corresponding to temperature conversion data. FIG. 2A illustrates a component waveform diagram of component 2 for test subject 1. FIG. 2B illustrates a temperature distribution diagram of the component 2 for the test subject 1. FIG. 3A illustrates a component waveform diagram of component 3 for the test subject 1. FIG. 3B illustrates a temperature distribution diagram of the component 3 for the test subject 1. FIG. 4 and FIG. 5 are diagrams illustrating relationships between the amplitudes of component waveforms and brain waves. FIG. 4 includes diagrams illustrating the amplitude of the component waveform of the component 2 for the test subject 1 and the amplitude of the β wave among measured brain waves. FIG. 5 includes diagrams illustrating the amplitude of the component waveform of the component 3 for the test subject 1 and the amplitude of the β wave among measured brain waves. FIG. 6A and FIG. 6B include diagrams illustrating part of the result of analyzing facial skin temperature data obtained by a contrast experiment. FIG. 6A illustrates a component waveform diagram of the component 3. FIG. 6B illustrates a temperature distribution diagram of the component 3.

Table 1 shows analysis results of facial skin temperature data of the test subjects.

The results obtained by the analysis of the facial skin temperature data described above indicate that a significant correlation exists between human brain activity and the component 2 and/or the component 3 among the plurality of components obtained by decomposing the time-series facial skin temperature data by using the singular value decomposition.

TABLE 1

|  | Correlation in Data Based on Absolute Temperature Conversion Data | | Correlation in Data Based on Relative Temperature Conversion Data | |
| --- | --- | --- | --- | --- |
| Test Subject # | Component waveform | Temperature distribution | Component waveform | Temperature distribution |
| Test Subject 1# | Component 2, Component 3 | Component 2, Component 3 | Component 2, Component 3 | Component 2, Component 3 |
| Test Subject 2# | Component 3 | Component 3 | Component 3 | Component 3 |
| Test Subject 3# | Component 1, Component 2, Component 3 | Component 2, Component 3 | Component 2, Component 3 | Component 2, Component 3 |
| Test Subject 4# | Component 2, Component 3 | Component 2, Component 3 | Component 2, Component 3 | Component 2, Component 3 |
| Test Subject 5# | Component 2, Component 3 | Component 2, Component 3 | Component 2, Component 3 | Component 2, Component 3 |
| Test Subject 6# | Component 2, Component 5 | Component 2, Component 5 | Component 2, Component 5 | Component 2, Component 5 |

As illustrated in FIG. 4 and FIG. 5, the results of brain wave analysis indicate that a significant correlation exists between the amplitudes of the component waveforms of the component 2 and the component 3 and the amplitude of the β wave of brain waves.

In the contrast experiment, furthermore, even if the test subject moves during the acquisition of the facial skin temperature data, a significant correlation existed between the component 3 and human brain activity (see FIG. 6A and FIG. 6B). This indicates that, among the plurality of components, the component 3 is not affected by the movement of the test subject during the acquisition of the facial skin temperature data.

From these results, the inventors have obtained the following findings.

As a result of decomposing the time-series facial skin temperature data acquired from the test subject into a plurality of components by using the singular value decomposition and analyzing the components obtained through decomposition, the component 3 among the plurality of components was found to be a component related to brain activity. That is, the time-series facial skin temperature data is decomposed into a plurality of components by using the singular value decomposition, a component having a correlation with the activation/deactivation of the brain is extracted from the plurality of components obtained through decomposition, and the extracted component is analyzed by utilizing the selective brain cooling system. Accordingly, it has turned out that a component indicating a skin temperature change reflecting brain activity can be identified from the plurality of components, From this, the inventors have obtained findings that brain activity can be estimated on the basis of the facial skin temperature of a person.

(3-2) Analysis Results of Captured Face Image Data

Figure 7:
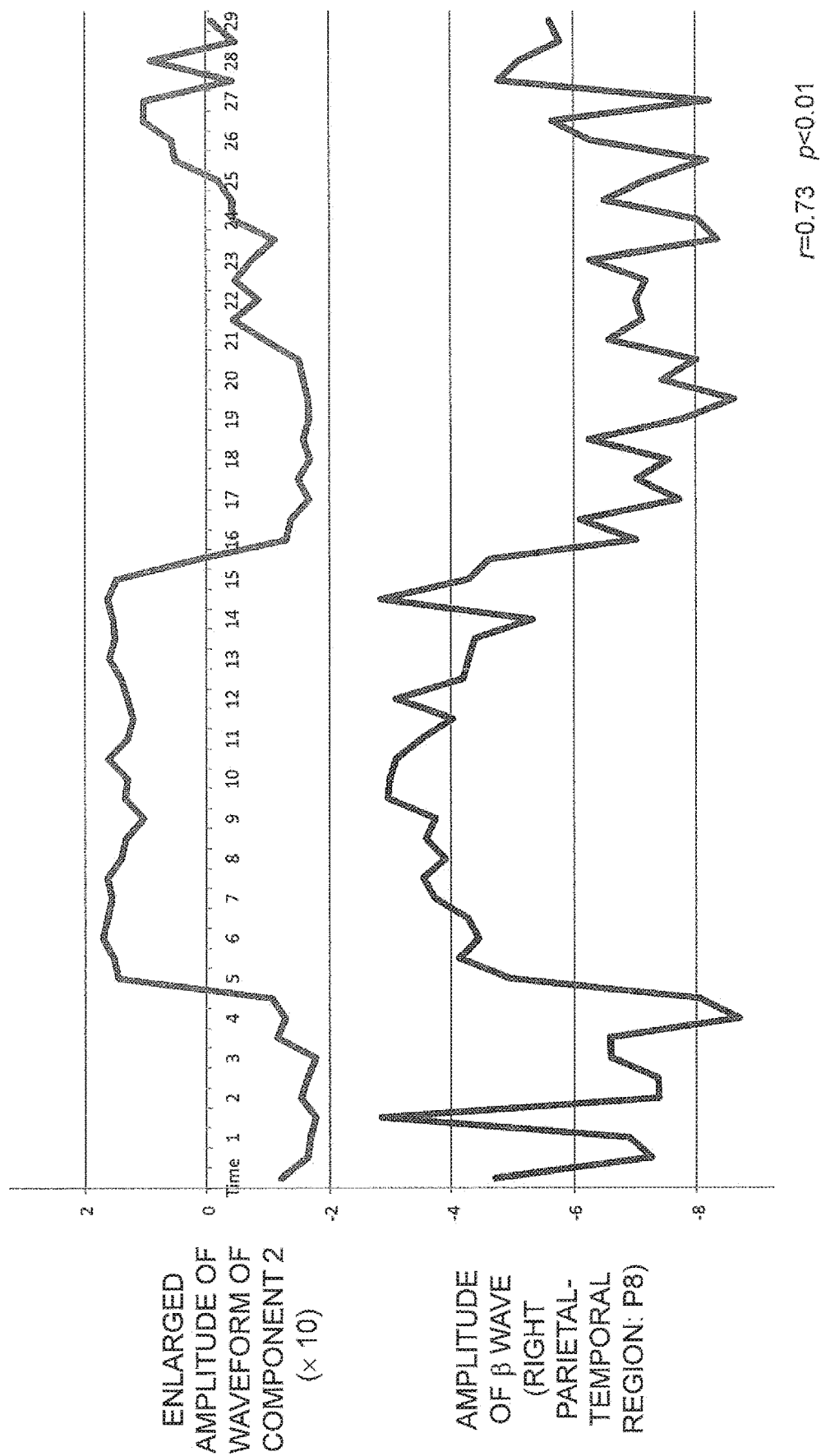
FIG. 7 is a diagram illustrating a component waveform based on captured image data of a face and the amplitude of the β wave among measured brain waves.
Figure 8:
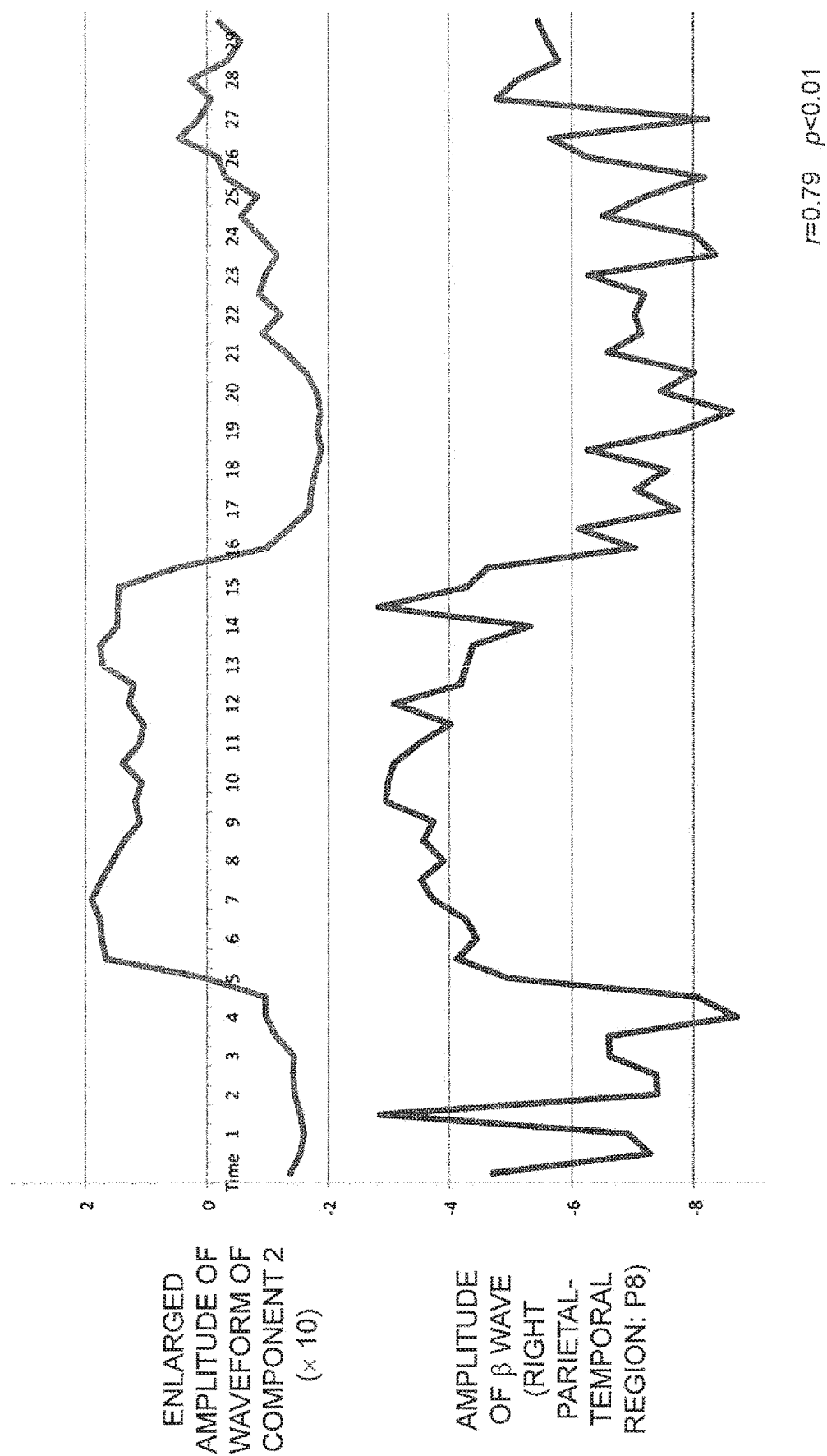
FIG. 8 is a diagram illustrating a component waveform based on facial skin temperature data and the amplitude of the β wave among measured brain waves.
Figure 9:
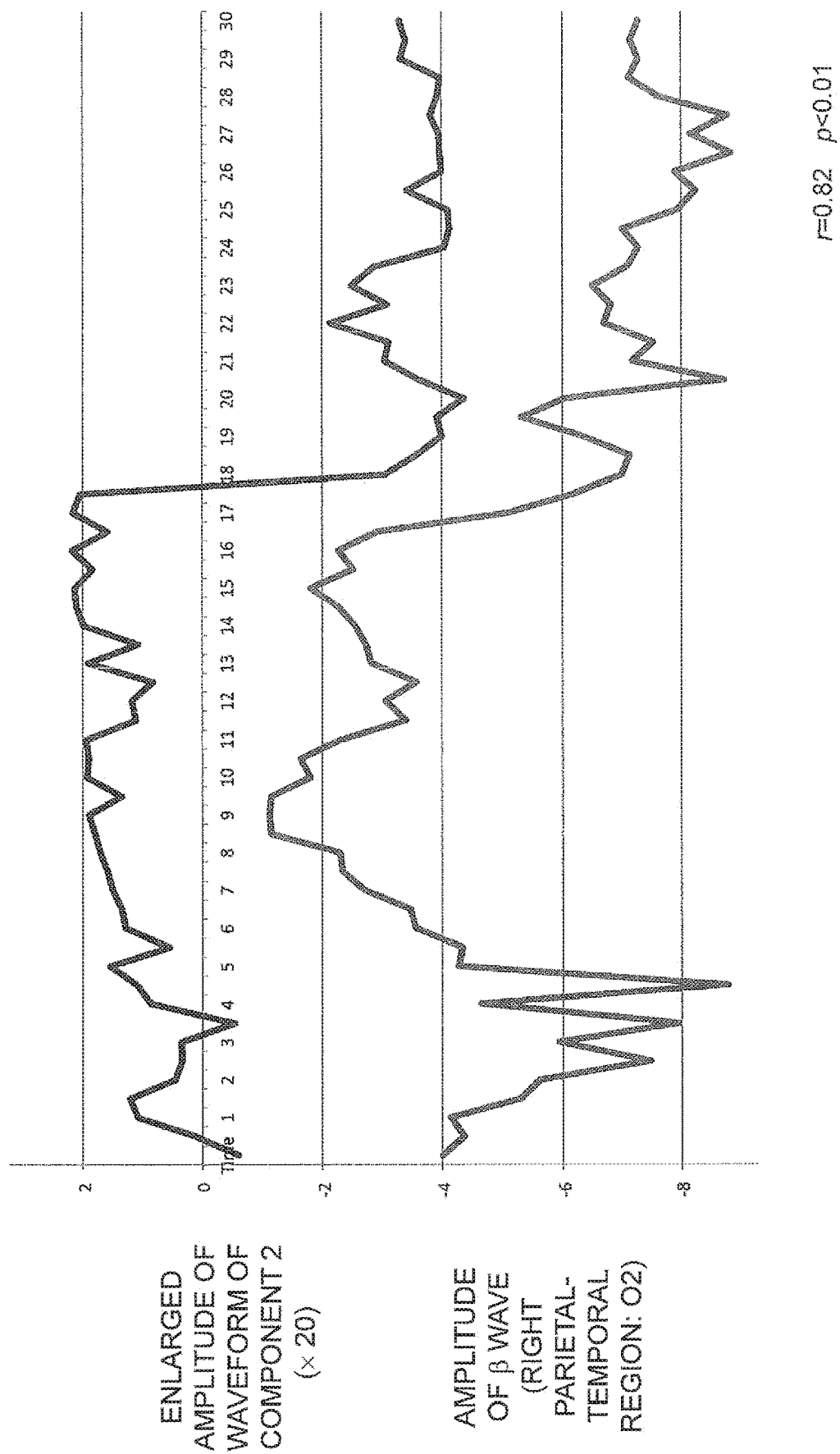
FIG. 9 is a diagram illustrating a component waveform based on captured image data of a face and the amplitude of the β wave among measured brain waves.
Figure 10:
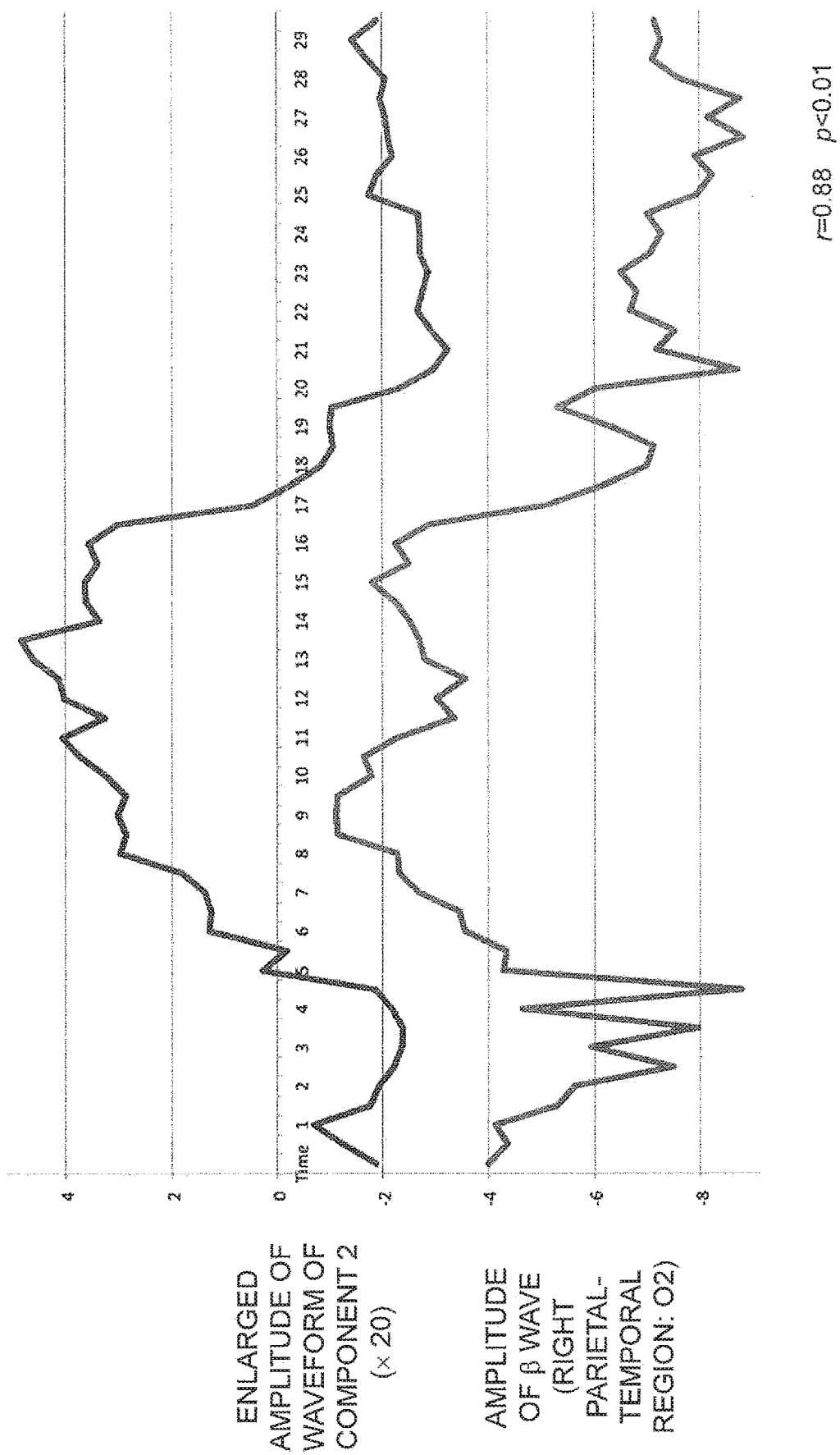
FIG. 10 is a diagram illustrating a component waveform based on facial skin temperature data and the amplitude of the β wave among measured brain waves.
Figure 11:
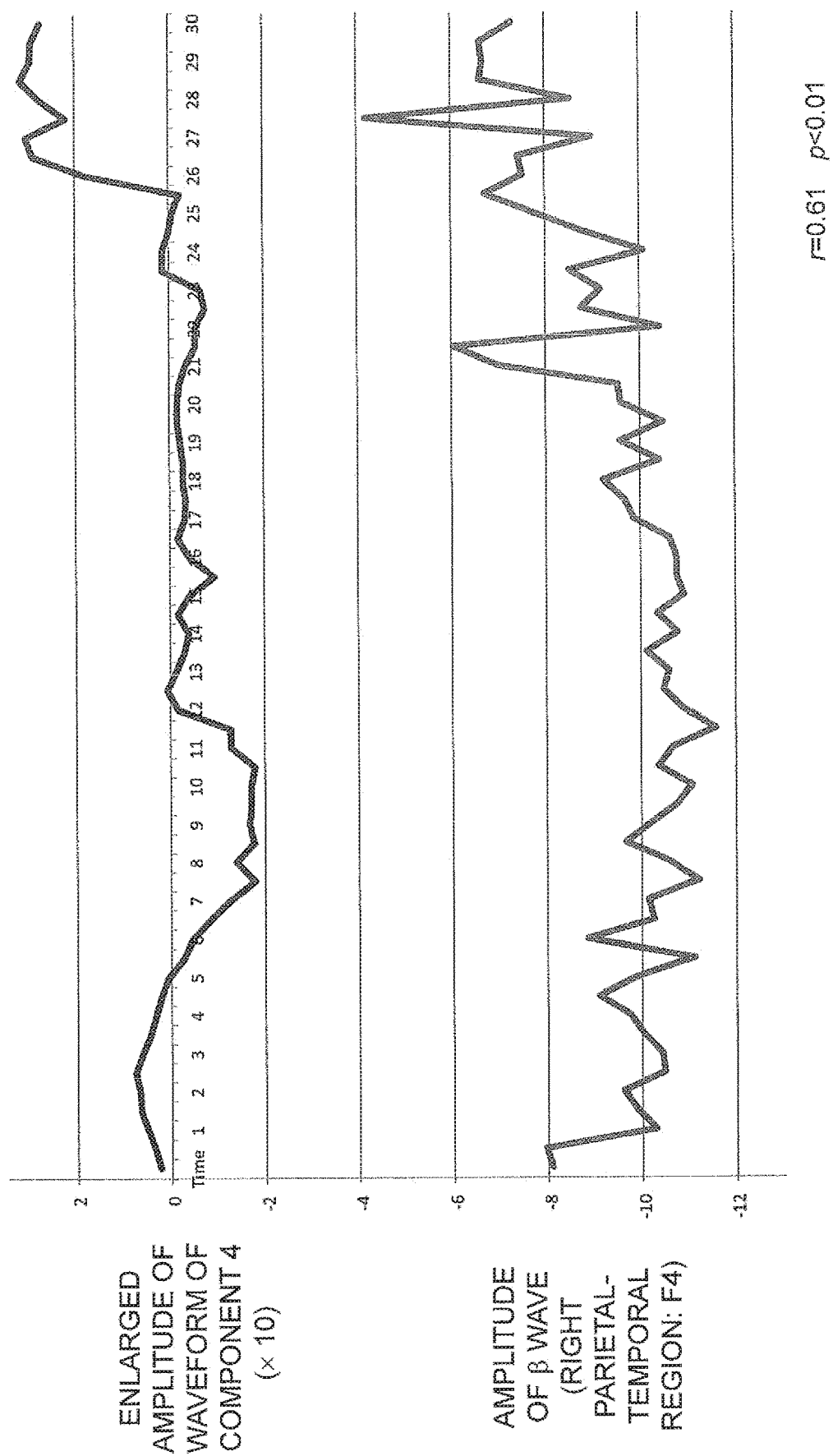
FIG. 11 is a diagram illustrating a component waveform based on captured image data of a face and the amplitude of the β wave among measured brain waves.
Figure 12:
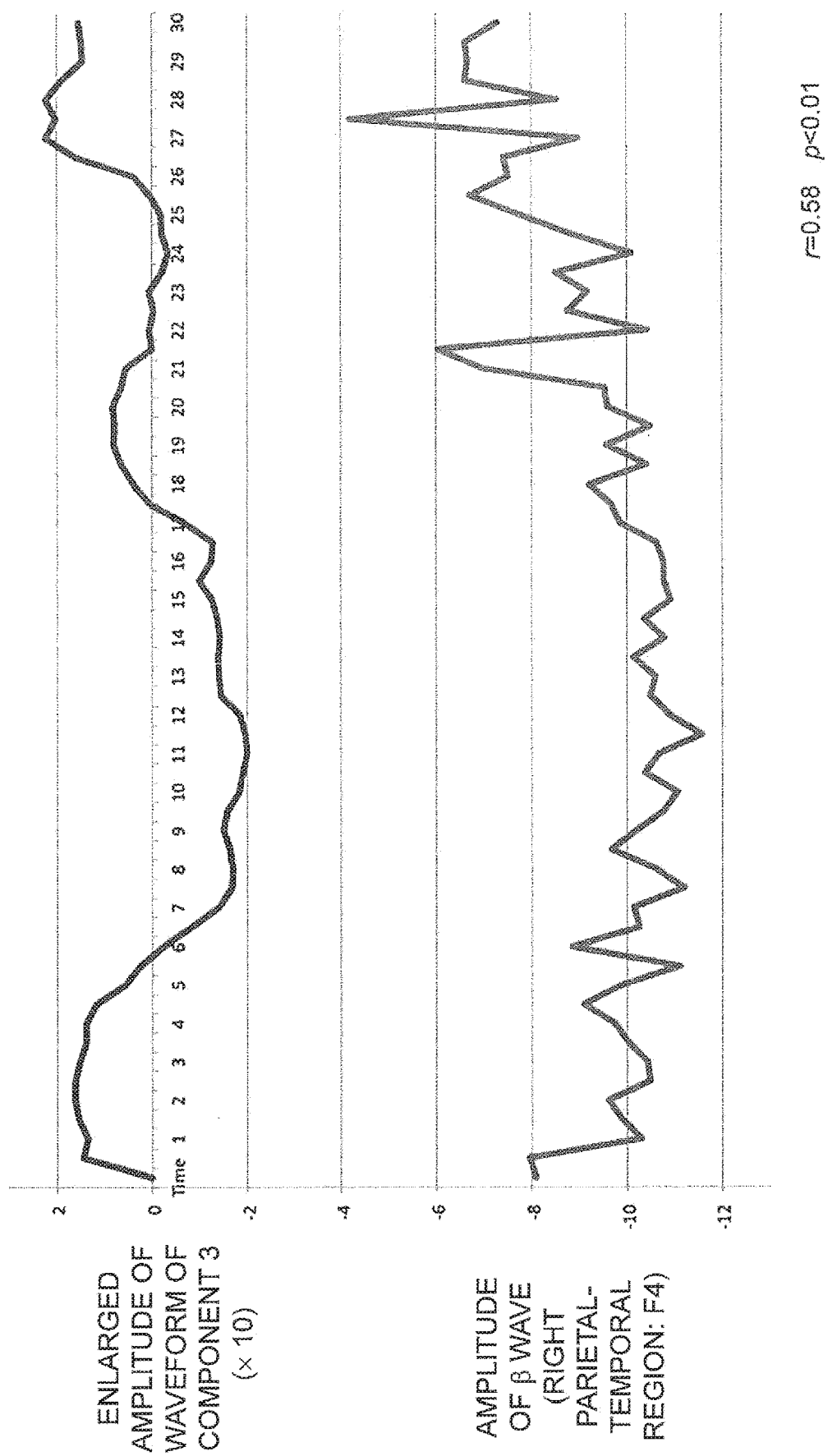
FIG. 12 is a diagram illustrating a component waveform based on facial skin temperature data and the amplitude of the β wave among measured brain waves.
Figure 13:
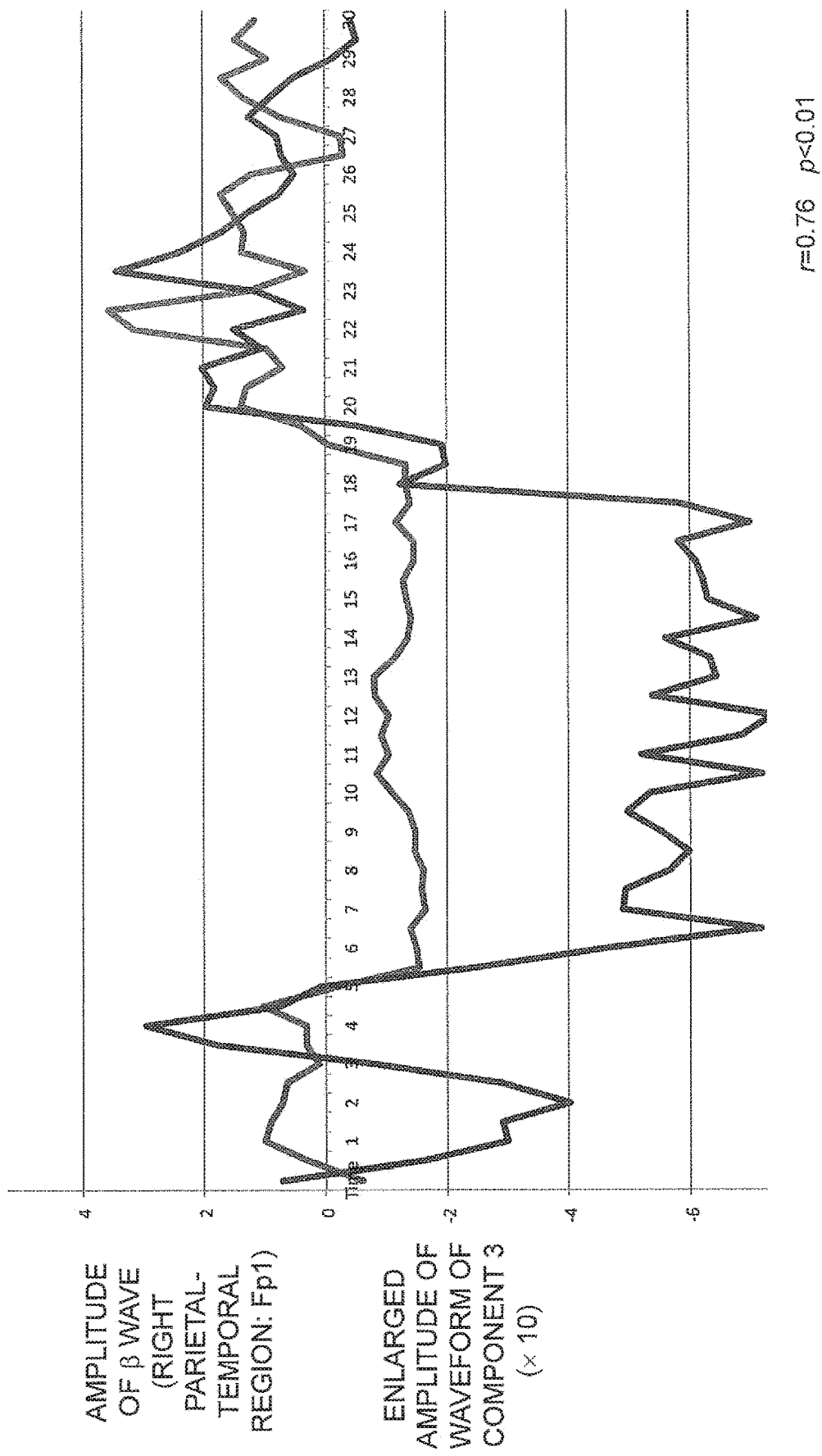
FIG. 13 is a diagram illustrating a component waveform based on captured image data of a face and the amplitude of the β wave among measured brain waves.
Figure 14:
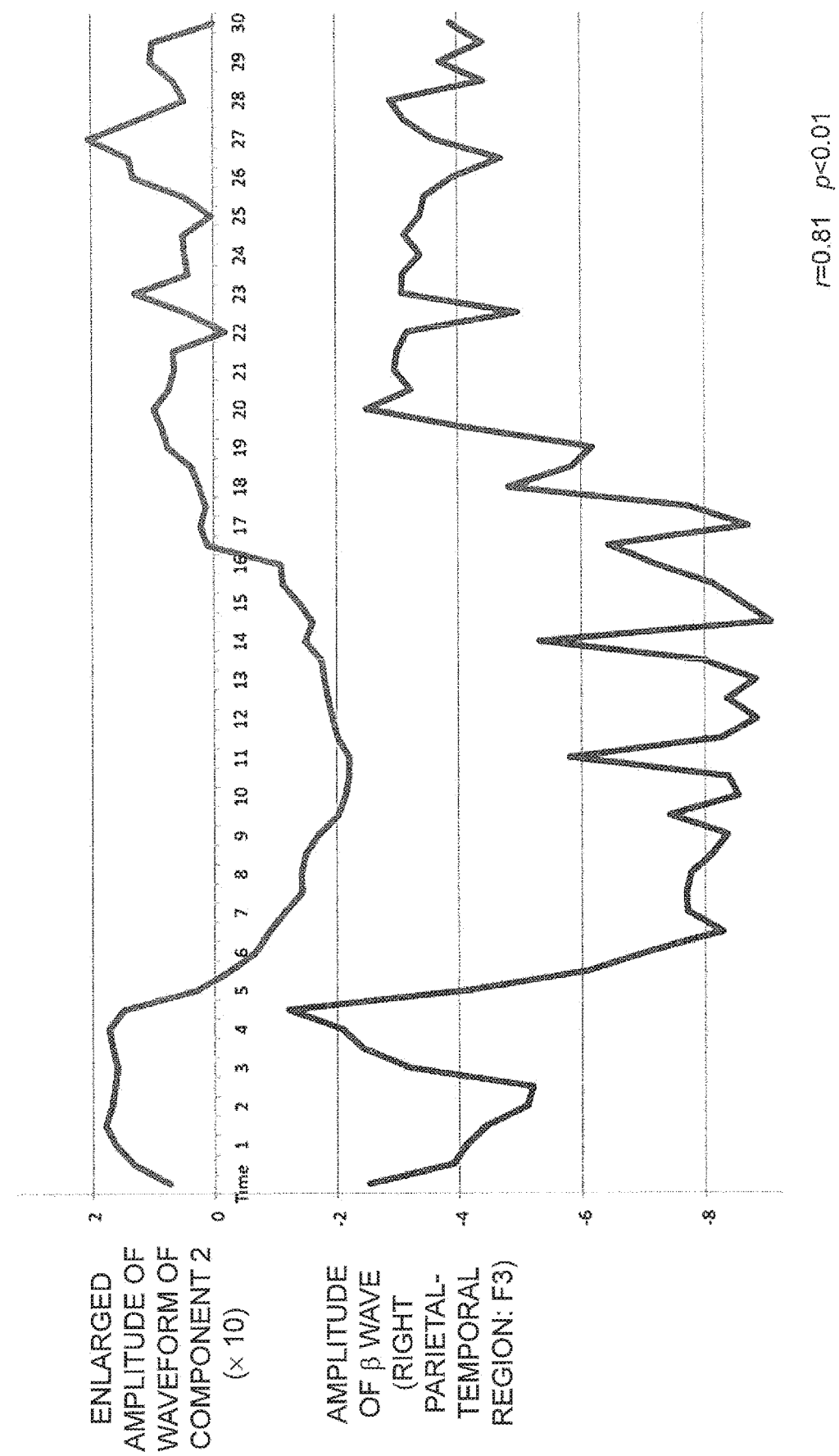
FIG. 14 is a diagram illustrating a component waveform based on facial skin temperature data and the amplitude of the β wave among measured brain waves.
Figure 15:
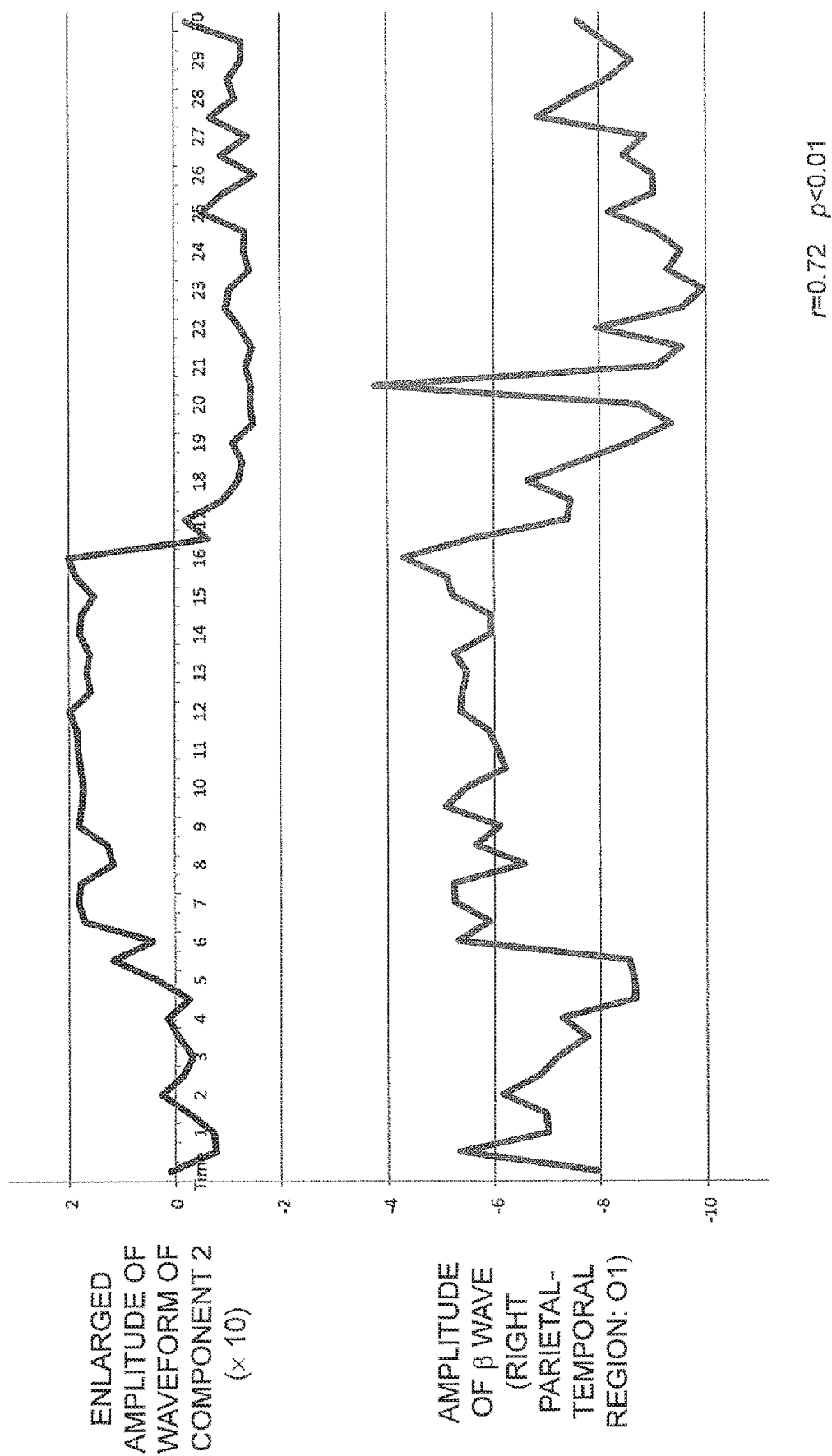
FIG. 15 is a diagram illustrating a component waveform based on captured image data of a face and the amplitude of the β wave among measured brain waves.
Figure 16:
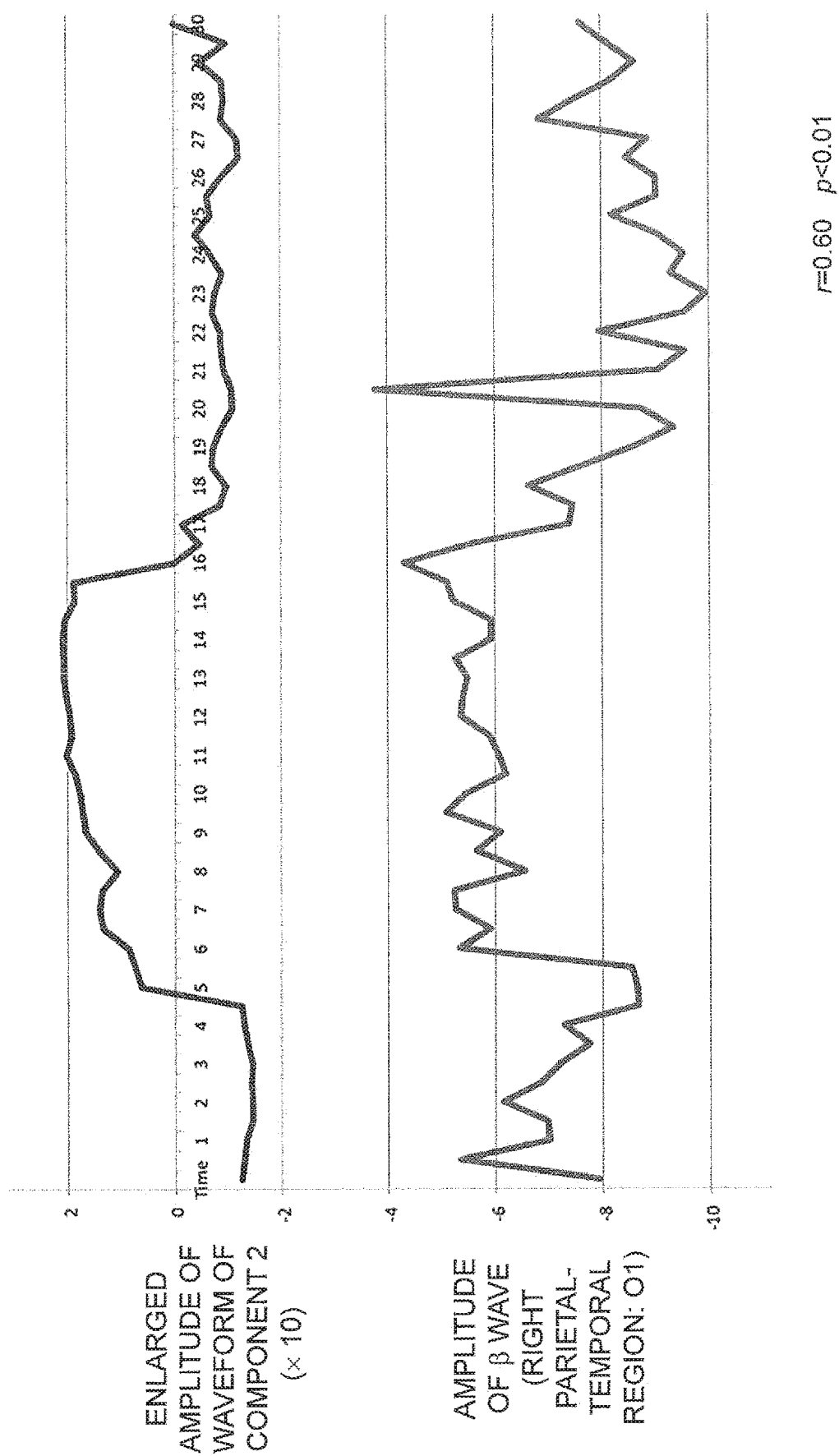
FIG. 16 is a diagram illustrating a component waveform based on facial skin temperature data and the amplitude of the β wave among measured brain waves.
Figure 17:
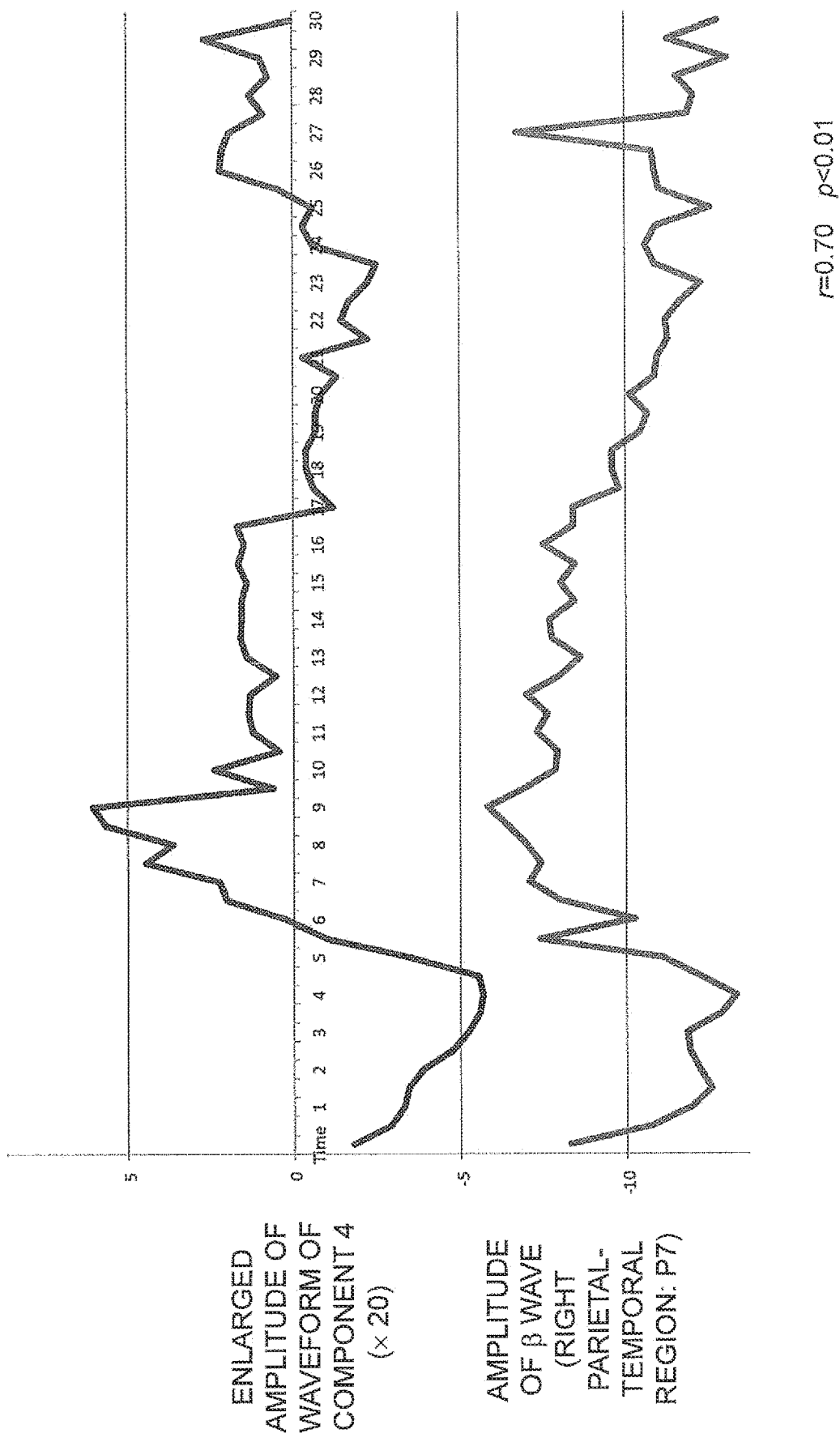
FIG. 17 is a diagram illustrating a component waveform based on captured image data of a face and the amplitude of the β wave among measured brain waves.
Figure 18:
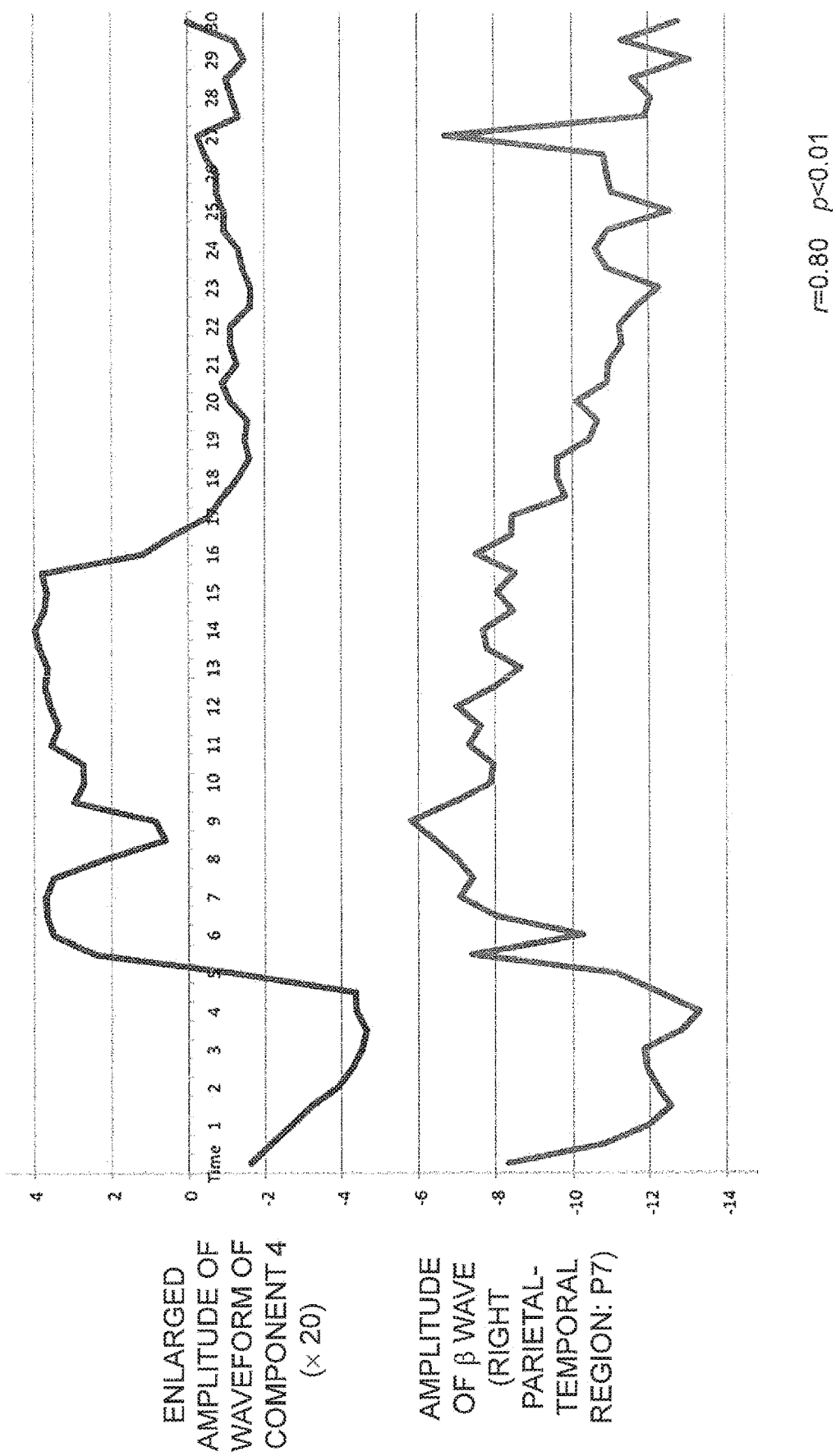
FIG. 18 is a diagram illustrating a component waveform based on facial skin temperature data and the amplitude of the β wave among measured brain waves.

FIGS. 7 to 18 are diagrams illustrating part of the result of comparing and analyzing component waveform diagrams based on captured face image data (blood-circulation-amount is data) or facial skin temperature data and waveform diagrams of the β wave among measured brain waves. FIG. 7 is a diagram illustrating the amplitude of the component waveform of the component 2 based on the captured image data of the test subject 1, and the amplitude of the β wave among the measured brain waves of the test subject 1. FIG. 8 is a diagram illustrating the amplitude of the component waveform of the component 2 based on the facial skin temperature data of the test subject 1, and the amplitude of the β wave among the measured brain waves of the test subject 1. FIG. 9 is a diagram illustrating the amplitude of the component waveform of the component 2 based on the captured image data of the test subject 2, and the amplitude of the β wave among the measured brain waves of the test subject 2. FIG. 10 is a diagram illustrating the amplitude of the component waveform of the component 2 based on the facial skin temperature data of the test subject 2, and the amplitude of the β wave among the measured brain waves of the test subject 2. FIG. 11 is a diagram illustrating the amplitude of the component waveform of component 4 based on the captured image data of the test subject 3, and the amplitude of the β wave among the measured brain waves of the test subject 3. FIG. 12 is a diagram illustrating the amplitude of the component waveform of the component 3 based on the facial skin temperature data of the test subject 3, and the amplitude of the β wave among the measured brain waves of the test subject 3. FIG. 13 is a diagram illustrating the amplitude of the component waveform of the component 3 based on the captured image data of the test subject 4, and the amplitude of the β wave among the measured brain waves of the test subject 4. FIG. 14 is a diagram illustrating the amplitude of the component waveform of the component 2 based on the facial skin temperature data of the test subject 4, and the amplitude of the β wave among the measured brain waves of the test subject 4. FIG. 15 is a diagram illustrating the amplitude of the component waveform of the component 2 based on the captured image data of the test subject 5, and the amplitude of the β wave among the measured brain waves of the test subject 5. FIG. 16 is a diagram illustrating the amplitude of the component waveform of the component 2 based on the facial skin temperature data of the test subject 5, and the amplitude of the β wave among the measured brain waves of the test subject 5. FIG. 17 is a diagram illustrating the amplitude of the component waveform of the component 4 based on the captured image data of the test subject 6, and the amplitude of the β wave among the measured brain waves of the test subject 6. FIG. 18 is a diagram illustrating the amplitude of the component waveform of the component 3 based on the facial skin temperature data of the test subject 6, and the amplitude of the β wave among the measured brain waves of the test subject 6.

As illustrated in FIGS. 7 to 18, the results of the component waveforms and brain wave analysis indicate correlation between the facial skin temperature and the amount of facial blood circulation. Also in the analysis based on both the facial skin temperature data and the facial blood-circulation-amount data, a significant correlation was found between the amplitude of each of the component waveforms and the amplitude of the β wave of the brain waves measured using electrodes attached to the parietal or occipital region.

Table 2 below shows analysis results of captured face image data of the test subjects.

TABLE 2

| | Correlation in Blood-Circulation-Amount Data | | Correlation in Relative Conversion Blood-Circulation-Amount Data | |
|---|---|---|---|---|
| Test Subject | Component waveform | Blood circulation amount distribution | Component waveform | Blood circulation amount distribution |
| Test Subject 1 | Component 2 | 0.72 | Component 1 | 0.59 |
| | | | Component 2 | 0.85 |
| Test Subject 2 | Component 1 | 0.82 | Component 1 | 0.62 |
| | Component 2 | 0.82 | Component 2 | 0.60 |
| Test Subject 3 | Component 2 | 0.33 | Component 2 | 0.45 |
| | Component 3 | 0.31 | Component 3 | 0.56 |
| | | | Component 4 | 0.56 |
| Test Subject 4 | Component 1 | 0.57 | Component 1 | 0.66 |
| | Component 3 | 0.71 | Component 3 | 0.65 |
| Test Subject 5 | Component 1 | 0.56 | Component 1 | 0.51 |
| | Component 2 | 0.72 | Component 2 | 0.83 |
| Test Subject 6 | Component 2 | 0.38 | Component 2 | 0.45 |
| | Component 4 | 0.68 | Component 3 | 0.51 |
| | | | Component 5 | 0.36 |

As shown in Table 2, the results obtained by the analysis of the captured face image data described above indicate significant correlation between human brain activity and the components 1, 2, 3, 4, and 5 among the plurality of components obtained by decomposing time-series blood-circulation-amount data based on the captured face image data by using the singular value decomposition. Here, not only a component found to have a significant correlation with human brain activity for both the correlation based on the blood-circulation-amount data and the correlation based on the relative conversion blood-circulation-amount data, but also a component found to have no significant correlation with human brain activity for the correlation based on the blood-circulation-amount data but found to have a significant correlation with human brain activity for the correlation based on the relative conversion blood-circulation-amount data is also recognized to have a significant correlation with human brain activity.

Table 3 below shows results of the contrast experiment.

TABLE 3

| | |
|---|---|
| Components having correlation with brain resting time/brain activation time | Component 1, Component 2 |
| Components having correlation with movement distance of face | Component 1, Component 3, Component 4 |
| Components having correlation with number of keyboard inputs | Component 8 |

As shown in Table 3, in the contrast experiment, when the test subject moves during the acquisition of captured face image data, the component 2 among components whose amplitudes of the component waveforms have a significant correlation with each of the brain deactivation time and the brain activation time was found to have no significant correlation with each of the movement distance and the number of keyboard inputs. This indicates that, among a plurality of components obtained by performing the singular value decomposition on the blood-circulation-amount data based on the RGB data acquired from the captured face image data, a component having a significant correlation with brain activity is affected much less by the movement of the test subject during the acquisition of time-series captured face image data, if any, than by the brain activities of the brain (than by the activation or deactivation of the brain).

From these results, the inventors have obtained the following findings.

As a result of decomposing the blood-circulation-amount data obtained from the facial RGB data based on the time-series captured face image data acquired from the test subject into a plurality of components by using the singular value decomposition and analyzing the components obtained through decomposition, the components 1, 2, 3, 4, and 5 among the plurality of components were found to be components related to brain activity. That is, the blood-circulation-amount data obtained from the facial RGB data based on the time-series captured face image data is decomposed into a plurality of components by using the singular value decomposition, a component having a correlation with the activation/deactivation of the brain is extracted from the plurality of components obtained through decomposition, and the extracted component is analyzed. Accordingly, it has turned out that a component indicating a facial RUB change reflecting brain activity can be identified from the plurality of components. From this, the inventors have obtained findings that brain activity can be estimated on the basis of time-series captured face image data of a person.

(4) Brain Activity Visualization Device

Next, brain activity visualization devices 10 and 110 according to an embodiment of the present invention, which has been achieved by the inventors on the basis of the findings described above, will be described. A brain activity visualization device according to the present invention is not limited to that in the following embodiment and may be modified as appropriate without departing from the scope of the invention.

The brain activity visualization devices 10 and 110 according to an embodiment of the present invention include a brain activity estimation means 30 for estimating brain activity on the basis of facial skin temperature data, and/or a brain activity estimation means 130 for estimating brain activity on the basis of captured face image data. In the following, before the description of the brain activity visualization devices 10 and 110 according to an embodiment of the present invention, the brain activity estimation means 30 and 130 will be described.

Figure 19:
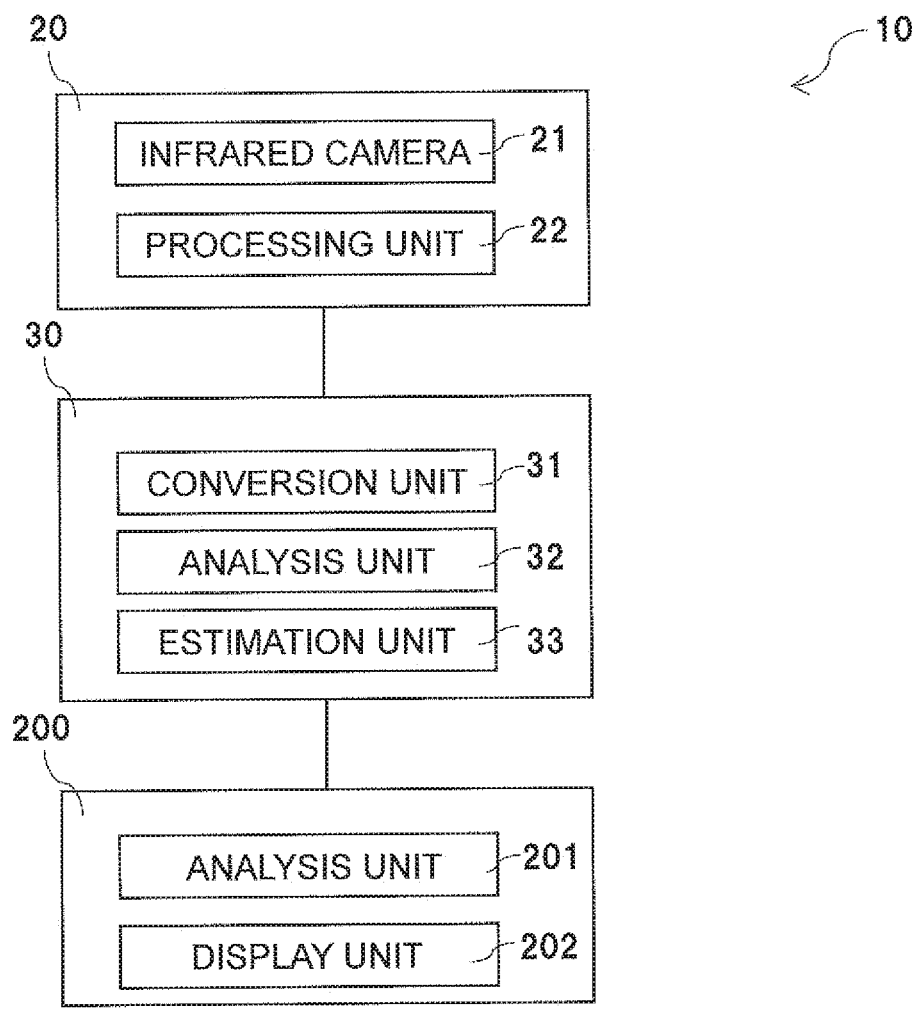
FIG. 19 is a diagrammatic illustration of a brain activity visualization device according to an embodiment of the present invention.
Figure 20:
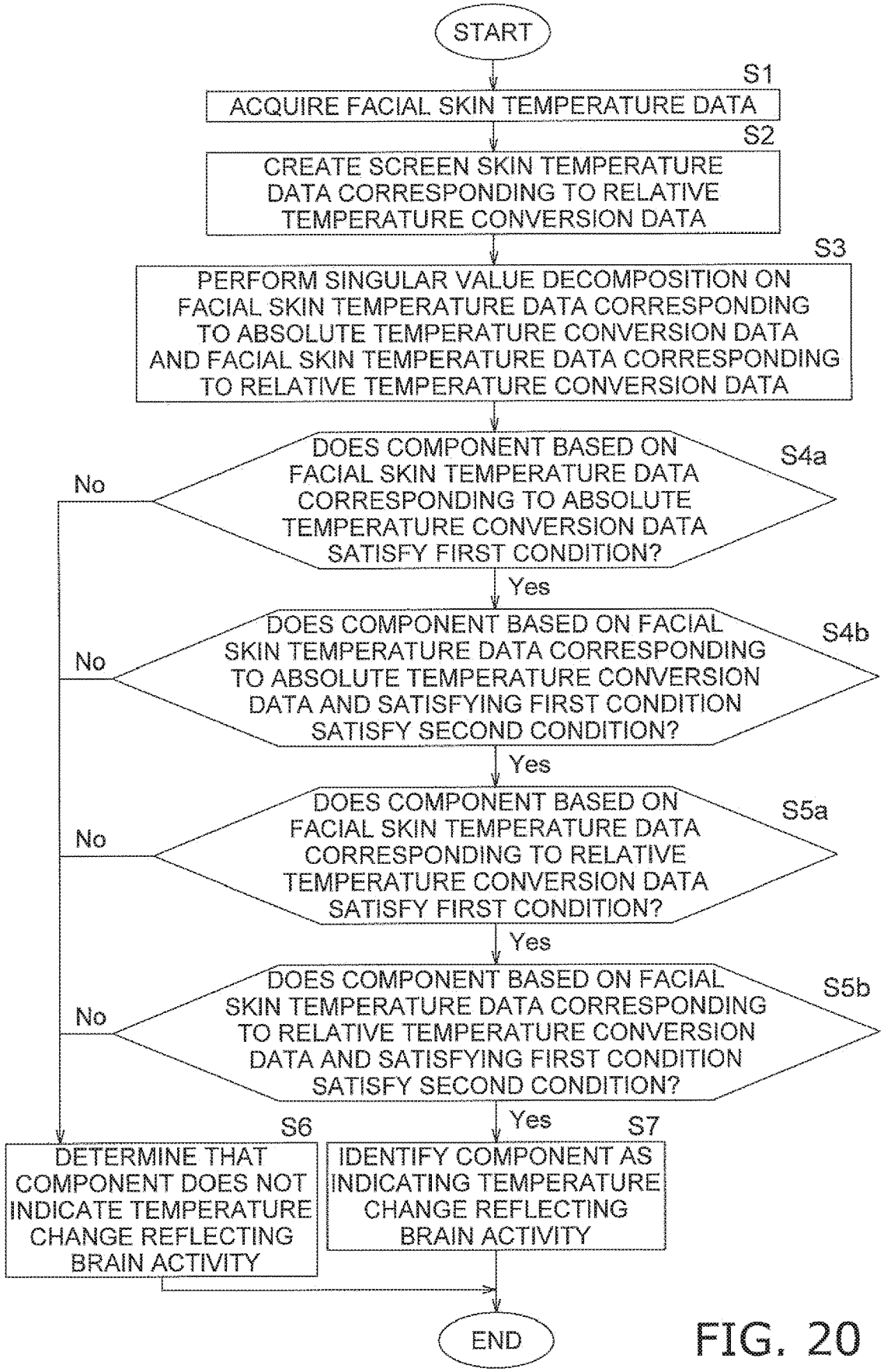
FIG. 20 is a flowchart illustrating an example of process flow in the brain activity visualization device to identify a component indicating a skin temperature change reflecting the brain function.

(4-1) Brain Activity Estimation Means 30 for Estimating Brain Activity on the Basis of Facial Skin Temperature Data FIG. 19 is a diagrammatic illustration of the brain activity visualization device 10 according to an embodiment of the present invention. FIG. 20 is a flowchart illustrating process flow in the brain activity visualization device 10 to identify a component indicating a skin temperature change reflecting the brain function.

The brain activity estimation means 30 of the brain activity visualization device 10 estimates the brain activity of a person (test subject) from the facial skin temperature of the person. As illustrated in FIG. 19, the brain activity visualization device 10 includes a facial skin temperature acquisition means 20, the brain activity estimation means 30, and a state visualization means 200.

The facial skin temperature acquisition means 20 detects the skin temperature of at least a portion of the face of a person and acquires in time series facial skin temperature data including the detected temperature data and location data of the detection region (step S1). Here, the facial skin temperature acquisition means 20 is an infrared thermography device. As illustrated in FIG. 19, the facial skin temperature acquisition means 20 includes an infrared camera 21 and a processing unit 22. The infrared camera 21 is used to detect infrared radiation energy emitted from the face of the person. The infrared camera 21 is assumed here to detect infrared radiation energy from the entire area of the face of the person. The processing unit 22 converts the infrared radiation energy detected by the infrared camera 21 into temperatures to generate temperature data, creates a temperature distribution diagram of facial skin temperatures on the entire area of the face in which a region where the infrared radiation energy has been detected is represented as location data (coordinate data), and processes the created temperature distribution diagram as facial skin temperature data corresponding to temperature conversion data. The facial skin temperature data corresponding to temperature conversion data is stored in a storage unit (not illustrated) included in the processing unit 22.

Here, the processing unit 22 creates a temperature distribution diagram of facial skin temperatures on the entire area of the face. However, this is not limiting. A temperature distribution diagram of facial skin temperatures including the temperatures of at least the paranasal-sinus surrounding area and/or the forehead portion may be created and used as facial skin temperature data corresponding to temperature conversion data.

In addition, while the facial skin temperature acquisition means 20 acquires facial skin temperature data corresponding to temperature conversion data, the person is presented with a brain function activation exercise for a certain period. That is, the facial skin temperature data corresponding to temperature conversion data, which is acquired by the facial skin temperature acquisition means 20, includes data obtained in a period during which the brain function activation exercise is presented to the person. The brain function activation exercise presented to the person is not specifically limited, and may be any exercise estimated to activate the brain. For example, the content of the brain function activation exercise may be determined as desired according to the purpose of use of the brain activity visualization device 10.

The brain activity estimation means 30 estimates human brain activity on the basis of the facial skin temperature data corresponding to temperature conversion data, which is acquired by the facial skin temperature acquisition means 20. Specifically, as illustrated in FIG. 19, the brain activity estimation means 30 includes a conversion unit 31, an analysis unit 32, and an estimation unit 33.

The conversion unit 31 converts the temperature data included in the facial skin temperature data corresponding to temperature conversion data into relative temperature data and creates facial skin temperature data based on the converted relative temperature data, that is, facial skin temperature data corresponding to relative temperature conversion data (step S2). Specifically, the conversion unit 31 converts temperature data included in facial skin temperature data corresponding to temperature conversion data obtained at intervals of a predetermined time (e.g., 30 seconds) into relative temperature data by using the average value of the temperature data as a reference value. Then, the conversion unit 31 creates facial skin temperature data corresponding to relative temperature conversion data by utilizing the converted relative temperature data and the location data.

The analysis unit 32 decomposes each of the facial skin temperature data corresponding to time-series temperature conversion data and the facial skin temperature data corresponding to relative temperature conversion data into a plurality of components by using singular value decomposition, principal component analysis, or independent component analysis (step S3). Here, the analysis unit 32 performs the singular value decomposition on each of the facial skin temperature data corresponding to the acquired temperature conversion data and the facial skin temperature data corresponding to the converted relative temperature conversion data by using SVD of MATLAB (registered trademark) as an analysis tool. The singular value decomposition is performed on the facial skin temperature data corresponding to temperature conversion data acquired in time series and the facial skin temperature data corresponding to relative temperature conversion data, in which the factor is time data obtained at intervals of a predetermined period (e.g., 30 seconds) and the measure is the facial skin temperature data corresponding to temperature conversion data within the period and the facial skin temperature data corresponding to relative temperature conversion data. Through the singular value decomposition, each of the facial skin temperature data corresponding to temperature conversion data and the facial skin temperature data corresponding to relative temperature conversion data is decomposed into a plurality of components, and a temporal distribution, a spatial distribution, and a singular value indicating the magnitude of each component are calculated.

Further, the analysis unit 32 determines whether each component satisfies a first condition and a second condition to identify a component indicating a skin temperature change reflecting brain activity from the plurality of components obtained through decomposition using the singular value decomposition (steps S4a, S4b, S5a, and S5b). The analysis unit 32 first determines whether each component based on the facial skin temperature data corresponding to temperature conversion data satisfies the first condition (step S4a), and determines whether a component based on the facial skin temperature data corresponding to temperature conversion data that is determined in step S4a to satisfy the first condition satisfies the second condition (step S4b). Then, the analysis unit 32 focuses only on a component matching the component determined in steps S4a and S4b to satisfy the first condition and the second condition among the components based on the facial skin temperature data corresponding to relative temperature conversion data, and determines whether this component satisfies the first condition (step S5a). Thereafter, the analysis unit 32 determines whether a component based on the facial skin temperature data corresponding to relative temperature conversion data that is determined in step S5a to satisfy the first condition satisfies the second condition (step S5b). However, the order of the determination performed by the analysis unit 32 is not limited to that described above. For example, it may be determined whether the components based on the facial skin temperature data corresponding to temperature conversion data and the components based on the facial skin temperature data corresponding to relative temperature conversion data each satisfy the first condition and the second condition, and a component for which the determination results match may be finally extracted.

The first condition is a condition in which the amplitude of the component waveform of a component obtained through decomposition using the singular value decomposition has a correlation with changes during the brain deactivation time and the brain activation time. The analysis unit 32 extracts as a determination component a component satisfying the first condition from among the plurality of components. During the acquisition of the facial skin temperature data corresponding to temperature conversion data, a brain function activation exercise is presented to a person for a certain period. The analysis unit 32 compares and analyzes the component waveform of each component and each of the period during which the brain function activation exercise is presented and the period during which no brain function activation exercise is presented, where the period during which no brain function activation exercise is presented to the person is defined as the brain deactivation time and the period during which the brain function activation exercise is presented to the person is defined as the brain activation time. The analysis unit 32 evaluates whether a correlation exists between the component waveform of each component and each of the brain deactivation time and the brain activation time by utilizing comparison and analysis results based on the component waveform data, and extracts a component evaluated to have a correlation with each of the brain deactivation time and the brain activation time among the plurality of components as a determination component satisfying the first condition. On the other hand, the analysis unit 32 determines that a component evaluated to have no correlation with each of the brain deactivation time and the brain activation time among the plurality of components does not satisfy the first condition and is not a component indicating a temperature change reflecting human brain activity (step S6).

Here, a person is presented with a brain function activation exercise for a certain period during the acquisition of the facial skin temperature data corresponding to temperature conversion data, and the analysis unit 32 extracts a determination component accordingly. However, the content of the first condition, that is, the determination component extraction means in the analysis unit 32, is not limited thereto. For example, if a component exhibiting a component waveform having a correlation with the brain deactivation time and the brain activation time is identified from the plurality of components by experiment or the like conducted in advance, the analysis unit 32 extracts the identified component from the plurality of components as a determination component. When a human movement known to be related to the activation/inactivation of the brain, such as eye movement or blinking is detected in this brain activity visualization device, the analysis unit 32 may compare, analyze, and evaluate the detection result and the component waveform of each component to extract a determination component from the plurality of components. The criterion by which the analysis unit 32 determines whether the first condition is satisfied is determined, as appropriate, by simulation, experiment, desktop calculations, or the like according to the purpose of use or the like of the brain activity visualization device 10.

The second condition is a condition in which temperature changes in a predetermined region on the human face for the extracted determination component. The analysis unit 32 determines that a component that is the determination component and that satisfies the second condition is likely to be related to human brain activity, and extracts the component as a candidate component. That is, the analysis unit 32 determines whether the determination component is related to human brain activity on the basis of the presence of a temperature change in a predetermined region on the human face, Specifically, the analysis unit 32 determines whether a temperature change has occurred in the paranasal-sinus surrounding area and/or the forehead portion on the basis of temperature distribution data of the extracted determination component. If a temperature change has occurred, the determination component is determined to satisfy the second condition and to be a component that is likely to be related to human brain activity, and is extracted as a candidate component. On the other hand, no temperature change has occurred in the paranasal-sinus surrounding area and/or the forehead portion, the analysis unit 32 determines that the determination component does not satisfy the second condition and is not a component indicating a skin temperature change reflecting brain activity (step S6). The criterion by which the analysis unit 32 determines whether the second condition is satisfied is determined, as appropriate, by simulation, experiment, desktop calculations, or the like according to the purpose of use or the like of the brain activity visualization device 10.

Then, the analysis unit 32 identifies the component determined in step S5b to satisfy the second condition as a component indicating a skin temperature change reflecting brain activity (step S7). That is, the component identified in step S7 as a component indicating a skin temperature change reflecting brain activity is a component that realizes that a match is found between the candidate component extracted by decomposing the facial skin temperature data corresponding to temperature conversion data by using the singular value decomposition and performing analysis and the candidate component extracted by decomposing the facial skin temperature data corresponding to relative temperature conversion data by using the singular value decomposition and performing analysis. Candidate components that do not match in both analyses are each determined in step S6 not to be a component indicating a skin temperature change reflecting brain activity.

The estimation unit 33 estimates human brain activity on the basis of the component identified by the analysis unit 32 as a component indicating a skin temperature change reflecting human brain activity. Specifically, the estimation unit 33 estimates the amount of brain activity during the acquisition of the facial skin temperature data on the basis of the component waveform data of the component identified by the analysis unit 32.

(4-1-1) Modification 1A

The brain activity estimation means 30 described above includes the conversion unit 31, and the conversion unit 31 creates facial skin temperature data corresponding to relative temperature conversion data. Then, the analysis unit 32 decomposes not only the facial skin temperature data corresponding to temperature conversion data, which is acquired by the facial skin temperature acquisition means 20, but also facial skin temperature data corresponding to relative temperature data based on temperature data converted to relative temperature data into a plurality of components by using the singular value decomposition, and analyzes each of the components.

Alternatively, the brain activity estimation means 30 may not include the conversion unit 31. In this case, the process of creating facial skin temperature data corresponding to relative temperature conversion data and analyzing data based on the facial skin temperature data corresponding to relative temperature conversion data may be omitted.

However, to accurately identify a component related to human brain activity, as in the embodiment described above, it is desirable that the brain activity estimation means 30 include the conversion unit 31 and that the analysis unit 32 decompose not only the facial skin temperature data corresponding to temperature conversion data, which is acquired by the facial skin temperature acquisition means 20, but also facial skin temperature data corresponding to relative temperature data based on temperature data converted to relative temperature data into a plurality of components by using the singular value decomposition and analyze each of the components.

(4-1-2) Modification 1B

The facial skin temperature acquisition means 20 described above is an infrared thermography device capable of acquiring temperature data in non-contact with a target object.

However, the facial skin temperature acquisition means is not limited to an infrared thermography device if it is capable of detecting the skin temperature of at least a portion of the face of a person and acquiring in time series facial skin temperature data including the detected temperature data and location data of the detection region.

For example, the facial skin temperature acquisition means may be a device including a temperature sensor. Specifically, a temperature sensor may be attached to a predetermined region on the face of a person, and time-series facial skin temperature data may be acquired on the basis of temperature data detected by the temperature sensor and on the basis of location data of the region to which the temperature sensor is attached. In this way, even when facial skin temperature data is acquired using a temperature sensor in contact with a target person, unlike electroencephalogram electrodes or the like, the temperature sensor, which does not require processing before attachment, can acquire data more easily than existing detection methods such as electroencephalography, magnetic resonance imaging, and near-infrared spectroscopy. This can facilitate estimation of human brain activity.

Figure 21:
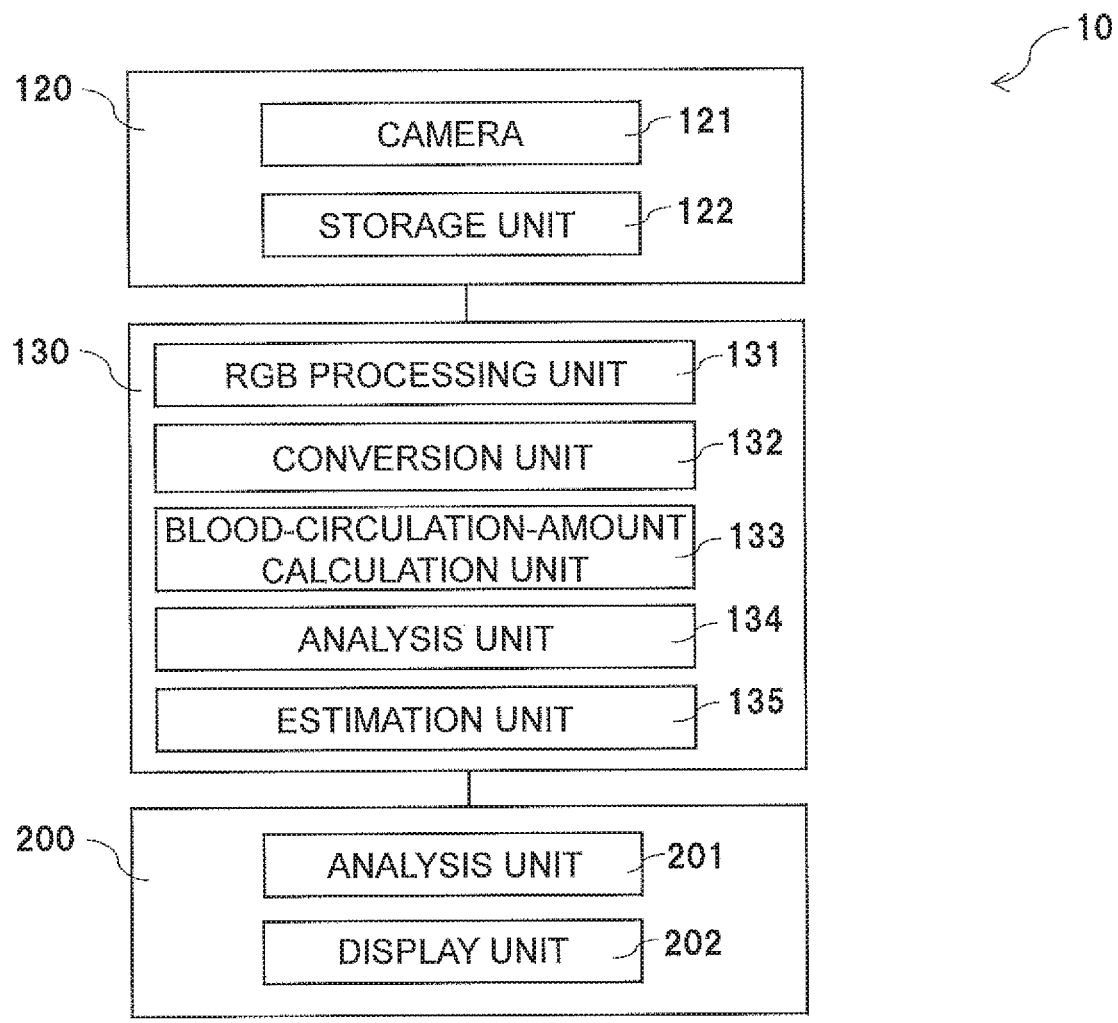
FIG. 21 is a diagrammatic illustration of a brain activity visualization device according to an embodiment of the present invention.
Figure 22:
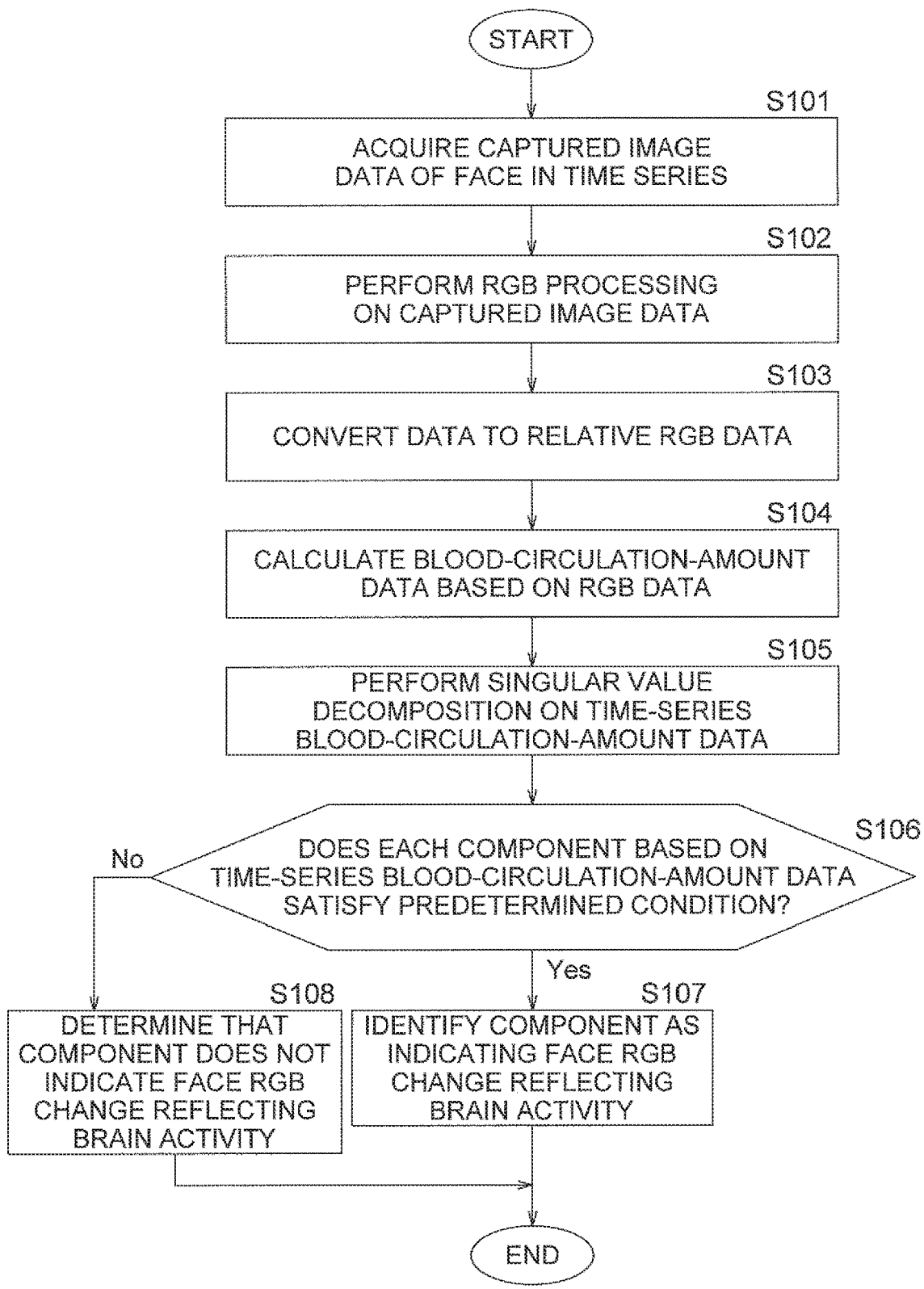
FIG. 22 is a flowchart illustrating an example of process flow in the brain activity visualization device to identify a component indicating a face RGB change reflecting the brain function.

(4-2) Brain Activity Estimation Means 130 for Estimating Brain Activity on the Basis of Captured Face Image Data FIG. 21 is a diagrammatic illustration of the brain activity visualization device 110 according to an embodiment of the present invention. FIG. 22 is a flowchart illustrating an example of process flow in the brain activity visualization device 110 to identify a component indicating a face RGB change reflecting the brain function.

The brain activity estimation means 130 of the brain activity visualization device 110 is a device for estimating the brain activity of a person (test subject) from captured face image data of the person. As illustrated in FIG. 21, the brain activity visualization device 110 includes an image data acquisition means 120, the brain activity estimation means 130, and the state visualization means 200.

The image data acquisition means 120 acquires captured image data of at least a portion of the face of a person in time series (step S101). The image data acquisition means 120 is not limited if it includes at least an imaging device. Examples of the image data acquisition means 120 include portable terminals including an imaging device, such as a smartphone and a tablet (e.g., iPad: registered trademark). As illustrated in FIG. 21, the image data acquisition means 120 includes a camera 121 serving as an imaging device, and a storage unit 122. The camera 121 is used to acquire captured face image data of the person in time series. Here, the camera 121 captures a moving image of the entire area of the face of the person and acquires captured moving image data. The storage unit 122 stores time-series captured image data captured by the imaging device. Here, the storage unit 122 stores the moving image data acquired by the camera 121.

The camera 121 captures a moving image of the entire area of the face, which is not limiting. The camera 121 may capture a moving image including at least images of the forehead portion and/or the paranasal-sinus surrounding area of the face.

In addition, while the image data acquisition means 120 acquires time-series captured face image data, the person is presented with a brain function activation exercise for a certain period. That is, the captured image data acquired by the image data acquisition means 120 includes data obtained in a period during which the brain function activation exercise is presented to the person. The brain function activation exercise presented to the person is not specifically limited, and may be any exercise estimated to activate the brain. For example, the content of the brain function activation exercise may be determined as desired according to the purpose of use of the brain activity visualization device 110.

The brain activity estimation means 130 estimates human brain activity on the basis of the time-series captured face image data acquired by the image data acquisition means 120. Specifically, as illustrated in FIG. 21, the brain activity estimation means 130 includes an RGB processing unit 131, a conversion unit 132, a blood-circulation-amount calculation unit 133, an analysis unit 134, and an estimation unit 135. In FIG. 21, the brain activity estimation means 130 is illustrated as a single device including the RGB processing unit 131, the conversion unit 132, the blood-circulation-amount calculation unit 133, the analysis unit 134, and the estimation unit 135. However, the present invention is not limited to this, and some or each of the RGB processing unit 131, the conversion unit 132, the blood-circulation-amount calculation unit 133, the analysis unit 134, and the estimation unit 135 may be present as an independent device. Further, the image data acquisition means 120, the RGB processing unit 131, the conversion unit 132, and the blood-circulation-amount calculation unit 133 constitute a facial blood-circulation-amount acquisition means.

The RGB processing unit 131 performs RGB processing to decompose the captured image data acquired by the image data acquisition means 120 into three color components: an R component, a G component, and a B component (step S102). While RGB processing may be performed on captured image data of the entire area of the face, to reduce the amount of computation processing and noise, data of the forehead portion and/or the paranasal-sinus surrounding area is extracted from the captured image data, and only the extracted data is subjected to RGB processing.

The conversion unit 132 converts the RGB data of the captured image data obtained through RGB processing into relative RGB data (step S103). Specifically, the conversion unit 132 converts RGB data obtained from the captured image data acquired at intervals of a predetermined time (e.g., 30 seconds) into relative RGB data by using the average value of the RGB data as a reference value.

The blood-circulation-amount calculation unit 133 calculates time-series facial blood-circulation-amount data on the basis of the RGB data of the captured image data obtained through RGB processing (step S104).

The analysis unit 134 decomposes the time-series relative conversion blood-circulation-amount data into a plurality of components by using singular value decomposition, principal component analysis, or independent component analysis (step S105). Here, the analysis unit 134 performs the singular value decomposition on the relative conversion blood-circulation-amount data by using SVD of MATLAB (registered trademark) as an analysis tool. Specifically, the singular value decomposition is performed on the time-series relative conversion blood-circulation-amount data, in which the factor is time data obtained at intervals of a predetermined period (e.g., 30 seconds) and the measure is per-pixel relative conversion blood-circulation-amount data computed from relative RGB data within the period. Through the singular value decomposition, the time-series relative conversion blood-circulation-amount data is decomposed into a plurality of components, and a temporal distribution, a spatial distribution, and a singular value indicating the magnitude of each component are calculated.

Further, the analysis unit 134 determines whether each component satisfies a predetermined condition to identify a component indicating a facial RGB change reflecting brain activity from the plurality of components obtained through decomposition using the singular value decomposition (step S106), Examples of the predetermined condition include a condition in which the amplitude of the component waveform of a component obtained through decomposition using the singular value decomposition has a correlation with changes during the brain deactivation time and the brain activation time (hereinafter referred to as first condition), and a condition in which a change in the amount of blood circulation changes in a predetermined region on the human face for a component obtained through decomposition using the singular value decomposition (hereinafter referred to as second condition). One or more conditions may be set as the predetermined condition on which the determination performed by the analysis unit 134 is based. Here, the first condition is set as the predetermined condition.

Then, the analysis unit 134 extracts a component satisfying the predetermined condition from the plurality of components as a determination component. Further, the analysis unit 134 identifies a component that is an extracted determination component and that satisfies all the conditions included in the predetermined condition as a component indicating a face RGB change reflecting brain activity (step S107). On the other hand, the analysis unit 134 determines that a component determined not to satisfy at least one of the conditions included in the predetermined condition among the plurality of components is not a component indicating a facial RGB change reflecting brain activity (step S108).

As described above, only one condition (the first condition) is set as the predetermined condition, and a brain function activation exercise is presented to the person for a certain period during the acquisition of time-series captured face image data. Accordingly, the analysis unit 134 compares and analyzes the component waveform of each component and each of the period during which the brain function activation exercise is presented and the period during which no brain function activation exercise is presented, where the period during which no brain function activation exercise is presented to the person is defined as the brain deactivation time and the period during which the brain function activation exercise is presented to the person is defined as the brain activation time. Then, the analysis unit 134 evaluates whether a correlation exists between the component waveform of each component and each of the brain deactivation time and the brain activation time by utilizing comparison and analysis results based on the component waveform data, and extracts a component evaluated to have a correlation with each of the brain deactivation time and the brain activation time among the plurality of components as a determination component satisfying the predetermined condition. Also, the analysis unit 134 identifies the extracted component as a component indicating a facial RGB change reflecting brain activity. On the other hand, the analysis unit 134 determines that a component evaluated to have no correlation with each of the brain deactivation time and the brain activation time among the plurality of components does not satisfy the predetermined condition and is not a component indicating a facial RGB change reflecting human brain activity.

Here, a person is presented with a brain function activation exercise for a certain period during the acquisition of time-series captured face image data, and the analysis unit 134 extracts a determination component accordingly. However, the content of the first condition, that is, the determination component extraction means in the analysis unit 134, is not limited thereto. For example, if a component exhibiting a component waveform having a correlation with the brain deactivation time and the brain activation time is identified from the plurality of components by experiment or the like conducted in advance, the analysis unit 134 extracts the identified component from the plurality of components as a determination component. When a human movement known to be related to the activation/inactivation of the brain, such as eye movement or blinking, is also detected in the brain activity visualization device 110, the analysis unit 134 may compare, analyze, and evaluate the detection result and the component waveform of each component to extract a determination component from the plurality of components. The criterion by which the analysis unit 134 determines whether the first condition is satisfied is determined, as appropriate, by simulation, experiment, desktop calculations, or the like according to the purpose of use or the like of the brain activity visualization device 110.

When the second condition is set as the predetermined condition, the analysis unit 134 extracts a determination component on the basis of the presence of a change in the amount of facial blood circulation in a predetermined region on the human face. Specifically, the analysis unit 134 determines whether a change in the amount of blood circulation has occurred in the paranasal-sinus surrounding area and/or the forehead portion on the basis of blood circulation amount distribution diagrams corresponding to the plurality of components obtained by decomposition using the singular value decomposition. If a change in the amount of blood circulation has occurred, the analysis unit 134 determines that the component satisfies the second condition. On the other hand, if no change in the amount of blood circulation has occurred in the paranasal-sinus surrounding area and/or the forehead portion, the analysis unit 134 determines that the component does not satisfy the second condition. The criterion by which the analysis unit 134 determines whether the second condition is satisfied is determined, as appropriate, by simulation, experiment, desktop calculations, or the like according to the purpose of use or the like of the brain activity visualization device 110.

If the blood-circulation-amount calculation unit 133 calculates time-series blood-circulation-amount data based on RGB data obtained before conversion to the relative RGB data, the analysis unit 134 may also determine whether each of the plurality of components obtained by performing the singular value decomposition or the like on the blood-circulation-amount data satisfies the first condition and/or the second condition, and extract a determination component.

The estimation unit 135 estimates human brain activity on the basis of the component identified by the analysis unit 134 as a component indicating a facial RGB change reflecting human brain activity. Specifically, the estimation unit 135 estimates the amount of brain activity during the acquisition of captured face image data on the basis of the component waveform data of the component identified by the analysis unit 134.

(4-2-1) Modification 2A

As described above, a portable terminal including an imaging device, such as a smartphone or a tablet (e.g., iPad: registered trademark), may be used as the camera 121. That is, the captured image data described above may be obtained by capturing an image of a visible light area.

The blood-circulation-amount calculation unit 133 described above may calculate facial blood-circulation-amount data by using, mainly, the R component among the pixels included in RGB data. The blood-circulation-amount data is not necessarily limited to an erythema index if blood-circulation-amount data can be calculated on the basis of RGB data.

(4-2-2) Modification 2B

The blood-circulation-amount calculation unit 133 described above calculates relative conversion blood-circulation-amount data on the basis of the relative RGB data converted by the conversion unit 132. Alternatively or additionally, blood-circulation-amount data may be calculated on the basis of the RGB data obtained before conversion to the relative RGB data. In the blood-circulation-amount data calculated on the basis of the RGB data obtained before conversion to the relative RGB data, a component having a correlation with brain activity is likely to appear (verified with high performance). Accordingly, for example, the blood-circulation-amount data calculated on the basis of the RGB data obtained before conversion to the relative RGB data may be analyzed prior to the relative conversion blood-circulation-amount data calculated on the basis of relative RGB data. In addition, for example, first, the blood-circulation-amount data may be analyzed to extract a component having a significant correlation, and, for the relative conversion blood-circulation-amount data, only the component corresponding to the extracted component may be analyzed to reduce the amount of computation processing.

(4-2-3) Modification 2C

The camera 121 described above is assumed to be an ordinary camera for visible-light areas. Alternatively, an infrared camera may be used. In this case, the infrared camera emits infrared light and receives the reflection of infrared light. Accordingly, captured image data indicating a change or the like in the subject's face can be obtained. The inventors have found that a correlation exists between blood-circulation-amount data calculated from captured image data obtained by the reflection of infrared radiation and blood-circulation-amount data calculated by mainly using the R component among the pixels included in RGB data of a captured image of a visible light area. Accordingly, even with the use of such captured image data obtained from the reflection of infrared radiation, human brain activity can be estimated.

(4-2-4) Modification 2D

In the foregoing description, the brain activity visualization device 110 includes the image data acquisition means 120 and the brain activity estimation means 130. However, the brain activity visualization device according to this embodiment is not limited thereto. That is, it is only required that the brain activity visualization device according to this embodiment includes the blood-circulation-amount calculation unit 133, the analysis unit 134, and the estimation unit 135, and the other elements may have any configuration. Specifically, the brain activity visualization device according to this embodiment may be configured not only to capture image data but also to receive captured image data from an external device and analyze the received captured image data.

(4-3) State Visualization Means 200

The state visualization means 200 visualizes the physiological state of a subject by displaying it on the basis of the brain activity of the subject estimated by the brain activity estimation means 30 and/or the brain activity estimation means 130. For example, the state visualization means 200 may include an analysis unit 201 that analyzes a change in the amount of brain activity of the subject to analyze the physiological state of the subject. Specifically, the analysis unit 201 analyzes a change in the amount of brain activity in response to a stimulus (such as a visual stimulus, an auditory stimulus, a tactile stimulus, an olfactory stimulus, or a gustatory stimulus) applied to the subject to determine the physiological state of the subject. The type or level of the physiological state may be set as appropriate on the basis of the degree of increase in the amount of brain activity and/or the duration of the increase according to the use of the brain activity visualization devices 10 and 110. The physiological state of the subject analyzed by the analysis unit 201 is output from a display unit 202 of the state visualization means 200 to an administrator. Accordingly, the administrator is able to understand the physiological state of the subject. The display unit 202 may be any device capable of making information concerning the analyzed physiological state of the subject visible to the administrator, such as a display device that displays an image or a message.

After the analysis units 32 and 134 identify a component that reflects brain activity, the facial skin temperature acquisition means 20 and/or the image data acquisition means 120 may further acquire various time-series data. In this case, in the brain activity visualization devices 10 and 110, the further acquired various data is decomposed into a plurality of components by using the singular value decomposition, and only the identified component is analyzed to provide a real-time notification of the physiological state of the subject.

There have been techniques for acquiring heart rate information, biometric information, or the like of a test subject from the facial skin temperature of the test subject or from a captured image of the test subject. Such existing techniques are employed for a component obtained by subjecting various data obtained from the facial skin temperature acquisition means 20 and/or the image data acquisition means 120 to the singular value decomposition or the like, thereby accurately acquiring heart rate information or biometric information. Accordingly, the analysis unit 32 and/or the analysis unit 134 may have a function of analyzing the plurality of components obtained through the singular value decomposition to acquire heart rate information or biometric information, and the estimation units 33 and 135 of the embodiment described above may have a function of estimating the activity of the sympathetic/parasympathetic nervous systems on the basis of the acquired heart rate information or biometric information.

(5) Features 5-1

In this embodiment, human brain activity is estimated on the basis of time-series facial skin temperature data and/or facial blood-circulation-amount data acquired by the facial skin temperature acquisition means 20 and/or the image data acquisition means 120. Accordingly, human brain activity can be estimated without using a sensor that requires processing before attachment, such as electroencephalogram electrodes. This can facilitate estimation of human brain activity, and enables visualization of the physiological state of the subject on the basis of the estimated brain activity.

5-2

When a situation is created in which the brain of a person is activated or deactivated by actually presenting a brain function activation exercise to the person or not during the acquisition of time-series facial skin temperature data and/or image data, a component whose component waveform has a correlation with the brain activation and deactivated times may be a component that is likely to be a component indicating a change in skin temperature and/or the amount of blood circulation that reflects brain activity.

In this embodiment, while the facial skin temperature acquisition means 20 and/or the image data acquisition means 120 acquires time-series facial skin temperature data and/or image data, a person is presented with a brain function activation exercise for a certain period. That is, in this embodiment, a situation is created in which the brain of a person is activated or deactivated by actually presenting a brain function activation exercise to the person or not. Then, the acquired various time-series data is decomposed into a plurality of components by using the singular value decomposition, the correlation between the component waveform of each of the components and the brain activation and deactivated times is evaluated, and a component having a correlation with the brain activation and deactivated times is extracted from the plurality of components as a determination component. Accordingly, compared to when, for example, a predetermined component identified in advance by experiment or the like is extracted from the plurality of components as an extraction component, the possibility of extracting a component having low relevance to human brain activity from the plurality of components as an extraction component can be reduced.

5-3

The brain has a mechanism for cooling the brain while leaving the body temperature unchanged, called a selective brain cooling system. The selective brain cooling system is known to dissipate heat generated by brain activity through the forehead portion and the paranasal-sinus surrounding area. Thus, a change in the amount of facial blood circulation, which is correlated with the facial skin temperature or facial skin temperature that changes with brain activity, appears in the forehead portion and/or the paranasal-sinus surrounding area.

In this embodiment, various data of the forehead portion and/or the paranasal-sinus surrounding area is analyzed, and a determination component is extracted. Accordingly, a component related to human brain activity can be extracted accurately.

(6) Physiological State Determination Device

A physiological state determination device, to which the brain activity visualization device according to the present invention is applied, will be described. The physiological state determination device determines the physiological state of the mind and body of a subject. Specifically, the physiological state determination device determines "physiological states" as illustrated in FIGS. 23 and 24. That is, the physiological state determination device determines "the degree to which a vehicle/aircraft/railway driver concentrates on driving", "the degree of interest of a movie theater visitor in information on commercials", "the degree to which an examinee concentrates on an examination", "the degree to which an assembly worker concentrates on an assembly work", "the degree to which a subject who sees an item is interested in the item", "various psychological states (the state of depression, the state of autism spectrum disorder (ASD) such as autism and Asperger's syndrome, the state of dementia, the state of post-traumatic stress disorder (PTSD), and the state of anxiety disorder) of patients", "the degree of aging-related forgetfulness in an elderly person", and so on.

(6-1) First Embodiment

(6-1-1) Configuration of Physiological State Determination Device 500

Figure 25:
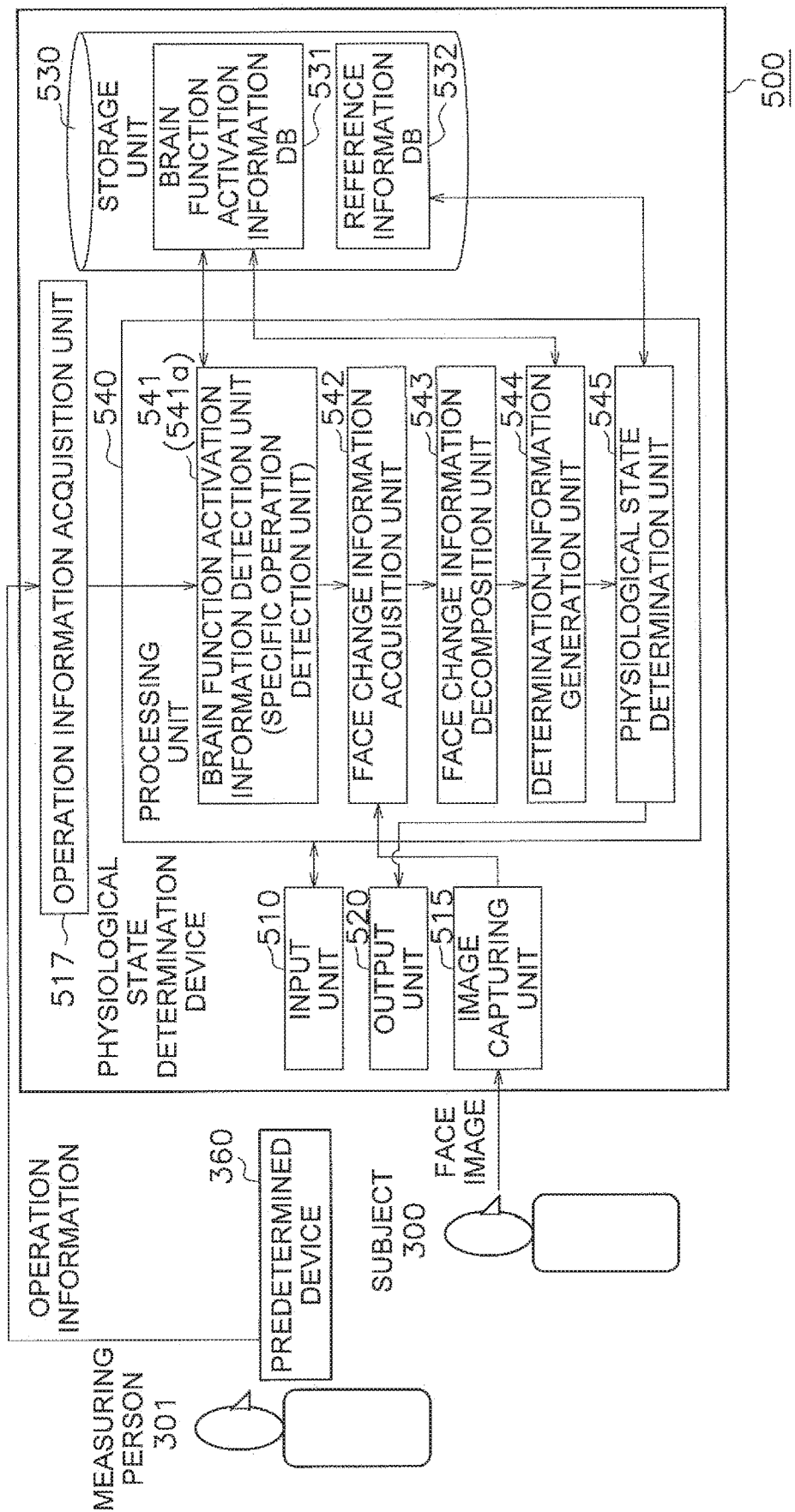
FIG. 25 is a schematic diagram illustrating a configuration of a physiological state determination device 500 according to a first embodiment.

FIG. 25 is a schematic diagram illustrating the configuration of a physiological state determination device 500 according to a first embodiment.

The physiological state determination device 500 includes an input unit 510, an image capturing unit 515, an operation information acquisition unit 517, an output unit 520, a storage unit 530, and a processing unit 540.

The input unit 510 inputs various types of information to the physiological state determination device 500. For example, the input unit 510 is constituted by a keyboard, a mouse, a touch screen, and/or the like. Various commands are input to the physiological state determination device 500 through the input unit 510, and the processing unit 540 executes processes in accordance with the commands.

The image capturing unit 515 captures a "face image" including the face of a subject 300. For example, the image capturing unit 515 is constituted by a solid-state imaging device that acquires an RGB image, such as a CCD device and a CMOS device, or an infrared camera or the like that acquires a thermogram. The infrared camera or the like is desirably capable of detecting temperatures from 29.0° C. to 37.0° C. in normal room temperature conditions with high sensitivity. Further, the image capturing unit 515 is capable of continuously capturing images at predetermined intervals. Face images are desirably captured from the front under constant illumination. When a front image is not obtainable due to changes in posture, the three-dimensional shape of the face is estimated for a posture-change image by using a perturbation space method, and a front image is rendered from the shape to obtain a face image. For an illumination-change image, an illumination basis model of the face, which is constructed based on a diffuse reflection model, is used to obtain a face image under constant illumination conditions. Then, face images continuously captured by the image capturing unit 515 are delivered to the processing unit 540.

Figure 26:
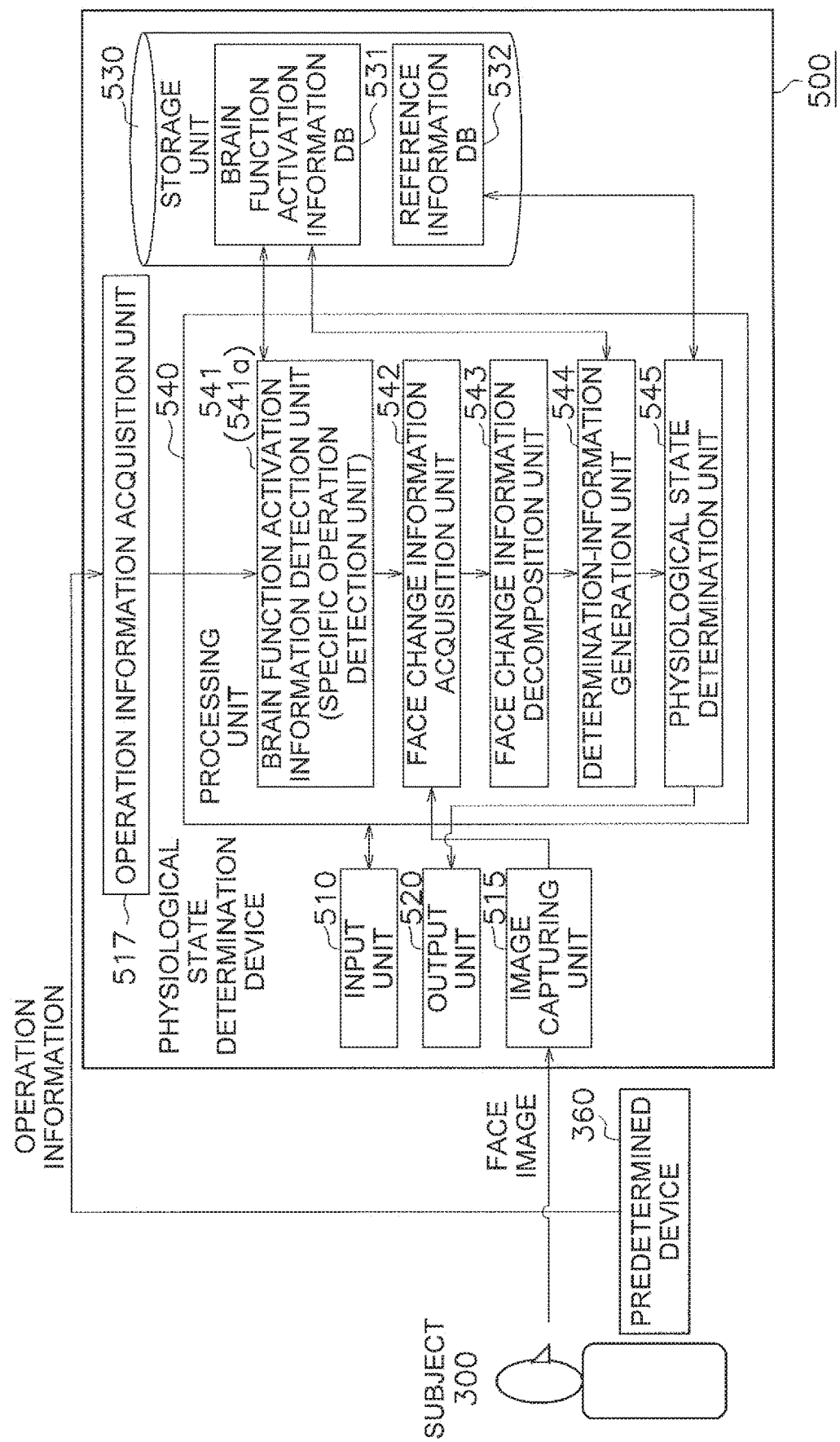
FIG. 26 is a schematic diagram illustrating a configuration of the physiological state determination device 500 according to the first embodiment.

The operation information acquisition unit 517 acquires operation information concerning a predetermined device 360. The "predetermined device" 360 is any information processing device used by an operator in accordance with the purpose of determination, and has a keyboard, a mouse, a tablet, buttons, a speaker, and so on. Examples of the predetermined device 360 include an examination management device, a patient examination device, an assembly work line operation device, and a telephone conversation device. The "operation information" is information indicating that the predetermined device 360 is operated, and is generated using speech made by the operator, key input made by the operator, switch input made through a button pressed by the operator, the value detected by an acceleration sensor disposed in the predetermined device 360, and so on. The operation information acquired by the operation information acquisition unit 517 is delivered to a brain function activation information detection unit (a specific operation detection unit 541a) described below. The term "operator" is used to include the subject 300 or a measuring person 301 other than the subject 300, and is used to include both a person who operates the predetermined device 360 directly and a person who operates the predetermined device 360 indirectly. Accordingly, the physiological state determination device may have the configuration illustrated in FIG. 25 or a configuration illustrated in FIG. 26.

The output unit 520 outputs various types of information from the physiological state determination device 500. For example, the output unit 520 is constituted by a display, a speaker, and so on. Brain function activation information described below can be provided to the subject 300 via the output unit 520.

The storage unit 530 stores information input to the physiological state determination device 500, information calculated by the physiological state determination device 500, and so on. For example, the storage unit 530 is constituted by a memory, a hard disk device, and so on. The storage unit 530 further stores a program for implementing functions of the processing unit 540 described below. Here, the storage unit 530 includes a brain function activation information database 531 and a reference information database 532.

The brain function activation information database 531 stores brain function activation information corresponding to a brain function activation stimulus for activating the human brain function. Examples of the "brain function activation stimulus" include, as illustrated in FIG. 23, "presentation of examination questions", an "instruction to assemble parts", "presentation of an item", "presentation of an emotional image", "presentation of various examination tools and questions", an "instruction to perform an operation action", an "instruction to view an image", and an "inquiry via a telephone conversation device". These brain function activation stimuli are regarded as being provided to the subject 300 when "specific operations" described below are detected.

Figure 27:
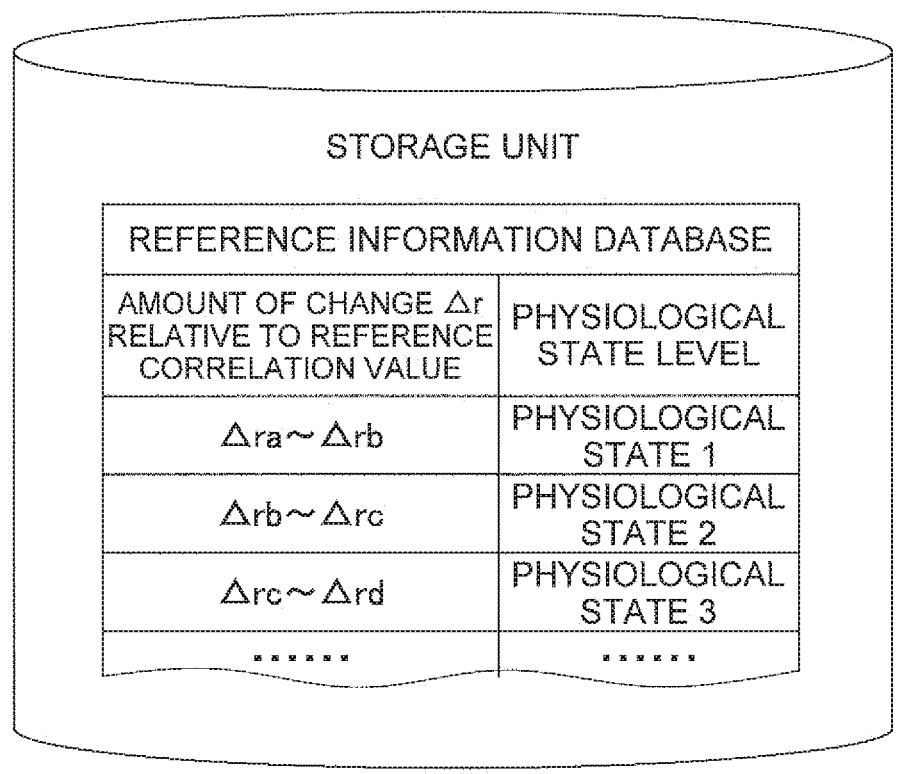
FIG. 27 is a schematic diagram illustrating the configuration of a reference database.

As illustrated in FIG. 27, the reference information database 532 stores, as "reference information", in advance, in association with a "physiological state level", an amount of change Δr(=r2−r1) of a correlation value r2 of a determination component relative for brain function activation information extracted by a determination-information generation unit 544 described below with respect to a "reference correlation value" r1 of a reference determination component relative for the brain function activation information, the amount of change Δr falling within a predetermined range. The "reference determination component" can be set by using data of a determination component extracted in normal conditions of the subject where their emotions and the like are stable, data of the previously extracted determination component, data of a determination component provided from the outside, or the like. In the example illustrated in FIG. 27, the reference information database 532 stores, in accordance with the range of values of the amount of change Δr, the range Δr=Δra to Δrb as "physiological state 1", the range of Δrb to Δrc as "physiological state 2", and the range of Δrc to Δrd as "physiological state 3", with the values Δra, Δrb, Δrc, and Δrd arranged in ascending order. The content of the physiological state 1 to the physiological state 3 is set as desired in accordance with the purpose of determination. The data of the reference determination component is also stored in the reference information database 532.

The processing unit 540 executes information processing performed in the physiological state determination device 500. Specifically, the processing unit 540 is constituted by a CPU, a cache memory, and so on. The program contained in the storage unit 530 is executed, thereby allowing the processing unit 540 to function as a brain function activation information detection unit 541, a face change information acquisition unit 542, a face change information decomposition unit 543, the determination-information generation unit 544, and a physiological state determination unit 545.

The brain function activation information detection unit 541 detects "brain function activation information" corresponding to a physiological state. Here, the brain function activation information detection unit 541 has a function of the specific operation detection unit 541a.

When a brain function activation stimulus is provided to the subject 300, the specific operation detection unit 541a determines whether a specific operation is performed on the predetermined device 360 by the subject 300 or the measuring person 301 other than the subject 300 to detect brain function activation information. As a precondition, if a specific operation is performed on the predetermined device 360 by the subject 300 or the measuring person 301 under a predetermined environment, a brain function activation stimulus is regarded as being provided to the subject 300. Accordingly, the specific operation detection unit 541a detects specific operation information corresponding to a specific operation from the operation information acquired by the operation information acquisition unit 517, thereby detecting that a brain function activation stimulus is provided to the subject 300. Examples of the "specific operation" include those illustrated in FIG. 23. That is, when the predetermined device 360 is an examination management device, an operation of inputting a start command and a termination command that are recognized by, for example, pressing of a button corresponds to a specific operation. When the predetermined device 360 is a combination of an examination management device and an examination execution device, an operation of inputting a start command and a termination command that are recognized by, for example, touching a tablet serving as the examination execution device corresponds to a specific operation. When the predetermined device 360 is a work line operation device used for an assembly work, an operation of inputting an operation command, which is recognized by, for example, pressing of an operation start instruction button, corresponds to a specific operation. When the predetermined device 360 is an item presenting device, an operation of inputting an item presentation command, which is recognized by, for example, pressing of an input button of the item presenting device by an operator at the timing of presenting an item, corresponds to a specific operation. The term item, as used herein, is used to include both a tangible item and an intangible item such as music. When the predetermined device 360 is any of various examination devices, an operation of inputting a command to present various questions, which is recognized by, for example, pressing of an input button by an operator to allow the examination device to recognize the timing when a brain function activation stimulus is provided, corresponds to a specific operation. When the predetermined device 360 is an operation instruction output device, an operation of inputting an operation instruction presentation command, which is recognized by, for example, pressing of a button, corresponds to a specific operation. When the predetermined device 360 is an image output device, an operation of inputting an image presentation command, which is recognized by, for example, pressing of a button, corresponds to a specific operation. When the predetermined device 360 is a telephone conversation device, an input operation corresponding to a response, which is recognized by, for example, inputting speech to the telephone conversation device, corresponds to a specific operation. The correspondence between brain function activation stimulus information and specific operation information is stored in the storage unit 530.

The face change information acquisition unit 542 acquires "face data" and "face change information" indicating a time-series change in the face data from the face images captured by the image capturing unit 515. Specifically, when the specific operation detection unit 541a detects that a specific operation is performed on the predetermined device 360, the face change information acquisition unit 542 acquires face data obtained at the timing of detection. Further, the face change information acquisition unit 542 acquires face change information indicating a time-series change in the face data of the subject 300 from continuously acquired face data. For example, when 60 pieces of face data of 240×320 pixels are acquired at predetermined intervals, the face change information is a collection of 4,608,000 pieces of data. The acquired face change information is delivered to the face change information decomposition unit 543. When the image capturing unit 515 is an infrared camera, the face change information acquisition unit 542 acquires, as face data, facial skin temperature data indicating the facial skin temperatures of the subject 300. When the image capturing unit 515 is a solid-state imaging device such as a CCD device and a CMOS device, the face change information acquisition unit 542 acquires, as face data, facial blood-circulation-amount data based on facial RGB data of the subject 300. The face change information acquisition unit 542 may acquire, as face data, only the data of the paranasal-sinus surrounding area and/or the forehead portion of the subject 300.

The face change information decomposition unit 543 decomposes the face change information, which is a collection of multiple pieces of data, into a plurality of components 1, 2, 3, . . . by using singular value decomposition, principal component analysis, or independent component analysis. Information on the components obtained through decomposition is delivered to the determination-information generation unit 544. When the face change information is subjected to the singular value decomposition or the like, the components 1, 2, 3, . . . are assigned in descending order of the singular values. In addition, a component having a higher singular value is more likely to be affected by a large variation. Accordingly, component 1 is usually affected by noise or the like in an external environment, rather than by the provision of the brain function activation information.

Figure 28:
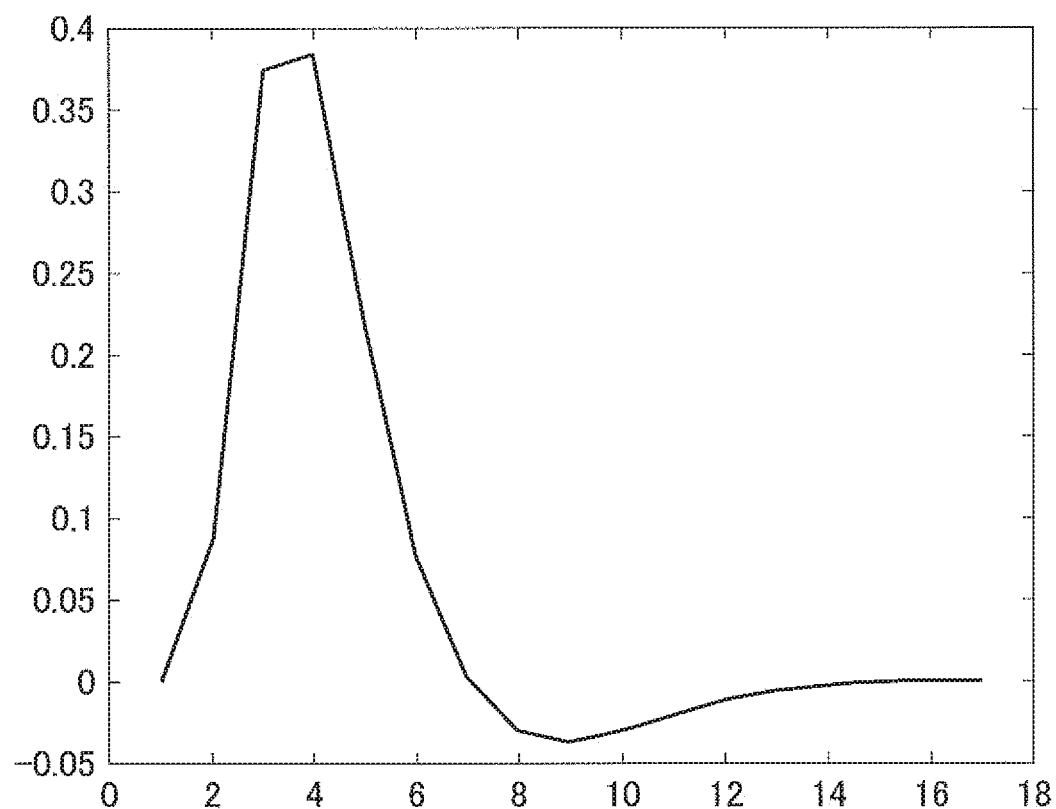
FIG. 28 is a schematic diagram describing a redspot-dynamic response function.

The determination-information generation unit 544 generates determination information from the face change information. Specifically, the determination-information generation unit 544 extracts, as the "determination component", a component related to the brain function activation information from the plurality of components 1, 2, 3, . . . , and generates determination information from the determination component. More specifically, the determination-information generation unit 544 calculates a correlation value r between each of the plurality of components 1, 2, 3, . . . determined by the face change information decomposition unit 543 and the "determination waveform" corresponding to the brain function activation information. Then, when the calculated correlation value r is greater than or equal to a predetermined value, the determination-information generation unit 544 sets the component corresponding to the correlation value r as a component related to the brain function activation information. Then, the determination-information generation unit 544 extracts the determination component on the basis of the value of the significance level. That is, the determination-information generation unit 544 extracts a component having a low significance level as the determination component. The extracted determination component and the calculated correlation value r are delivered to the storage unit 530 or the physiological state determination unit 545. As the "determination waveform" described above, a modified wave that takes the human physiological response into account is used. The determination waveform is displaced after a predetermined time elapses after the detection of the brain function activation information. Specifically, a rectangular wave may be employed as the determination waveform. Alternatively, a waveform, which is a convolution of a rectangular wave with a redspot-dynamic response function, may be employed as the determination waveform. The redspot-dynamic response function is generated from the average value or the like of a plurality of components determined by calculating a component found to have a correlation with brain function activation information that is provided for a moment among the plurality of components 1, 2, 3, . . . obtained through decomposition by the face change information decomposition unit 543 and by performing the same calculation a plurality of times. At this time, amplitude (height direction) is in arbitrary unit, and no absolute value can be given. A signal obtained when the subject 300 is in normal conditions is used as a baseline value, and this value is used as a reference to determine the height of the waveform. Then, the average value of superimposed pieces of data, which are obtained from a plurality of test subjects, is calculated to generate a redspot-dynamic response function. The initial value of the redspot-dynamic response function has a waveform illustrated in FIG. 28 when the brain function activation information is provided for a moment. When the brain function activation information is provided for a certain period of time, a redspot-dynamic response function is generated from a convolution with a rectangular wave. The redspot-dynamic response function has a waveform in which, as the amount of displacement increases, a peak value extends along the horizontal axis from the peak time point. The redspot-dynamic response function further has a waveform whose phase is delayed at the time point at which the detection of the brain function activation information is finished, with the displacement decreasing. The redspot-dynamic response function, when found to have a significant correlation with a component obtained from the face change information, has a shape close to the correlation waveform and thus has a higher correlation value than a rectangular wave or the like. This can enhance the accuracy of the extraction of the determination component.

The physiological state determination unit 545 determines the physiological state of the subject 300 on the basis of the determination information including the determination component. Specifically, the physiological state determination unit 545 calculates a difference Δr between the reference correlation value r1 for the reference determination component and the correlation value r2 for the determination component extracted when the brain function activation information is detected. Then, the physiological state determination unit 545 determines a physiological state level corresponding to the difference Δr between the reference correlation value r1 and the correlation value r2 on the basis of the reference information stored in the reference information database 532. The determined physiological state level is output to the display device or the like via the output unit 520.

(6-1-2) Operation of Physiological State Determination Device 500

Figure 29:
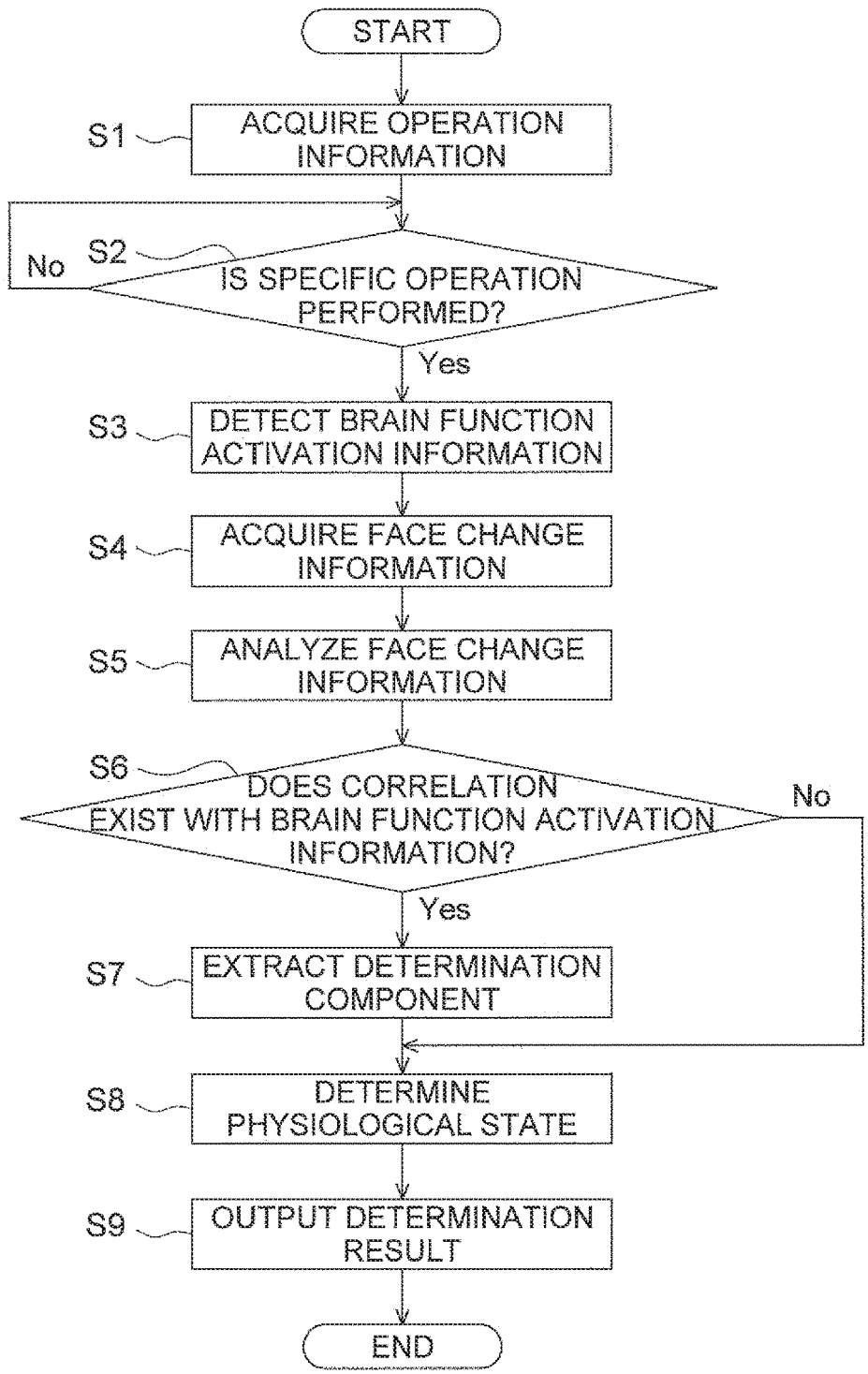
FIG. 29 is a flowchart illustrating the operation of the physiological state determination device 500 according to the first embodiment.

FIG. 29 is a flowchart illustrating the operation of the physiological state determination device 500 according to the first embodiment. In the following description, a description will be given, taking an example of "the degree of concentration of an examinee who answers examination questions" as a physiological state.

As a precondition, when a brain function activation stimulus (examination questions) is provided to the subject 300 (examinee), the subject 300 (examinee) or the measuring person 301 (examiner) performs a specific operation (input of a start button) on the predetermined device 360 (examination management device).

Under the precondition described above, the specific operation detection unit 541a determines whether a specific operation (input of the start button) is performed on the predetermined device 360 (examination management device) by the subject 300 (examinee) or the measuring person 301 (examiner) on the basis of the information acquired by the operation information acquisition unit 517 (S1, S2).

If it is determined that the specific operation is performed on the predetermined device 360, the specific operation detection unit 541a determines that the brain function activation stimulus (examination questions) is provided to the subject 300, and extracts and detects the brain function activation information corresponding to the brain function activation stimulus (examination questions) from the brain function activation information database 531 (S2—Yes, S3).

When the specific operation detection unit 541a detects the brain function activation information, the image capturing unit 515 starts capturing a face image of the subject 300 (examinee) (S4). The captured face image is delivered to the face change information acquisition unit 542.

Subsequently, in the physiological state determination device 500, the captured face image is analyzed (S5). Specifically, the face change information acquisition unit 542 acquires, from the captured face image, face change information indicating a time-series change in face data of the subject 300. Then, the face change information decomposition unit 543 performs singular value decomposition, principal component analysis, or independent component analysis to decompose the face change information into a plurality of components 1, 2, 3, . . . . Further, the determination-information generation unit 544 calculates a correlation value between each of the plurality of components 1, 2, 3, . . . obtained through decomposition by the face change information decomposition unit 543 and the brain function activation information. Then, the determination-information generation unit 544 determines whether the correlation value is greater than or equal to a predetermined value (S6). If the correlation value is determined to be greater than or equal to the predetermined value, it is determined that "a correlation exists" between the brain function activation information and the component (T6—Yes). Then, the determination-information generation unit 544 extracts a component having a correlation with the brain function activation information and having a low significance level as a "determination component" (S7). Information on the extracted determination component is stored in the storage unit 530. On the other hand, if the correlation value between the brain function activation information and each of the components 1, 2, 3, . . . is less than the predetermined value, it is determined that "a correlation does not exist" between them, and information indicating that a correlation does not exist is stored in the storage unit 530 (S6–No). Specifying a "component having a correlation" with brain function activation information in advance from previous measured values and the like can eliminate the operation of steps S6 and S7 described above.

Then, the physiological state determination unit 545 calculates the amount of change $\Delta r$, which is the difference between the reference correlation value r1 for the reference determination component and the correlation value r2 for the determination component extracted for the brain function activation information. Subsequently, the physiological state determination unit 545 determines a physiological state level in accordance with the amount of change $\Delta r$ of the correlation value r2 with respect to the reference correlation value r1 (S8). Here, physiological state level 1 is determined as a "normal degree of concentration", physiological state level 2 as a "slightly high degree of concentration", and physiological state level 3 as a "very high degree of concentration". The determination result is output via the output unit 520 as a determination result (S9).

Thereafter, the physiological state determination device 500 stores, for each subject 300 (examinee), data of a determination result, an analysis waveform, a measurement result, image display conditions, and so on in the storage unit 530 in association with each other, as necessary. The storage unit 530 saves information on the subject 300 in association with an examinee number, for example.

(6-1-3) Features of Physiological State Determination Device 500

6-1-3-1

As described above, the physiological state determination device 500 according to this embodiment includes the brain function activation information detection unit 541, the face change information acquisition unit 542, and the physiological state determination unit 545. The brain function activation information detection unit 541 detects brain function activation information corresponding to a physiological state. The face change information acquisition unit 542 acquires face change information indicating a time-series change in face data of the subject 300. The physiological state determination unit 545 determines a predetermined physiological state of the subject 300 on the basis of the brain function activation information and the face change information.

Accordingly, with the provision of the brain function activation information detection unit 541, the physiological state determination device 500 according to this embodiment is capable of detecting brain function activation information from any brain function activation stimulus. With this configuration, the physiological state of the subject 300 can be more easily determined than with a device that provides a brain function activation stimulus and determines a physiological state.

In particular, in the physiological state determination device 500, the brain function activation information detection unit 541 has a function of the specific operation detection unit 541*a*. When a specific operation is performed on the predetermined device 360 by the subject 300 or the measuring person 301 other than the subject 300, the specific operation detection unit 541*a* determines that the subject 300 is provided with a brain function activation stimulus, and detects brain function activation information. In summary, the physiological state determination device 500 is capable of detecting brain function activation information in response to detection of a specific operation on the predetermined device 360.

6-1-3-2

In the physiological state determination device 500 according to this embodiment, furthermore, when the specific operation detection unit 541*a* detects that a specific operation is performed on the predetermined device 360, the face change information acquisition unit 542 acquires face change information.

Accordingly, in the physiological state determination device 500, when a specific operation on the predetermined device 360 is detected, the face change information acquisition unit 542 acquires face change information. This can avoid acquisition and/or storage of information unnecessary for determination.

In the physiological state determination device 500 according to this embodiment, the face change information acquisition unit 542 acquires face change information used as a reference at any timing when no brain function activation stimulus is provided to the subject 300. With the use of the face change information used as a reference, the physiological state determination unit can determine a physiological state of the subject 300 from face change information acquired when the specific operation detection unit 541*a* detects brain function activation stimulus information.

6-1-3-3

Furthermore, the physiological state determination device 500 according to this embodiment further includes the determination-information generation unit 544 that generates determination information from the face change information. Then, the physiological state determination unit 545 determines a physiological state on the basis of the determination information. Accordingly, determination information for determining a physiological state is generated from the face change information, and a physiological state of a subject is determined. Thus, the physiological state of the subject can be determined.

Furthermore, the physiological state determination device 500 according to this embodiment further includes the face change information decomposition unit 543 that decomposes the face change information into a plurality of components by using singular value decomposition, principal component analysis, or independent component analysis. Then, the determination-information generation unit 544 extracts a component related to the brain function activation information from among the plurality of components as a determination component and generates determination information from the determination component.

Accordingly, in the physiological state determination device 500, a determination component related to brain function activation information is extracted from among a plurality of components obtained by subjecting face change information to singular value decomposition or the like. This eliminates a need to make a subject wear a special device such as electrodes, and makes it possible to easily estimate the presence of brain activity of the subject. Thus, the physiological state of the subject can be easily determined on the basis of a determination component corresponding to the brain function of the subject.

The physiological state determination device 500 according to this embodiment may be configured to be incorporated in a smart device. This configuration facilitates the determination of a physiological state at any location.

6-1-3-4

In the physiological state determination device 500 according to this embodiment, furthermore, the face change information acquisition unit 542 acquires, as face data, data of the paranasal-sinus surrounding area and/or the forehead portion of the subject 300. Thus, a determination component related to brain activity can be extracted accurately. The brain has a mechanism for cooling the brain while leaving the body temperature unchanged, called a selective brain cooling system. The selective brain cooling system dissipates heat generated by brain activity through an area around the paranasal sinuses and the forehead portion. By analyzing data of these parts, a component related to brain activity can be extracted accurately. As a result, the physiological state determination device 500 according to this embodiment is capable of executing high accuracy determination of a physiological state.

6-1-3-5

Figure 30:
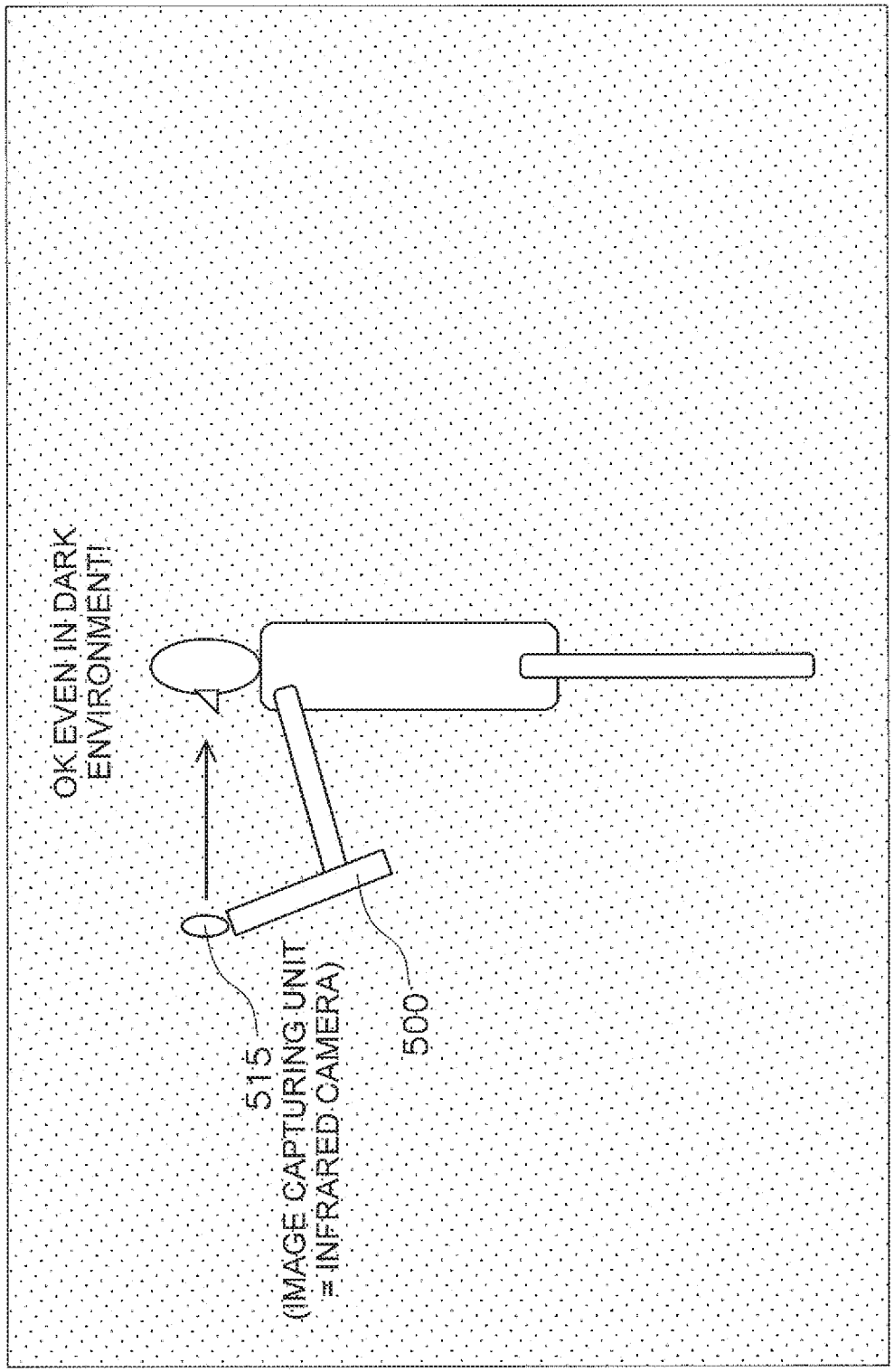
FIG. 30 is a schematic diagram describing a situation where an infrared camera is used as an image capturing unit 515.

In the physiological state determination device 500 according to this embodiment, furthermore, the face change information acquisition unit 542 can acquire, as face data, facial skin temperature data indicating the facial skin temperature of the subject 300. In other words, the physiological state determination device 500 is configured to be capable of determining the state of fatigue by using an infrared camera or the like. For example, as illustrated in FIG. 30, using an infrared camera as the image capturing unit 515 enables a physiological state to be determined without being affected by the surrounding brightness.

6-1-3-6

In the physiological state determination device 500 according to this embodiment, furthermore, the face change information acquisition unit 542 can acquire, as face data, facial blood-circulation-amount data based on facial RGB data of the subject 300. That is, the physiological state determination device 500 is capable of determining a physiological state by using a solid-state imaging device (CCD, CMOS), This enables a physiological state to be determined with a simple configuration.

6-1-3-7

In the physiological state determination device 500 according to this embodiment, furthermore, the determination-information generation unit 544 extracts a determination component on the basis of the value of the significance level. In the physiological state determination device 500, a determination component related to brain function activation information is extracted on the basis of the value of the significance level. This enables an increase in the reliability of determination of a physiological state.

6-1-3-8

Furthermore, the physiological state determination device 500 according to this embodiment includes the reference information database 532 that stores, as "reference information", in association with a physiological state level, an amount of change Δr of the correlation value r2 of a determination component calculated for brain function activation information with respect to the reference correlation value r1 of a reference determination component calculated for the brain function activation information, the amount of change Δr falling within a predetermined range. Further, the physiological state determination unit 545 calculates the correlation value r2 of the determination component for the brain function activation information, and determines the physiological state level of the subject 300 on the basis of the calculated correlation value r2 and the reference information.

With this configuration, the physiological state determination device 500 is capable of easily determining a physiological state level by using the reference determination component. In summary, the physiological state determination device 500 is capable of not only determining the presence of a physiological state but also easily determining a physiological state level and outputting the physiological state level.

6-1-3-9

A physiological state determination method according to this embodiment does not necessarily require the physiological state determination device 500. That is, a physiological state determination method according to this embodiment may include, regardless of whether the physiological state determination device 500 is used, a brain function activation information detection step of detecting "brain function activation information" for activating the human brain function, a face change information acquisition step of acquiring "face change information" indicating a time-series change in face data of the subject 300, a face change information decomposition step of decomposing the face change information into a plurality of components by using singular value decomposition, principal component analysis, or independent component analysis, a determination component extraction step of extracting a component related to the brain function activation information from among the plurality of components as a "determination component", and a physiological state determination step of determining a physiological state of the subject 300 on the basis of the determination component.

In this physiological state determination method, a determination component related to brain function activation information is extracted from among a plurality of components obtained by subjecting face change information to singular value decomposition, principal component analysis, or independent component analysis to determine a physiological state. This makes it possible to easily determine the influence of a physiological state of the subject 300 provided with a brain function activation stimulus.

6-1-3-10

In the foregoing description, face change information is subjected to singular value decomposition or the like, from which a determination component related to brain function activation information corresponding to the purpose of determination is extracted. However, the physiological state determination device 500 according to this embodiment is not limited to this configuration. For example, in the physiological state determination device 500, any determination information other than a determination component, which is generated on the basis of face change information, may be used to determine the state of a subject. In addition, to generate this determination information, any technique, other than singular value decomposition or the like, may be applied to face change information.

(6-1-4) Modification of Physiological State Determination Device 500

Figure 31:
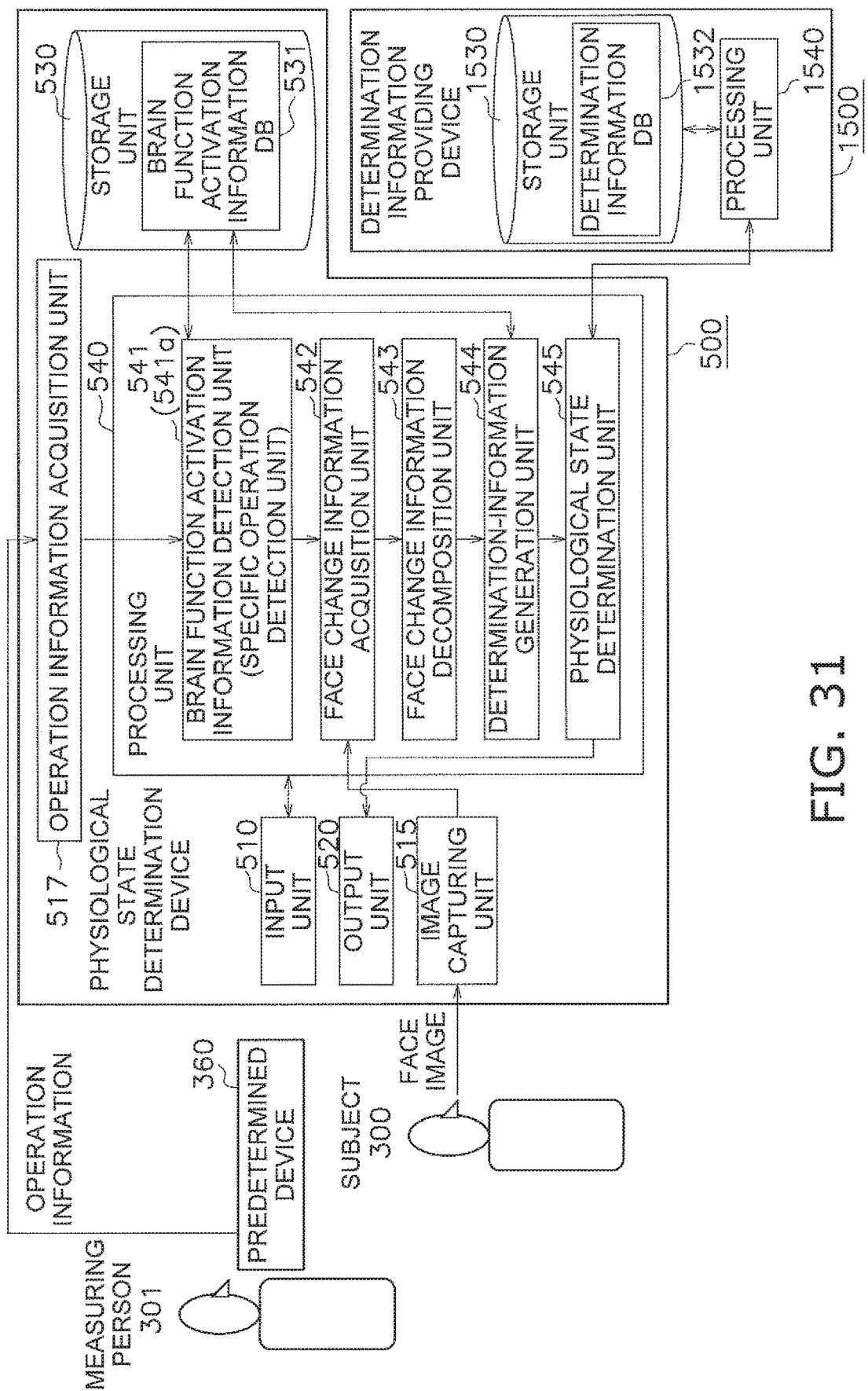
FIG. 31 is a schematic diagram illustrating the configuration of a physiological state determination device 500 according to a modification of the first embodiment.

As illustrated in FIG. 31, the physiological state determination device 500 according to this embodiment may utilize a determination information providing device 1500 or the like located on a network.

The determination information providing device 1500 includes a storage unit 1530 and a processing unit 1540.

The storage unit 1530 has a reference information database 1532. The reference information database 1532 has a configuration similar to that of the reference information database 532 described above. That is, the reference information database 1532 stores, as reference information, in association with a physiological state level, an amount of change Δr of the correlation value r2 of a determination component calculated for brain function activation information with respect to the reference correlation value r1 of a reference determination component calculated for the brain function activation information, the amount of change Δr falling within a predetermined range.

The processing unit 1540 transmits the reference information stored in the reference information database 1532 in response to a request from the physiological state determination device 500. The processing unit 1540 may have a function of generating reference information as big data on the basis of predetermined information, independently of the determination component extracted by the physiological state determination device 500. When the physiological state determination device 500 calculates the reference correlation value r1, the processing unit 1540 executes a process for updating the reference correlation value r1 stored in the reference information database 1532, as necessary.

In this modification, the physiological state determination unit 545 requests the determination information providing device 1500 described above to provide reference information. More specifically, in the physiological state determination device 500 according to this modification, the reference information database 1532 is stored in the determination information providing device 1500 on the network, and the physiological state determination unit 545 accesses the determination information providing device 1500 when determining a physiological state level. Then, the physiological state determination unit 545 determines the physiological state level of the subject 300 on the basis of the calculated correlation value r2 and the reference information.

Accordingly, in the physiological state determination device 500 of this modification, the physiological state determination unit 545 can determine the physiological state level of the subject 300 by using an external network.

Furthermore, the configuration of this modification can implement the determination of a physiological state using big data. That is, the reference correlation value r1 and the predetermined amount of change Δr are determined from big data, Specifically, the reference correlation value r1, which is calculated on the basis of a reference determination component obtained by providing brain function activation information to a person other than the subject 300, is used. This can optimize the reference information, as necessary.

(6-2) Second Embodiment (6-2-1) Configuration of Physiological State Determination Device 600

In this embodiment, positioning of the subject 300 in a specific environment in which a brain function activation stimulus is regarded as being present is detected. Here, the brain function activation stimulus is provided to the subject 300 by a brain function activation stimulus provider 370.

Figure 32:
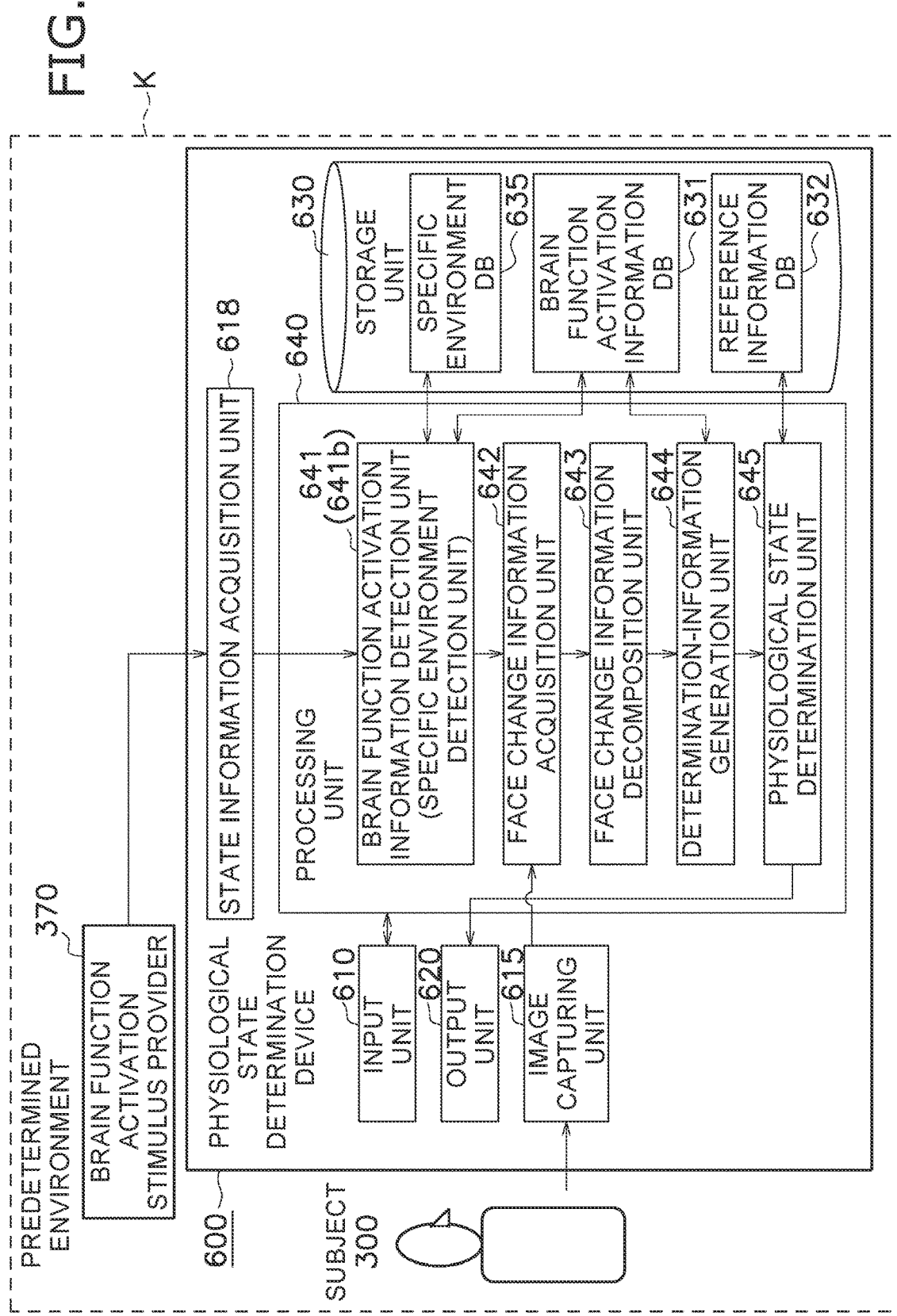
FIG. 32 is a schematic diagram illustrating the configuration of a physiological state determination device 600 according to a second embodiment.

FIG. 32 is a schematic diagram illustrating the configuration of a physiological state determination device 600 according to a second embodiment.

The physiological state determination device 600 includes an input unit 610, an image capturing unit 615, a state information acquisition unit 618, an output unit 620, a storage unit 630, and a processing unit 640. The input unit 610, the image capturing unit 615, and the output unit 620 have functions and configurations similar to those of the input unit 510, the image capturing unit 515, and the output unit 520 described above, respectively, and will not be described here.

The state information acquisition unit 618 acquires state information in an environment in which the subject 300 is positioned, in accordance with the physiological state for the purpose of determination. The "state information" is information indicating a spatial and temporal state corresponding to the physiological state for the purpose of determination, and is represented in form of an image, audio, schedule, or the like, To acquire the state information represented in the form described above, the state information acquisition unit 618 is provided with a "camera", a "GPS system or the like", a "laser", an "acceleration sensor or the like", a "sound detection sensor or the like", a "signal", a "screening schedule management device", and so on. Information acquired by the state information acquisition unit 618 is delivered to a brain function activation information detection unit 641 (specific environment detection unit 641b) of the processing unit 640.

The storage unit 630 stores information input to the physiological state determination device 600, information computed by the physiological state determination device 600, and so on. For example, the storage unit 630 is constituted by a memory, a hard disk device, and the like. The storage unit 630 further stores a program for implementing functions of the processing unit 640 described below. Here, the storage unit 630 includes a brain function activation information database 631, a reference information database 632, and a specific environment database 635.

The brain function activation information database 631 stores brain function activation information corresponding to a brain function activation stimulus for activating the human brain function. Examples of the "brain function activation stimulus" include, as illustrated in FIG. 24, "red light", "presence of pedestrians, other vehicles and the like, an intersection, or a pedestrian crossing", "a situation where the aircraft needs to be recovered (such as strong winds)". "a situation where the train experiences any abnormal occurrence (situation of train anomaly)", "a situation where careful maneuvering is necessary, such as the train approaching the station (the presence of a signal, safety personnel, a railroad crossing, or a station)", and "movie theater video commercials (M)".

The reference information database 632 has a configuration similar to that of the reference information database 532 described above. Thus, the reference information database 632 stores physiological state levels in accordance with the range of values of the amount of change Δr such that the range Δr=Δra to Δrb is represented as "physiological state 1", the range of Δrb to Δrc as "physiological state 2", and the range of Δrc to Δrd as "physiological state 3". The content of the physiological state 1 to the physiological state 3 is set as desired in accordance with the purpose of determination.

The specific environment database 635 stores, in advance, state information for a specific environment in which a brain activation stimulus is regarded as being present, as illustrated in FIG. 24, in accordance with the physiological state for the purpose of determination.

For example, when the brain function activation stimulus is the "red light" and the physiological state for the purpose of determination is "the degree of concentration of a driver driving a vehicle", the specific environment database 635 stores "surrounding information or the like that alerts the driver (such as a red-light image)" as the state information for the specific environment.

When the brain function activation stimulus is the "presence of pedestrians, other vehicles and the like, an intersection, or a pedestrian crossing" and the physiological state for the purpose of determination is "the degree of concentration of a driver driving a vehicle", the specific environment database 635 stores "position information (combined with map information, if necessary)" as the state information for the specific environment.

When the brain function activation stimulus is "a situation where the aircraft needs to be recovered (such as strong winds)" and the physiological state for the purpose of determination is "the degree of concentration of an aircraft operator maneuvering the aircraft", the specific environment database 635 stores "acceleration information indicating the state of the aircraft to alert the aircraft operator to recover the aircraft" as the state information for the specific environment.

When the brain function activation stimulus is "a situation where the train experiences any abnormal occurrence (situation of train anomaly)" and the physiological state for the purpose of determination is "the degree of concentration of a train driver driving the train", the specific environment database 635 stores "abnormal values for the respective train driving parameters and output information or the like of a failure alarm in response to the abnormal values" as the state information for the specific environment.

When the brain function activation stimulus is "a situation where careful maneuvering is necessary, such as the train approaching the station (the presence of a signal, safety personnel, a railroad crossing, or a station)" and the physiological state for the purpose of determination is "the degree of concentration of a train driver driving the train", the specific environment database 635 stores "position information (combined with map information, if necessary)" or "surrounding information or the like that alerts the driver" as the state information for the specific environment.

When the brain function activation stimulus is "movie theater video commercials (CM)" and the physiological state for the purpose of determination is "the degree of interest of a movie theater visitor in movie theater video commercials", the specific environment database 635 stores "CM-output time information or the like (screening schedule information) within time information regarding movie screening" as the state information for the specific environment.

The processing unit 640 executes information processing performed in the physiological state determination device 600. Specifically, the processing unit 640 is constituted by a CPU, a cache memory, and so on. The program contained in the storage unit 630 is executed, thereby allowing the processing unit 640 to function as a brain function activation information detection unit 641, a face change information acquisition unit 642, a face change information decomposition unit 643, a determination-information generation unit 644, and a physiological state determination unit 645. The face change information decomposition unit 643, the determination-information generation unit 644, and the physiological state determination unit 645 have functions similar to those of the face change information decomposition unit 543, the determination-information generation unit 544, and the physiological state determination unit 545, respectively, and will not be described here.

The brain function activation information detection unit 641 detects "brain function activation information" corresponding to a physiological state. Here, the brain function activation information detection unit 641 has a function of the specific environment detection unit 641b.

The specific environment detection unit 641b determines whether the state information acquired by the state information acquisition unit 618 is state information for a specific environment in which a brain activation stimulus is present to detect brain function activation information. Specifically, the specific environment detection unit 641b requests the state information acquisition unit 618 to transmit state information corresponding to the brain function activation stimulus, and acquires the state information from the state information acquisition unit 618 in response to the request for transmission. Then, the specific environment detection unit 641b matches the state information acquired by the state information acquisition unit 618 against the information in the specific environment database 635, and determines whether the state information acquired by the state information acquisition unit 618 is the state information for the specific environment in which the brain activation stimulus is present. If the state information acquired by the state information acquisition unit 618 is determined to be the state information in the specific environment, the specific environment detection unit 641b determines that the brain function activation stimulus is provided to the subject 300, and extracts and detects the brain function activation information corresponding to the brain function activation stimulus from the brain function activation information database 631. For example, when the "red light" is used as a brain function activation stimulus, the specific environment detection unit 641b requests the state information acquisition unit 618 to transmit an "image of the surroundings (an area within a predetermined range from the current position of the vehicle)". When the image of the surroundings is sent from the state information acquisition unit 618 in response to the request for transmission, the specific environment detection unit 641b matches the image of the surroundings against the information in the specific environment database 635, and determines whether the image of the surroundings includes a "red light image". If the image of the surroundings is determined to include a "red light image", the specific environment detection unit 641b determines that the brain function activation stimulus (red light) is provided to the subject 300, and extracts and detects the brain function activation information corresponding to the brain function activation stimulus from the brain function activation information database 631.

The face change information acquisition unit 642 acquires "face data" and "face change information" indicating a time-series change in the face data from the face images captured by the image capturing unit 615. Specifically, when the specific environment detection unit 641b detects state information in a predetermined environment K as state information fora specific environment in which a brain function activation stimulus is regarded as being present, the face change information acquisition unit acquires face data obtained at the timing of detection. The other functions of the face change information acquisition unit 642 are similar to those of the face change information acquisition unit 542 described above.

In the physiological state determination device 600 according to this embodiment, a configuration other than the configuration described above is similar to that of the physiological state determination device 500 according to the first embodiment.

(6-2-2) Operation of Physiological State Determination Device 600

Figure 33:
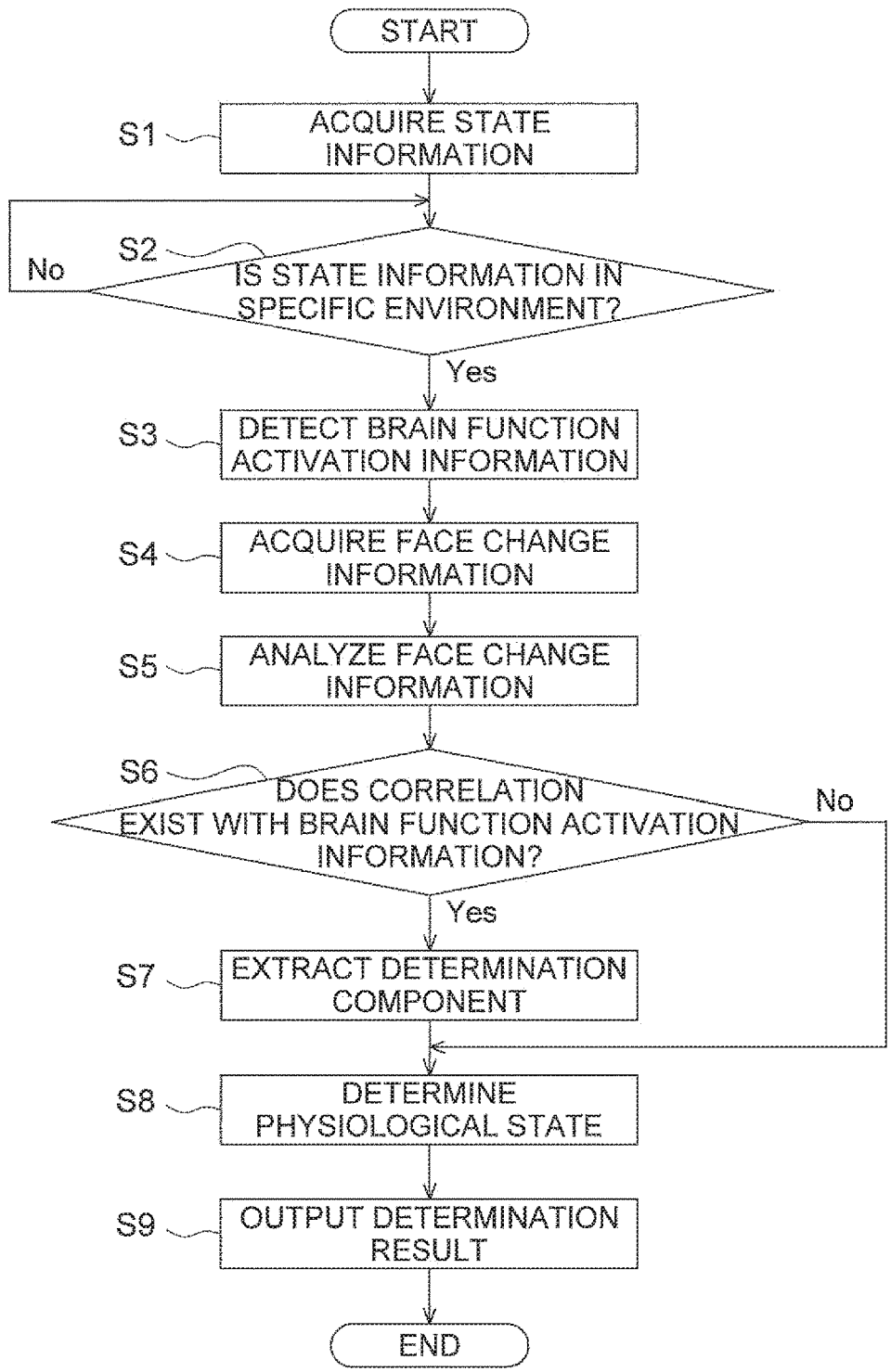
FIG. 33 is a flowchart illustrating the operation of the physiological state determination device 600 according to the second embodiment.

FIG. 33 is a flowchart illustrating the operation of the physiological state determination device 600 according to the second embodiment. In the following description, a description will be given, taking an example of "the degree of interest of a movie theater visitor in movie theater video commercials (CM)" as a physiological state.

As a precondition, the subject 300 (movie theater visitor) is provided with a brain function activation stimulus (CM) in the predetermined environment K (a room in which a movie is screened). The brain function activation stimulus (CM) activates the brain function of the subject 300 (movie theater visitor). Accordingly, it is found that a correlation exists between the physiological state (the degree of interest in CM) of the subject 300 (movie theater visitor) and the state in which the brain function of the subject 300 (movie theater visitor) is activated.

Under the precondition described above, the state information acquisition unit 618 acquires state information ("time information regarding movie screening") (T1). Then, the specific environment detection unit 641b determines whether the state information acquired by the state information acquisition unit 618 (time information regarding movie screening) is the state information in the specific environment in which the brain activation stimulus (CM) is regarded as being present (CM—output time information within the time information regarding movie screening) (T2).

If it is determined that the state information (time information regarding movie screening) acquired by the state information acquisition unit 618 is the state information in the specific environment in which the brain activation stimulus (video commercials) is regarded as being present (CM-output time information within the time information regarding movie screening), the specific environment detection unit 641b determines that the brain function activation stimulus (CM) is provided to the subject 300, and extracts and detects the brain function activation information corresponding to the brain function activation stimulus (CM) from the brain function activation information database 631 (T2—Yes, T3).

When the specific environment detection unit 641b detects the brain function activation information, the image capturing unit 615 starts capturing a face image of the subject 300 (movie theater visitor) (T4). The captured face image is delivered to the face change information acquisition unit 642.

Subsequently, in the physiological state determination device 600, the captured face image is analyzed (T5). Specifically, the face change information acquisition unit 642 acquires, from the captured face image, face change information indicating a time-series change in face data of the subject 300. Then, the face change information decomposition unit 643 performs singular value decomposition, principal component analysis, or independent component analysis to decompose the face change information into a plurality of components 1, 2, 3, . . . . Further, the determination-information generation unit 644 calculates a correlation value between each of the plurality of components 1, 2, 3, . . . obtained through decomposition by the face change information decomposition unit 643 and the brain function activation information. Then, the determination-information generation unit 644 determines whether the correlation value is greater than or equal to a predetermined value (T6). If the correlation value is determined to be greater than or equal to the predetermined value, it is determined that "a correlation exists" between the brain function activation information and the component (T6—Yes). Then, the determination-information generation unit 644 extracts a component having a correlation with the brain function activation information and having a low significance level as a "determination component" (T7). Information on the extracted determination component is stored in the storage unit 630. On the other hand, if the correlation value between the brain function activation information and each of the components 1, 2, 3, . . . is less than the predetermined value, it is determined that "a correlation does not exist" between them, and information indicating that a correlation does not exist is stored in the storage unit 630 (T6–No). Specifying a "component having a correlation" with brain function activation information in advance from previous measured values and the like can eliminate the operation of steps T5 and T6 described above.

Then, the physiological state determination unit 645 calculates the amount of change $\Delta r$, which is the difference between the reference correlation value r1 for the reference determination component and the correlation value r2 for the determination component extracted for the brain function activation information. Subsequently, the physiological state determination unit 645 determines a physiological state level in accordance with the amount of change $\Delta r$ of the correlation value r2 with respect to the reference correlation value r1 (T8). Here, physiological state level 1 is determined as a "normal degree of interest", physiological state level 2 as a "slightly high degree of interest", and physiological state level 3 as a "very high degree of interest". The determination result is output via the output unit 620 as a determination result (T9).

Thereafter, the physiological state determination device 600 stores, for each subject 300 (movie theater visitor), data of a determination result, an analysis waveform, a measurement result, image display conditions, and so on in the storage unit 630 in association with each other, as necessary. The storage unit 630 saves information on the subject 300 in association with a seat in the movie theater, for example.

(6-2-3) Features of Physiological State Determination Device 600

6-2-3-1

As described above, the physiological state determination device 600 according to this embodiment includes the brain function activation information detection unit 641, the face change information acquisition unit 642, and the physiological state determination unit 645. The brain function activation information detection unit 641 detects brain function activation information corresponding to a physiological state. The face change information acquisition unit 642 acquires face change information indicating a time-series change in face data of the subject 300. The physiological state determination unit 645 determines a predetermined physiological state of the subject 300 on the basis of the brain function activation information and the face change information.

Accordingly, with the provision of the brain function activation information detection unit 641, the physiological state determination device 600 according to this embodiment is capable of detecting brain function activation information from any brain function activation stimulus. With this configuration, the physiological state of the subject 300 can be more easily determined than with a device that provides a brain function activation stimulus and determines a physiological state.

In particular, in the physiological state determination device 600, the brain function activation information detection unit 641 has a function of the specific environment detection unit 641b. The specific environment detection unit 641b determines whether state information in the predetermined environment K is state information for a specific environment in which a brain function activation stimulus is regarded as being present, and detects brain function activation information. More specifically, the physiological state determination device 600 further includes the specific environment database 635 (specific environment storage unit) and the state information acquisition unit 618. The specific environment detection unit 641b matches the state information acquired by the state information acquisition unit 618 against the information in the specific environment database 635. If the state information acquired by the state information acquisition unit 618 is state information for a specific environment in which a brain activation stimulus is present, the specific environment detection unit 641b determines that the brain function activation stimulus is provided to the subject 300, and detects brain function activation information.

In the way described above, the physiological state determination device 600 is capable of detecting brain function activation information in response to detection of state information for a specific environment.

6-2-3-2

In the physiological state determination device 600 according to this embodiment, furthermore, when the specific environment detection unit 641b detects that state information in the predetermined environment K is state information for a specific environment in which a brain function activation stimulus is regarded as being present, the face change information acquisition unit 642 acquires face change information.

Accordingly, in the physiological state determination device 600, when state information for a specific environment is detected, the face change information acquisition unit 642 acquires face change information. This can avoid acquisition and/or storage of information unnecessary for determination.

In the physiological state determination device 600 according to this embodiment, the face change information acquisition unit 642 acquires face change information used as a reference at any timing when no brain function activation stimulus is provided to the subject 300. With the use of the face change information used as a reference, the physiological state determination unit can determine a physiological state of the subject 300 from face change information acquired when the specific environment detection unit 641b detects brain function activation stimulus information.

6-2-3-3

Additionally, the physiological state determination device 600 according to this embodiment has advantageous effects similar to those of the physiological state determination device 500 according to the first embodiment in (6-1-3-3) to (6-1-3-10).

(6-2-4) Modifications of Physiological State Determination Device 600

(6-2-4-1) Modification 2A

Figure 34:
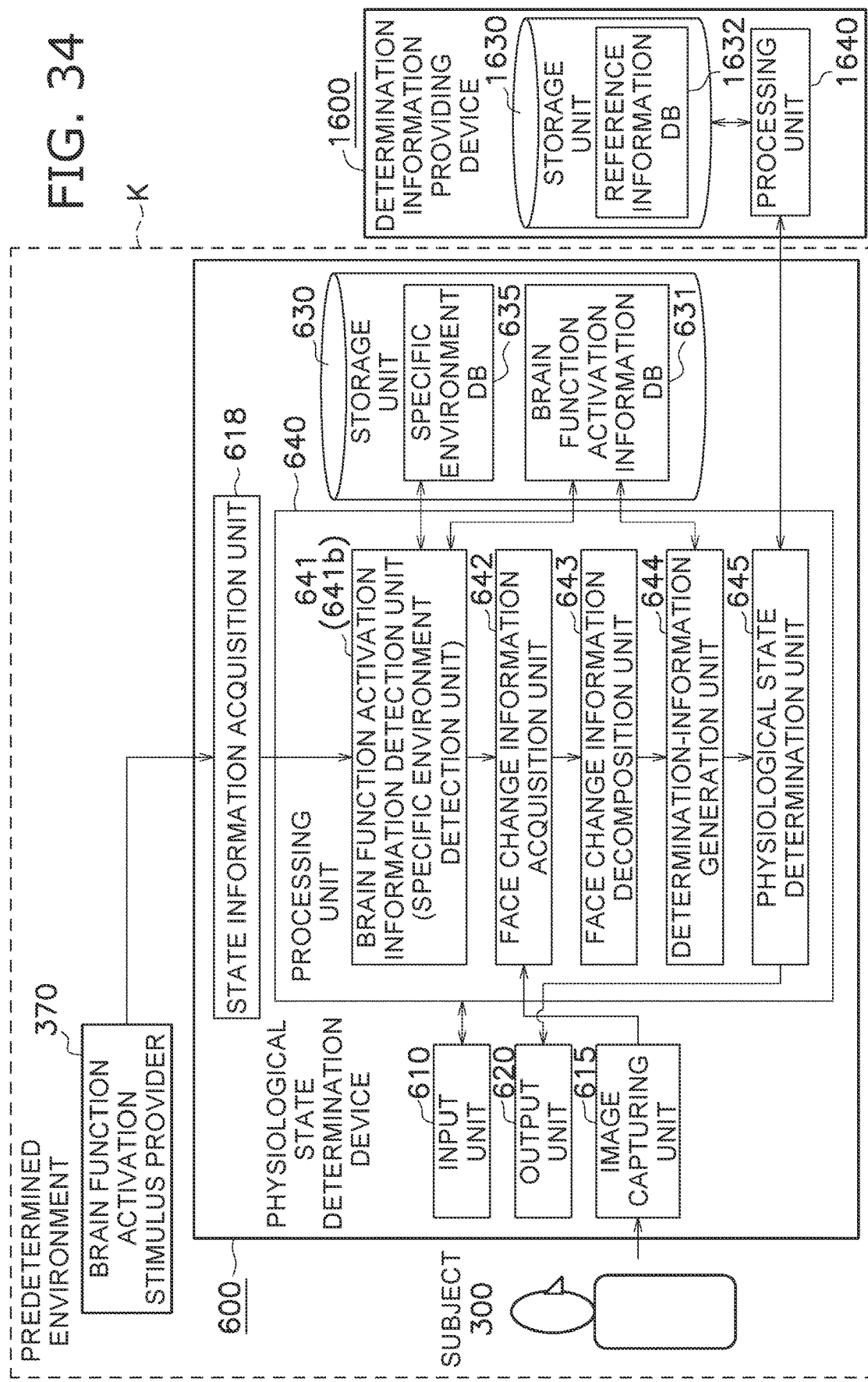
FIG. 34 is a schematic diagram illustrating the configuration of a physiological state determination device 600 according to Modification 2A of the second embodiment.

As illustrated in FIG. 34, the physiological state determination device 600 according to this embodiment may utilize a determination information providing device 1600 or the like located on a network. The configuration of a physiological state determination device 600 according to Modification 2A is similar to the configuration of the physiological state determination device 500 according to the modification of the first embodiment. Accordingly, in the physiological state determination device 600 according to Modification 2A, the physiological state determination unit 645 can determine the physiological state level of the subject 300 by using an external network.

Furthermore, the configuration of this modification can implement the determination of a physiological state using big data. That is, the reference correlation value r1 and the predetermined amount of change Δr are determined from big data. Specifically, the reference correlation value r1, which is calculated on the basis of a reference determination component obtained by providing brain function activation information to a person other than the subject 300, is used. This can optimize the reference information, as necessary.

(6-2-4-2) Modification 2B

Figure 35:
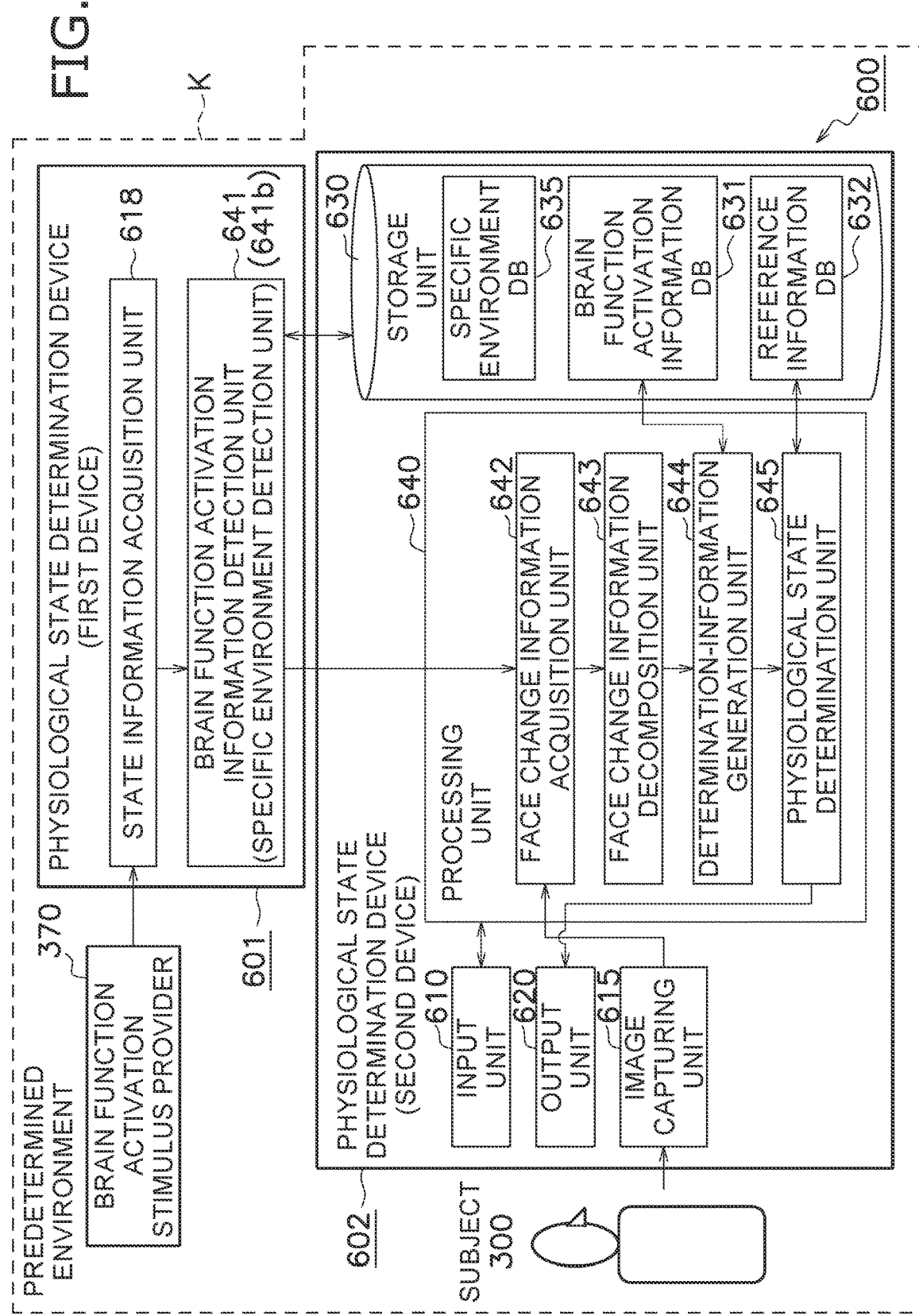
FIG. 35 is a schematic diagram illustrating the configuration of a physiological state determination device 600 according to Modification 2B of the second embodiment.

In the physiological state determination device 600 according to this embodiment, furthermore, as illustrated in FIG. 35, the brain function activation information detection unit 641 may be contained in a first device 601. In this case, the other configuration including the face change information acquisition unit 642 and the physiological state determination unit 645 is contained in a second device 602. The first device 601 and the second device 602 execute information communication to determine the physiological state of the subject 300. As described above, separating the first device 601 for detecting brain function activation information from the second device 602 having the other configuration allows only the first device 601 to be moved. As a result, the physiological state determination device 600 can increase the flexibility of the location where brain function activation information can be detected.

(6-2-4-3) Modification 2C

Figure 36:
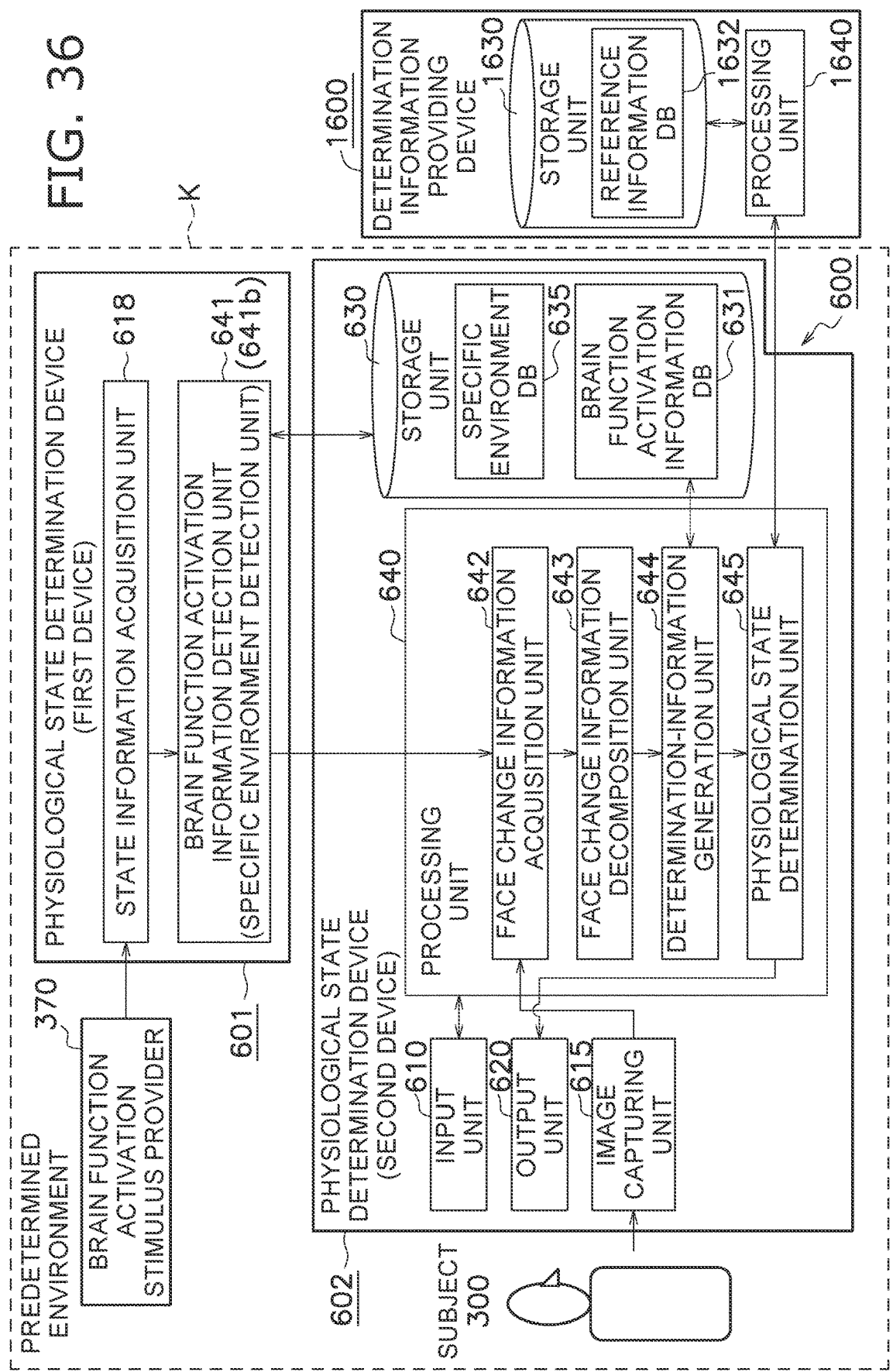
FIG. 36 is a schematic diagram illustrating the configuration of a physiological state determination device 600 according to Modification 2C of the second embodiment.

As illustrated in FIG. 36, the physiological state determination device 600 according to this embodiment may have a configuration obtained by combining Modification 2A and Modification 2B. With this configuration, a physiological state determination device 600 having advantageous effects of both Modification 2A and Modification 2B can be provided.

(6-2-4-4) Modification 2D

Figure 37:
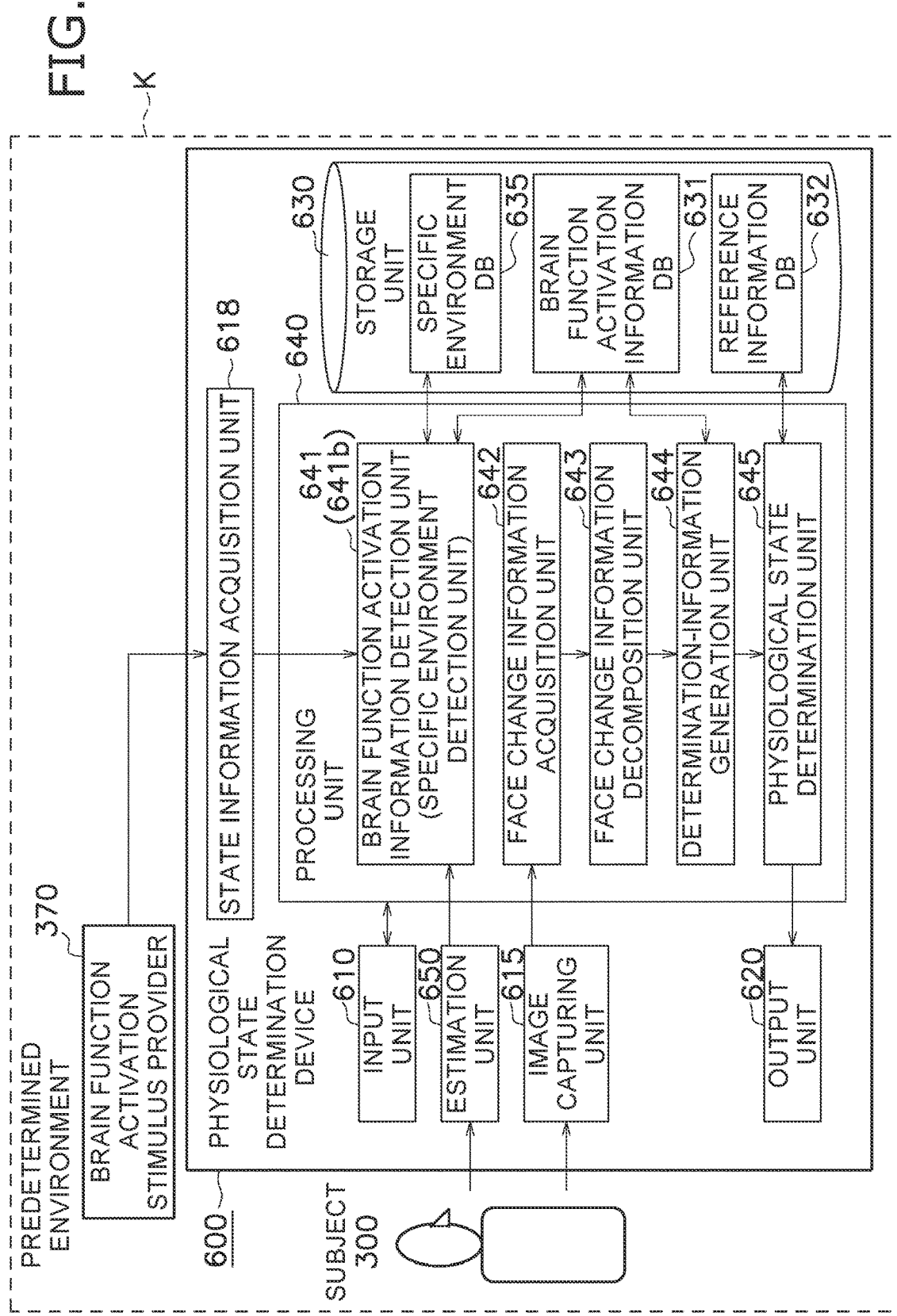
FIG. 37 is a schematic diagram illustrating the configuration of a physiological state determination device 600 according to Modification 2D of the second embodiment.

As illustrated in FIG. 37, the physiological state determination device 600 according to this embodiment may further include an estimation unit 650 that estimates that a brain function activation stimulus is provided to the subject 300. Specifically, the estimation unit 650 estimates that a brain function activation stimulus is provided to a subject on the basis of information on any one or combination of the line of sight, the angle of the face, and the physical activity of the subject. When the estimation unit 650 estimates that a brain function activation stimulus is provided, the specific environment detection unit 641b detects whether state information in the predetermined environment K is the state information for the specific environment in which the brain function activation stimulus is regarded as being present.

With this configuration, a physiological state determination device 600 according to Modification 2D can obtain a more reliable determination result of determining a physiological state by estimating that a brain function activation stimulus is provided to the subject 300.

The physical activity includes any activity of the body, such as an operation of braking a vehicle or the like, an operation of touching a tablet with a pen or the like, and checking an audio response to the words spoken by the other party of the call.

(6-3) Third Embodiment

FIG. 38 is a schematic diagram illustrating the configuration of a physiological state determination device 700 according to a third embodiment. The same portions as those described previously are assigned substantially the same numerals (numerals with the last two digits being the same for these portions), and will not be repeatedly described.

The physiological state determination device 700 according to this embodiment is constructed by combining the physiological state determination device 500 according to the first embodiment and the physiological state determination device 600 according to the second embodiment described above. The physiological state determination device 700 includes an operation information acquisition unit 717 and a state information acquisition unit 718, and a brain function activation information detection unit 741 functions as a specific operation detection unit 741a and/or a specific environment detection unit 741b. The operation information acquisition unit 717, the state information acquisition unit 718, the specific operation detection unit 741a, and the specific environment detection unit 741b have functions and/or configurations similar to those of the operation information acquisition unit 517, the state information acquisition unit 618, the specific operation detection unit 541a, and the specific environment detection unit 641b described above, respectively. In summary, the physiological state determination device 700 according to this embodiment is capable of detecting brain function activation information in response to detection of a specific operation on the predetermined device 360 and/or detection of state information for a specific environment.

In the physiological state determination device 700 according to this embodiment, furthermore, when the specific operation detection unit 741a detects that a specific operation is performed on the predetermined device 360, a face change information acquisition unit 742 acquires face change information. Alternatively, when the specific environment detection unit 741b detects state information in the predetermined environment K as state information for a specific environment in which a brain function activation stimulus is regarded as being present, the face change information acquisition unit 742 acquires face change information. Alternatively, when the specific operation detection unit 741a detects a specific operation and the specific environment detection unit 741b detects a specific environment, the face change information acquisition unit 742 acquires face change information.

Accordingly, in the physiological state determination device 700, when a specific operation on the predetermined device 360 is detected and/or when state information for a specific environment is detected, the face change information acquisition unit 742 acquires face change information. This can avoid acquisition and/or storage of information unnecessary for determination.

Note

Note that the present invention is not limited to the embodiments as they are. The present invention can be embodied by modifying constituent elements without departing from the gist thereof at the stage of implementation. In the present invention, furthermore, a variety of aspects of the invention can be constituted by appropriate combinations of a plurality of constituent elements disclosed in the embodiments described above. For example, several constituent elements from among all the constituent elements described in the embodiments may be omitted. In addition, in different embodiments, constituent elements may be combined, as appropriate.

According to the present invention, brain activity can be easily estimated. Thus, the present invention is useful in applications to physiological state visualization devices that visualize the physiological state of a subject on the basis of the brain activity.

What is claimed is:

1. A physiological state determination device for determining a predetermined physiological state of a subject, the physiological state determination device comprising:

a processor including
  a brain function activation information detection unit configured to detect brain function activation information corresponding to the physiological state;
  a face change information acquisition unit configured to acquire face change information indicating a time-series change in face data of the subject, the face data being a facial skin temperature of the subject or facial blood-circulation-amount-data based on facial RGB data of the subject; and
  a physiological state determination unit configured to determine the predetermined physiological state of the subject based on the brain function activation information and the face change information; and
an estimation sensor configured to estimate that a brain function activation stimulus is provided to the subject,
the brain function activation information detection unit including a specific operation detection unit that, when a specific operation is performed on a predetermined device prior to acquiring the face change information by the subject or a measuring person other than the subject, determines that the brain function activation stimulus is provided to the subject and detects the brain function activation information.

2. The physiological state determination device according to claim 1, wherein
the brain function activation information detection unit includes
  a specific environment detection unit that, when state information in a predetermined environment is state information for a specific environment in which the brain function activation stimulus is regarded as being present, determines that the brain function activation stimulus is provided to the subject and detects the brain function activation information.

3. The physiological state determination device according to claim 2, wherein
the face change information acquisition unit is further configured so that one or both of
  the face change information acquisition unit acquires the face change information when the specific operation detection unit detects that the specific operation is performed on the predetermined device, and
  the face change information acquisition unit acquires the face change information when the specific environment detection unit detects that the state information in the predetermined environment is the state information for the specific environment in which the brain function activation stimulus is regarded as being present.

4. The physiological state determination device according to claim 3, wherein
the face change information acquisition unit is further configured so that one or both of
  the face change information acquisition unit acquires a reference for the face change information when the specific operation detection unit does not detect the specific operation, and
  the face change information acquisition unit acquires a reference for the face change information when the specific environment detection unit does not detect the state information for the specific environment.

5. The physiological state determination device according to claim 2, wherein
the processor includes a first processor and a second processor,
  the brain function activation information detection unit being contained in the first processor,
  the face change information acquisition unit and the physiological state determination unit being contained in the second processor, and
  the first processor and the second processor execute information communication to determine a physiological state of the subject.

6. The physiological state determination device according to claim 2, wherein
when the estimation sensor estimates that the brain function activation stimulus is provided, the specific environment detection unit detecting whether the state information in the predetermined environment is the state information for the specific environment in which the brain function activation stimulus is regarded as being present.

7. The physiological state determination device according to claim 6, wherein
the estimation sensor is further configured to estimate that the brain function activation stimulus is provided to the subject based on information on any one or any combination of a line of sight, an angle of a face, and a physical activity of the subject.

8. The physiological state determination device according to claim 2, further comprising:
a specific environment storage unit that stores, in advance, the state information for the specific environment in which the brain activation stimulus is regarded as being present, the specific environment storage unit including a memory; and
a state information acquisition sensor configured to acquire state information for the predetermined environment,
the specific environment detection unit
  matching the state information acquired by the state information acquisition sensor against the state information stored in the specific environment storage unit, and
  determining whether the state information acquired by the state information acquisition sensor is state information for a specific environment in which the brain activation stimulus is present to detect the brain function activation information.

9. The physiological state determination device according to claim 1, wherein
the processor further includes a determination-information generation unit configured to generate determination information from the face change information,
the physiological state determination unit determining the physiological state based on the determination information.

10. The physiological state determination device according to claim 9, wherein
the processor further includes a face change information decomposition unit configured to decompose the face change information into a plurality of components by using singular value decomposition, principal component analysis, or independent component analysis,
the determination-information generation unit
  extracting a component related to the brain function activation information from among the plurality of components as a determination component, and
  generating the determination information from the determination component.

11. The physiological state determination device according to claim 3, wherein
the processor includes a first processor and a second processor,
the brain function activation information detection unit being contained in the first processor,
the face change information acquisition unit and the physiological state determination unit being contained in the second processor, and
the first processor and the second processor execute information communication to determine a physiological state of the subject.

12. The physiological state determination device according to claim 3, wherein
when the estimation sensor estimates that the brain function activation stimulus is provided, the specific environment detection unit detecting whether the state information in the predetermined environment is the state information for the specific environment in which the brain function activation stimulus is regarded as being present.

13. The physiological state determination device according to claim 3, further comprising:
a specific environment storage sensor that stores, in advance, the state information for the specific environment in which the brain activation stimulus is regarded as being present, the specific environment storage unit including a memory; and
a state information acquisition sensor configured to acquire state information for the predetermined environment,
the specific environment detection unit
matching the state information acquired by the state information acquisition sensor against the state information stored in the specific environment storage unit, and
determining whether the state information acquired by the state information acquisition sensor is state information for a specific environment in which the brain activation stimulus is present to detect the brain function activation information.

14. The physiological state determination device according to claim 3, wherein
the processor includes a determination-information generation unit configured to generate determination information from the face change information,
the physiological state determination unit determining the physiological state based on the determination information.

15. The physiological state determination device according to claim 4, wherein
the processor includes a first processor and a second processor,
the brain function activation information detection unit being contained in the first processor,
the face change information acquisition unit and the physiological state determination unit being contained in the second processor, and
the first processor and the second processor execute information communication to determine a physiological state of the subject.

16. The physiological state determination device according to claim 4, wherein
when the estimation sensor estimates that the brain function activation stimulus is provided, the specific environment detection unit detecting whether the state information in the predetermined environment is the state information for the specific environment in which the brain function activation stimulus is regarded as being present.

17. The physiological state determination device according to claim 4, further comprising:
a specific environment storage sensor that stores, in advance, the state information for the specific environment in which the brain activation stimulus is regarded as being present, the specific environment storage unit including a memory; and
a state information acquisition sensor configured to acquire state information for the predetermined environment,
the specific environment detection unit
matching the state information acquired by the state information acquisition sensor against the state information stored in the specific environment storage unit, and
determining whether the state information acquired by the state information acquisition sensor is state information for a specific environment in which the brain activation stimulus is present to detect the brain function activation information.

18. The physiological state determination device according to claim 4, wherein
the processor includes a determination-information generation unit configured to generate determination information from the face change information,
the physiological state determination unit determining the physiological state based on the determination information.

19. The physiological state determination device according to claim 5, wherein
when the estimation sensor estimates that the brain function activation stimulus is provided, the specific environment detection unit detecting whether the state information in the predetermined environment is the state information for the specific environment in which the brain function activation stimulus is regarded as being present.

20. The physiological state determination device according to claim 5, wherein
the processor includes a determination-information generation unit configured to generate determination information from the face change information,
the physiological state determination unit determining the physiological state based on the determination information.

* * * * *